US012577587B2

(12) United States Patent
Brummelkamp et al.

(10) Patent No.: US 12,577,587 B2
(45) Date of Patent: *Mar. 17, 2026

(54) COMPOSITIONS AND METHODS FOR MAMMALIAN GENETICS AND USES THEREOF

(71) Applicant: Whitehead Institute for Biomedical Research, Cambridge, MA (US)

(72) Inventors: Thijn R. Brummelkamp, Amsterdam (NL); Jan E. Carette, Palo Alto, CA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 143 days.

This patent is subject to a terminal disclaimer.

(21) Appl. No.: 18/128,994

(22) Filed: Mar. 30, 2023

(65) Prior Publication Data

US 2023/0374544 A1 Nov. 23, 2023

Related U.S. Application Data

(63) Continuation of application No. 16/214,026, filed on Dec. 7, 2018, now Pat. No. 11,667,928, which is a continuation of application No. 13/383,156, filed as application No. PCT/US2010/041628 on Jul. 9, 2010, now abandoned.

(60) Provisional application No. 61/224,338, filed on Jul. 9, 2009.

(51) Int. Cl.
  *C12N 15/10* (2006.01)
  *C12N 15/86* (2006.01)

(52) U.S. Cl.
  CPC ......... *C12N 15/86* (2013.01); *C12N 15/1051* (2013.01); *C12N 15/1079* (2013.01); *C12N 2740/13043* (2013.01); *C12N 2800/107* (2013.01); *C12N 2800/60* (2013.01); *C12N 2840/44* (2013.01)

(58) Field of Classification Search
  CPC ................................................. C12N 15/1051
  See application file for complete search history.

(56) References Cited

U.S. PATENT DOCUMENTS

| | | | |
|---|---|---|---|
| 6,080,576 A | 6/2000 | Zambrowicz et al. | |
| 2003/0104613 A1 | 6/2003 | Gerdil | |
| 2008/0206744 A1 | 8/2008 | Zacharias | |
| 2010/0184051 A1 | 7/2010 | Hochedlinger et al. | |

FOREIGN PATENT DOCUMENTS

| | | | |
|---|---|---|---|
| JP | 2003512053 A | 4/2003 | |
| WO | 2005/082088 A2 | 9/2005 | |
| WO | 2008-151058 A2 | 12/2008 | |

OTHER PUBLICATIONS

Carette et al., 2011, Nature, vol. 477(7364), pp. 340-343 (Year: 2011).*
Shiras et al. (2003, Neoplasia, vol. 5(6), pp. 520-532). (Year: 2003).*
Carette, et al., "Haploid genetic screens in human cells identify host factors used by pathogens," Science, 326: 1231-1235 (2009).
Kotecki, et al., "Isolation and characterization of a near-haploid human cell line," Exp. Cell Res., 252(2): 273-280 (1999).
Meissner, et al., "Direct reprogramming of genetically unmodified fibroblasts into pluripotent stem cells," Nat. Biotechnol., 25(10): 1177-1181 (2007).
Nord, et al., "The Gene Trap Consortium Website: A Portal to All Publically Available Gene Trap Cell Lines in Mouse," Nucleic Acids Research, 34: D642-D648 (2006).
Takahashi, et al., "Induction of pluripotent stem cells from mouse embryonic and adult fibroblast cultures by defined factors," Cell, 126(4): 663-676 (2006).
Bostock, et al., "A stable 'near-haploid' mammalian cell line (*Dipodomys ordii*)", Experimental Cell Research, 106(2): 373-377(1977).
Susan Forsburg, "The Art and Design of Genetic Screens: Yeast", Nature Reviews, 659 (2001).
Ma, et al., "Prevalence of off-target effects in Drosophilia RNA inference screens", Nature, 443(7109): 359-396 (2006).
Nobukuni, et al.,"Gene Trap Mutagenesis-based Forward Genetic Approach Reveals That the Tumor Suppressor OVCA1 is a component of the Biosynthetic Pathway of Diphthamide on Elongation Factor 2", Journal or Biological Chemistry, 280(11): 10572-10577 (2005).
Carette, Jan E., et al. "Ebola Virus Entry Requires the Cholesterol Transporter Niemann-Pick C1." Nature 477.7364: 340-343 (2011).
Jae, Lucas T., et al. "Deciphering the Glycosylome of Dystroglycanopathies using Haploid Screens for Lassa Virus Entry." Science 340.6131: 479-483 (2013).
Kotecki, et al., "Isolation and characterization of a near-haploid human cell line," Experimental Cell Research, 252.2: 273-280 (1999).
Guenet, Jean-Louis, "Assessing the genetic component of the susceptibility of mice to viral infections," Briefings in Functional Genomics and Proteomics, 4.3: 225-240 (2005).
Evans, et al., "Gene expression as a drug discovery tool," Nature Genetics, 36.3: 214-215 (2004).
Jenner, et al., "Insights into host responses against pathogens from transcriptional profiling," Nature Reviews Microbiology, 3.4: 281-294 (2005).
International Search Report for International Application No. PCT/US2010/041628, dated May 24, 2011.
European Supplementary Search Report for European Application EP10797959, dated Sep. 28, 2012.

(Continued)

*Primary Examiner* — Anoop K Singh
*Assistant Examiner* — David A Montanari
(74) *Attorney, Agent, or Firm* — Morse, Barnes-Brown & Pendleton, P.C.; Lisa M. Warren, Esq.; Erin E. Bryan, Esq.

(57) ABSTRACT

The invention provides compositions and methods for performing mammalian cell genetics, e.g., genetic screens, using near-haploid cells. The invention further provides genes and gene products isolated using the inventive methods and methods of use thereof.

6 Claims, 24 Drawing Sheets

Specification includes a Sequence Listing.

(56) References Cited

OTHER PUBLICATIONS

Final Office Action in Application No. 13/383, 156, dated Sep. 7, 2018.

Non-Final Office Action in U.S. Appl. No. 13/383,156, dated Dec. 15, 2017.

Final Office Action in U.S. Appl. No. 13/383,156, dated Mar. 8, 2016.

Non-Final Office Action in U.S. Appl. No. No. 13/383,156, dated Sep. 1, 2015.

Final Office Action in U.S. Appl. No. No. 13/383,156, dated Sep. 5, 2014.

Non-Final Office Action in U.S. Appl. No. No. 13/383,156, dated Nov. 6, 2013.

Shiras, et al., "A Unique Model System for Tumor Progression in GBM Comprising Two Developed Human Neuro-Epithelial Cell Lines with Differential Transforming Potential and Coexpressing Neuronal and Glial Markers," Neoplasia, 5(6): 520-532 (Nov. 2003).

* cited by examiner

FIG. 2A control

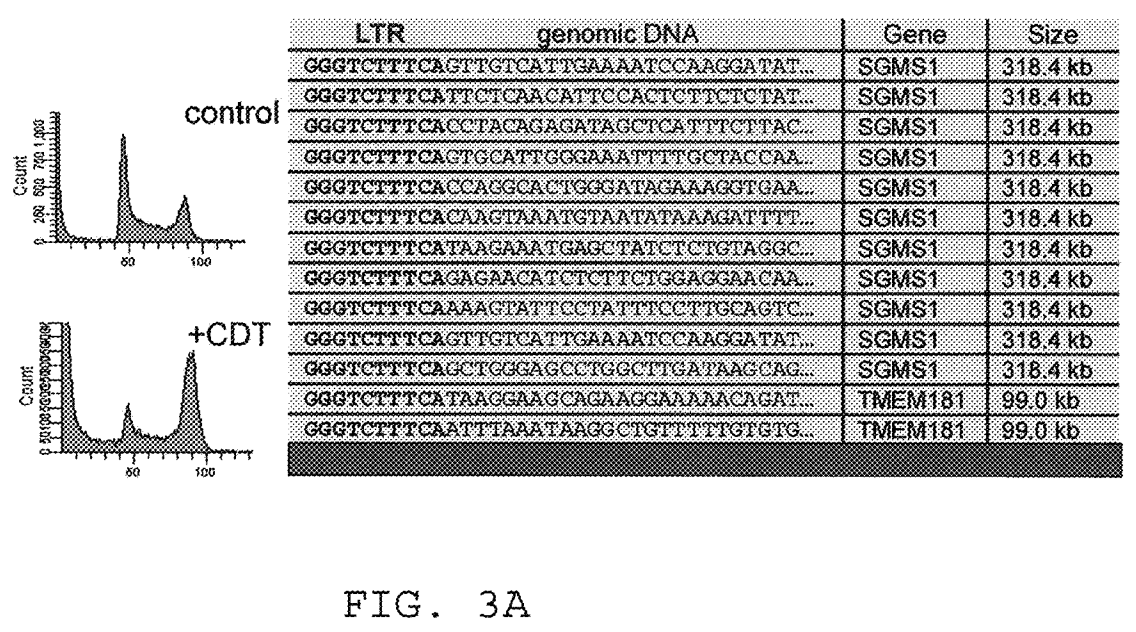

+CDT

| LTR genomic DNA | Gene | Size |
|---|---|---|
| GGGTCTTTCAGTTGTCATTGAAAATCCAAGGATAT... | SGMS1 | 318.4 kb |
| GGGTCTTTCATTCTCAACATTCCACTCTTCTCTAT. | SGMS1 | 318.4 kb |
| GGGTCTTTCACCTACAGAGATAGCTCATTTCTTAC. | SGMS1 | 318.4 kb |
| GGGTCTTTCACTGCATTGGGAAATTTTGCTACCAA. | SGMS1 | 318.4 kb |
| GGGTCTTTCACCAGGCACTGGGATAGAAAGGTGAA. | SGMS1 | 318.4 kb |
| GGGTCTTTCACAAGTAAATGTAATTATTAAGATTTT... | SGMS1 | 318.4 kb |
| GGGTCTTTCATAAGAGAACATCTCTTCTTGTAGGC.. | SGMS1 | 318.4 kb |
| GGGTCTTTCAGAAAGTAGTCTCTTCTGGAGGAACAA. | SGMS1 | 318.4 kb |
| GGGTCTTTCAAAAGTATTCCTATTTCCTTGCAGTC.. | SGMS1 | 318.4 kb |
| GGGTCTTTCAGTTGTCATTGAAAATCCAAGGATAT... | SGMS1 | 318.4 kb |
| GGGTCTTTCAGCTGGGAGCCTTGCTTGATAAGCTAG... | SGMS1 | 318.4 kb |
| GGGTCTTTCATAAGGAAGCAGAAGAAGGAAAAACAGAT... | TMEM181 | 99.0 kb |
| GGGTCTTTCAGTTAAAATAAGGCTGTTTTTGTGTG.. | TMEM181 | 99.0 kb |

FIG. 3A

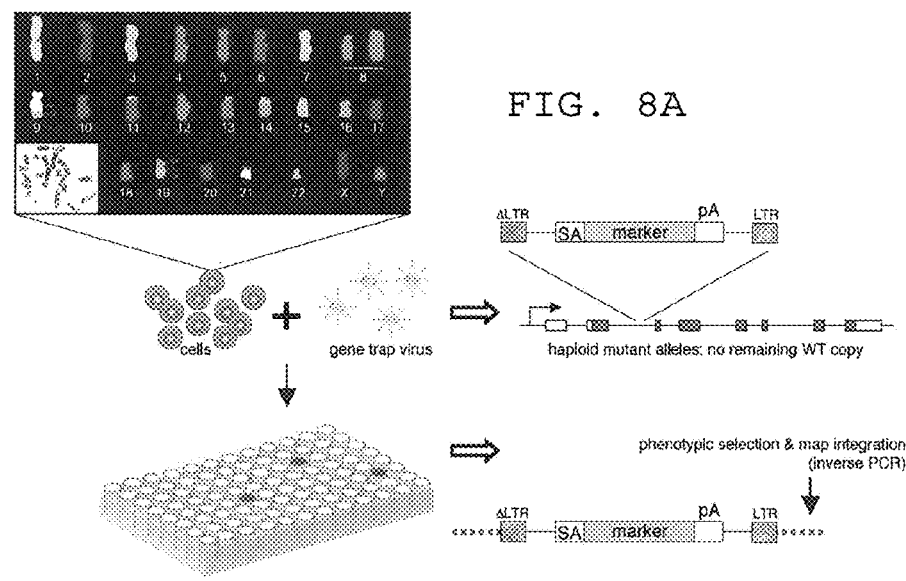
FIG. 8A
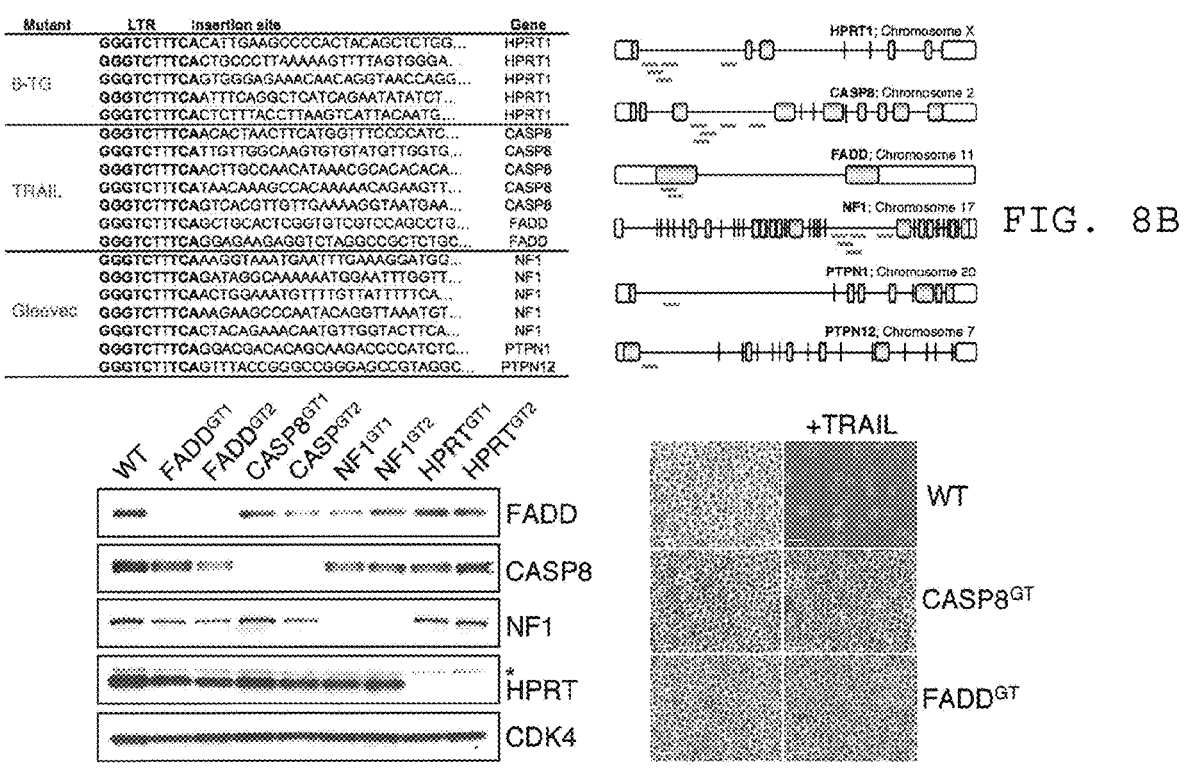
FIG. 8B
FIG. 8C
FIG. 8D

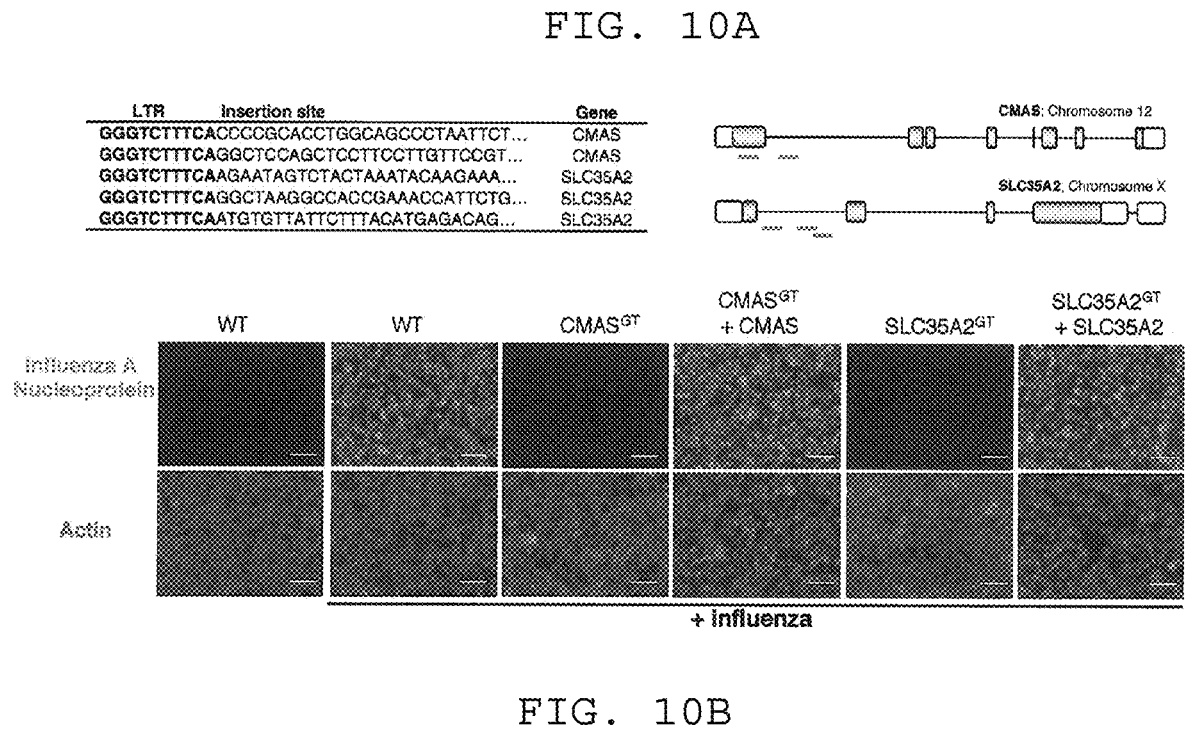

| LTR | Insertion site | Gene |
|---|---|---|
| GGGTCTTTCACCCCGCACCTGGCAGCCCTAATTCT... | | CMAS |
| GGGTCTTTCAGGCTCCAGCTCCTTCCTTGTTCCGT... | | CMAS |
| GGGTCTTTCAAGAATAGTCTACTAAATACAAGAAA... | | SLC35A2 |
| GGGTCTTTCAGGCTAAGGCCACCGAAACCATTCTG... | | SLC35A2 |
| GGGTCTTTCAATGTGTTATTCTTTACATGAGACAG... | | SLC35A2 |

CMAS: Chromosome 12

SLC35A2, Chromosome X

FIG. 10B

Untreated        0.2 ul/ml        2ul/ml

U2OS

U2OS-
TMEM181

1 day post treatment with cdt

HELA

HELA-
TMEM181

2 days post treatment with cdt

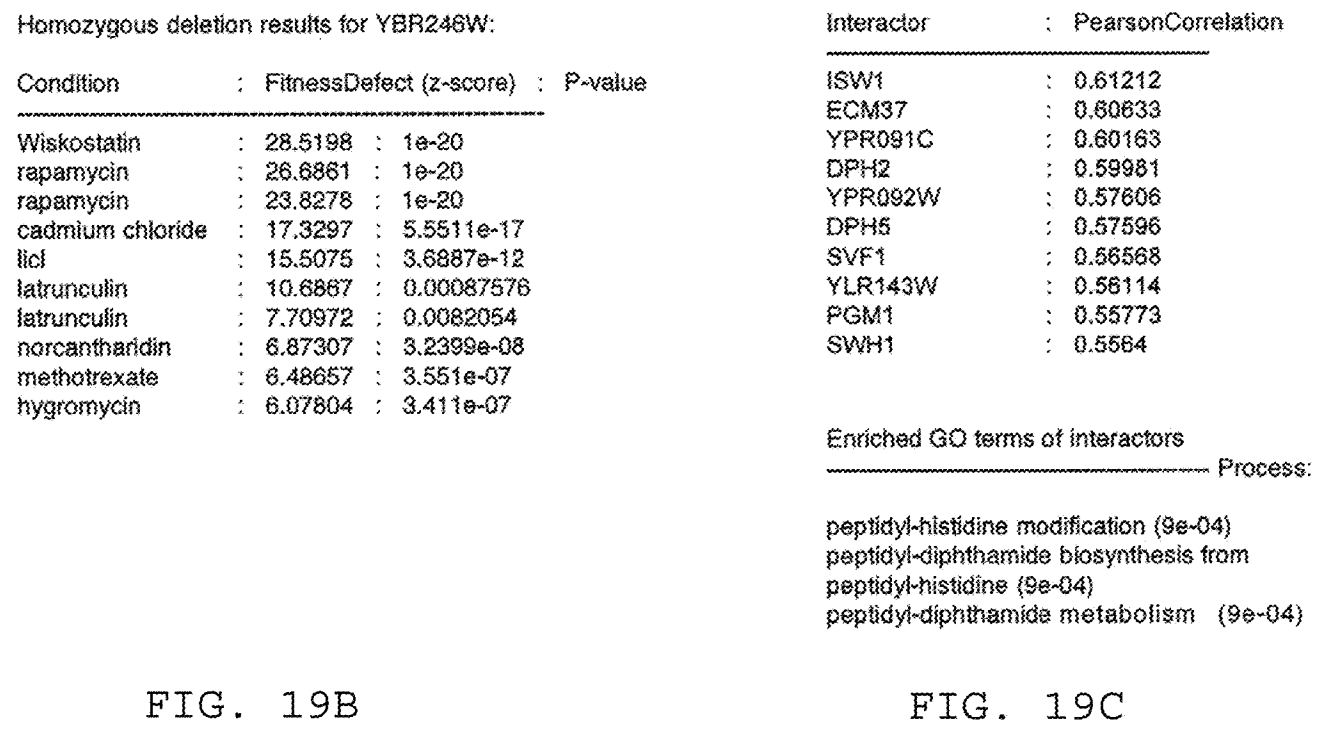

Homozygous deletion results for YBR246W:

| Condition | FitnessDefect (z-score) | P-value |
|---|---|---|
| Wiskostatin | 28.5198 | 1e-20 |
| rapamycin | 26.6861 | 1e-20 |
| rapamycin | 23.8278 | 1e-20 |
| cadmium chloride | 17.3297 | 5.5511e-17 |
| licl | 15.5075 | 3.6887e-12 |
| latrunculin | 10.6867 | 0.00087576 |
| latrunculin | 7.70972 | 0.0082054 |
| norcantharidin | 6.87307 | 3.2399e-08 |
| methotrexate | 6.48657 | 3.551e-07 |
| hygromycin | 6.07804 | 3.411e-07 |

FIG. 19B

| Interactor | PearsonCorrelation |
|---|---|
| ISW1 | 0.61212 |
| ECM37 | 0.60633 |
| YPR091C | 0.60163 |
| DPH2 | 0.59981 |
| YPR092W | 0.57606 |
| DPH5 | 0.57596 |
| SVF1 | 0.56568 |
| YLR143W | 0.56114 |
| PGM1 | 0.55773 |
| SWH1 | 0.5564 |

Enriched GO terms of interactors ———————————— Process:

peptidyl-histidine modification (9e-04)
peptidyl-diphthamide biosynthesis from
peptidyl-histidine (9e-04)
peptidyl-diphthamide metabolism (9e-04)

FIG. 19C

COMPOSITIONS AND METHODS FOR MAMMALIAN GENETICS AND USES THEREOF

RELATED APPLICATIONS

This application is a continuation of U.S. application Ser. No. 16/214,026, filed Dec. 7, 2018, which is a continuation of U.S. application Ser. No. 13/383,156, filed Apr. 16, 2012, which is a national stage filing under 35 U.S.C. 371 of International Application No. PCT/US2010/041628, filed Jul. 9, 2010, which claims the benefit of U.S. Provisional Application Ser. No. 61/224,338, filed Jul. 9, 2009, the entire teachings of which are incorporated herein by reference. International Application PCT/US2010/041628 was published under PCT Article 21(2) in English.

STATEMENT REGARDING SEQUENCE LISTING

The Sequence Listing associated with this application is provided in .xml format in lieu of a paper copy and is hereby incorporated by reference into the specification. The name of the .xml file containing the Sequence Listing is WIBR-110-103.xml. The xml file is 2,39,271 bytes, was created on Apr. 17, 2023, and is being submitted electronically via Patent Center.

BACKGROUND OF THE INVENTION

Large-scale gene inactivation through mutagenesis in genetically tractable model organisms such as the budding yeast, the fruit-fly, and the worm is one of the most powerful tools for gaining insight into biological processes. Despite recent advances in RNA interference, successful whole-genome genetic screening in mammalian cells remains a daunting task.

SUMMARY OF THE INVENTION

Classical genetics using induced mutations has developed into one of the most powerful approaches to elucidate the genetic components that underlie biological processes, independently of prior knowledge or assumptions. The study of cultured human cells allows the recapitulation of aspects of human disease. However, the inability to generate and recover bi-allelic mutants in human diploid cells limits the contribution of mutagenesis-based genetics to the understanding of human disease. The present invention provides compositions and methods for identifying mammalian genes, gene products, and/or gene function(s) that affect cell phenotype.

In one aspect, the invention provides a new approach that allows for the study of phenotypes caused by recessive mutations for most human genes, induced by a single mutagenic event using mutagenesis in human cells that are haploid or near haploid. The invention provides a method of identifying a gene that affects cell phenotype, the method comprising steps of: (a) introducing a gene trap vector into near-haploid mammalian cells in culture, wherein said gene trap vector comprises a nucleic acid construct that integrates into the genome of said near-haploid mammalian cell, and wherein the nucleic acid construct comprises a nucleic acid that allows the identification of a cell containing said nucleic acid; (b) identifying a cell containing said gene trap vector integrated into its genome, wherein the cell exhibits a phenotype of interest; and (c) identifying a gene into which the nucleic acid construct integrated, thereby identifying a gene that affects cell phenotype. In some embodiments the nucleic acid encodes a reporter that allows the identification of a cell expressing the nucleic acid. In some embodiments the near-haploid mammalian cell is a human cell. In some embodiments the near-haploid mammalian cell is a KBM7 cell. In some embodiments the near-haploid mammalian cell is genetically modified.

In some embodiments the nucleic acid construct comprises in operable association in a 5' to 3' direction: (1) a splice acceptor site; (2) a nucleic acid encoding a reporter that allows the identification of a cell expressing the nucleic acid; and (3) a polyadenylation sequence. In some embodiments the splice acceptor site is an adenoviral splice acceptor sites. In some embodiments the gene trap vector is a polyA gene trap vector. In some embodiments the phenotype of interest is altered susceptibility to infection by a pathogen as compared with susceptibility of a suitable control cell to the pathogen. In some embodiments the method comprises identifying cells that are resistant to the pathogen. In some embodiments the method comprises identifying cells that express the reporter and are resistant to the pathogen. In some embodiments the phenotype of interest is altered sensitivity to a compound of interest as compared with sensitivity of suitable control cell to the compound. In some embodiments the compound of interest is a therapeutic agent, e.g., a therapeutic agent used to treat cancer. In some embodiments the compound of interest is a cytotoxic agent. In some embodiments the compound of interest is a toxin, e.g., a bacterial toxin. In some embodiments the method comprises identifying cells that are resistant to the toxin, e.g., that survive and/or proliferate in the presence of the toxin. In some embodiments the method comprises identifying cells that express the reporter and are resistant to the toxin. In some embodiments the phenotype of interest is altered propensity to undergo apoptosis as compared with propensity of a suitable control cell to undergo apoptosis. In some embodiments the method comprises recovering and sequencing a portion of the gene. In some embodiments massively parallel sequencing is used to obtain sequence information regarding multiple insertions. Regions of the genome having multiple insertions are likely to contain genes affecting the phenotype. In some embodiments the near-haploid mammalian cell further comprises a reporter useful to identify cells having a phenotype of interest. In some embodiments step (a) comprises introducing the gene trap vector into cells of a near-haploid mammalian cell line, wherein the gene trap vector comprises a nucleic acid construct comprising a nucleic acid encoding a reporter that allows the identification of cells expressing said nucleic acid, wherein said nucleic acid construct integrates into the genome of at least some of said near-haploid mammalian cells; (b) identifying a plurality of cells containing said gene trap vector so integrated, wherein the cells exhibit a phenotype of interest; and (c) identifying a plurality of genes into which the nucleic acid construct integrated, thereby identifying a plurality of genes that affect cell phenotype.

In another aspect the invention provides a method of identifying a gene that encodes a host cell factor that affects susceptibility to a pathogen, the method comprising steps of: (a) introducing a gene trap vector into near-haploid mammalian cells, wherein the gene trap vector comprises a nucleic acid construct comprising a nucleic acid encoding a reporter that allows the identification of a cell expressing said nucleic acid, wherein said nucleic acid construct integrates into the genome of said haploid mammalian cell; (b) contacting the near-haploid mammalian cells with a pathogen or virulence factor; (c) identifying a cell that contains said nucleic acid construct integrated into its genome and exhibits altered susceptibility to the pathogen or virulence factor; and (c) identifying a gene into which the nucleic acid construct integrated, thereby identifying a gene that encodes a host cell factor that affects susceptibility to a pathogen. In some embodiments step (b) comprises identifying a cell that is resistant to the pathogen or virulence factor.

In another aspect, the invention provides a method of identifying a gene that encodes a gene product that plays a role in drug activity of an agent in mammalian cells, the method comprising steps of: (a) introducing a gene trap vector into near-haploid mammalian cells, wherein the gene trap vector comprises a nucleic acid construct comprising a nucleic acid encoding a reporter that allows the identification of a cell expressing said nucleic acid, wherein said nucleic acid construct integrates into the genome of at least some of said near-haploid mammalian cells; (b) contacting the mammalian cells with an agent drug at a concentration sufficient to cause a detectable effect on said non-mutant near-haploid cells; (c) identifying a cell that contains said nucleic acid construct integrated into its genome and does not exhibit said effect; and (d) identifying a gene into which the nucleic acid construct integrated, thereby identifying a gene that encodes a gene product that plays a role in drug activity of the agent in mammalian cells. In some embodiments the agent is a drug.

In another aspect, the invention provides a gene trap vector comprising in operable association in a 5' to 3' direction: (1) an adenoviral splice acceptor site; (2) a nucleic acid encoding a reporter that allows the identification of a cell expressing said nucleic acid, wherein said reporter is not a neomycin resistance gene; and (3) a polyadenylation sequence. The invention further provides a near-haploid mammalian cell comprising said gene trap vector. In some embodiments the cell is a human cell. In some embodiments the cell is a KBM7 cell. In some embodiments the cell is genetically modified.

In another aspect the invention provides a mammalian cancer cell engineered to express a set of reprogramming factors sufficient to reprogram a normal mammalian somatic cell to pluripotency, e.g., Oct4, Sox2, Klf4, and c-Myc. In some embodiments the cell is a hematopoietic cancer cell. In some embodiments the cell is a human cancer cell. In some embodiments the cell is a KBM7 cell or a derivative thereof. In some embodiments the mammalian cancer cell is a cell of a cell line that is stable in culture for at least 10 passages.

In another aspect, the invention provides an adherent, near-haploid mammalian cell derived from a non-adherent near-haploid mammalian cell. In some embodiments the adherent, near-haploid mammalian cell is a derivative of a KBM7 cell.

The invention further provides a method of producing an adherent cell derived from of a mammalian cell that normally grows in suspension, the method comprising steps of: (a) providing a mammalian cell that normally grows in suspension; (b) engineering the cell to express a set of reprogramming factors sufficient to reprogram a normal mammalian somatic cell to pluripotency; (c) culturing descendants of the cell in non-ES cell medium under conditions suitable for cell proliferation; and (d) isolating an adherent descendant of the mammalian cell. In some embodiments the mammalian cell that normally grows in suspension is a near-haploid cell. In some embodiments the mammalian cell that normally grows in suspension is a cell of an immortalized mammalian cell line. In some embodiments the immortalized mammalian cell line is a KBM7 cell. In

4 some embodiments the method further comprises introducing a gene trap vector into at least some of the cells. In some embodiments the gene trap vector comprises in operable association: 1) a splice acceptor; 2) an exon located 3' to said splice acceptor, said exon encoding a reporter enabling the identification of a cell expressing said exon; and 3) a polyadenylation sequence located at the 3' end of said first exon.

The invention further provides method of producing a mammalian cell having a phenotype of interest other than pluripotency, the method comprising steps of: (a) providing a population of mammalian cells; (b) engineering the cells to express a set of reprogramming factors sufficient to reprogram a mammalian somatic cell to pluripotency; (c) culturing the cells under conditions suitable for proliferation; and (d) screening resulting cells to identify a cell having a phenotype of interest other than pluripotency. In some embodiments the mammalian cell is a near-haploid cell. In some embodiments the mammalian cell is a KBM7 cell. In some embodiments the method further comprises isolating a cell having a phenotype of interest other than pluripotency. In some embodiments the phenotype of interest is susceptibility to a pathogen. In some embodiments the method further comprises introducing a gene trap vector into at least some of the cells. In some embodiments the gene trap vector comprises in operable association: 1) a splice acceptor; 2) an exon located 3' to said splice acceptor, said exon encoding a reporter enabling the identification of a cell expressing said exon; and 3) a polyadenylation sequence located at the 3' end of said first exon.

In other aspects, the invention provides methods of using the identified genes and encoded gene products. For example, identified genes and gene products may be targets for drug discovery, or may be useful for engineering biosynthetic processes, e.g., processes of industrial, medical, or physiologic importance.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988. All patents, patent applications, and other publications mentioned herein are incorporated by reference in their entirety. Standard art-accepted meanings of terms are used herein unless indicated otherwise. Standard abbreviations for various terms are used herein.

BRIEF DESCRIPTION OF THE DRAWINGS

FIG. 1A is a 24-color FISH spectral karyotype analysis of the near-haploid KBM7 subclone. FIG. 1B shows a schematic outline of gene-trap vector integration in an endogenous gene. A schematic outline of the insertion sites indicates that all gene trap insertions interrupt the coding sequences of the trapped genes (filled boxes). FIG. 1C is a Western blot analysis of CD43 in cell line that has a GFP gene-trap integrated into the CD43 locus.

Figure 2A:
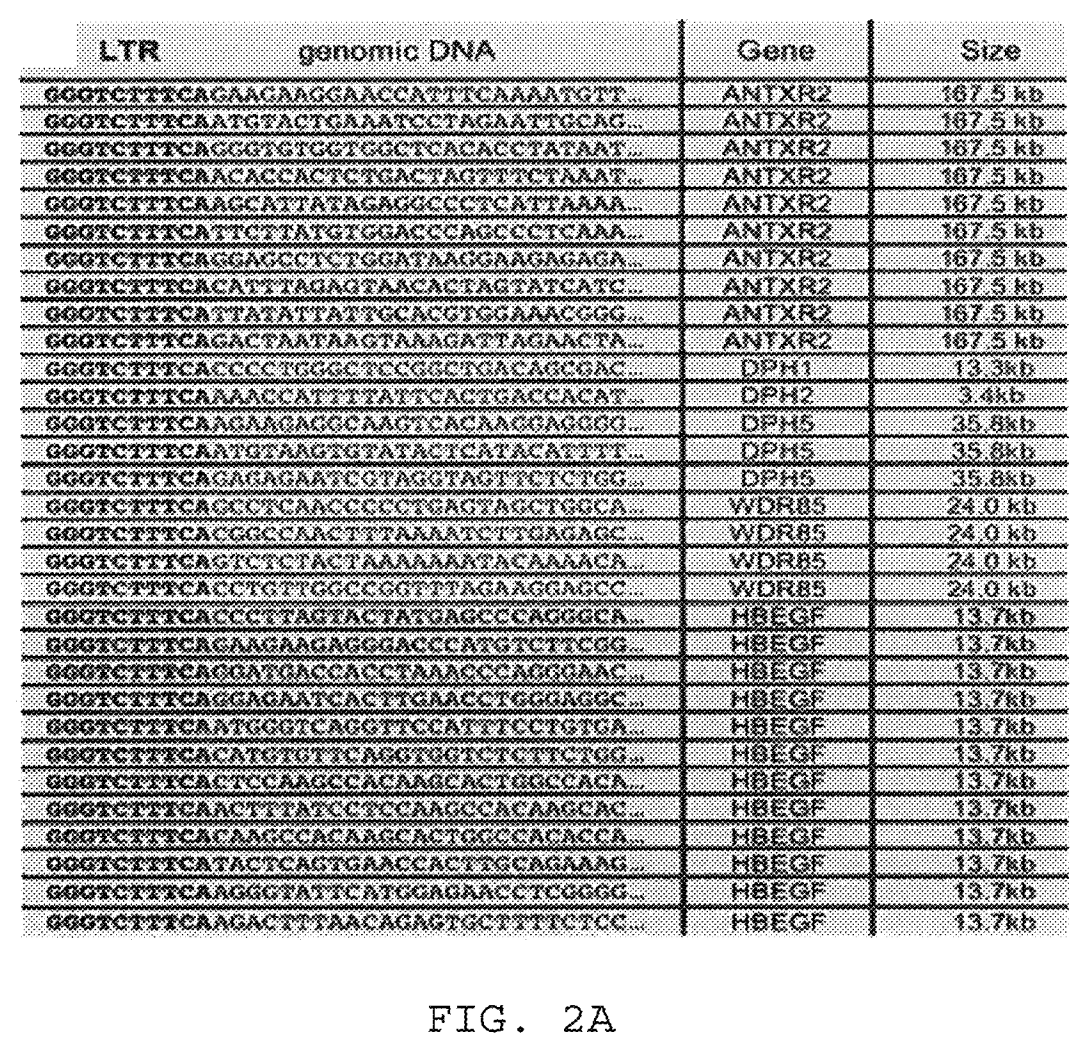

FIG. 2A illustrates gene-trap integration sites (SEQ ID NOS: 1-31, respectively) in mutant cells that are resistant to Diphtheria and Antrax-LF-DT toxin. Integrations in ANTXR2 (Blue) were resistant to Anthrax-LF-DT only, integrations indicated in green were resistant to both Diphtheria and Anthrax-LF-DT toxins and integrations indicated in pink were only resistant to Diphtheria toxins. Positions of integration sites in the respective gene loci are schematically indicated by a red line in the right panel. All gene-trap integrations were in the sense orientation.

FIG. 3A illustrates that cytolethal distending toxin causes a characteristic accumulation of cells in the G2/M phase of the cell cycle. Resistant clones contain gene trap integrations in SGMS1 and TMEM181 (SEQ ID NOS: 32-44, respectively).

FIG. 8A shows 24-color spectral karyotype of near-haploid KBM-7 cells and schematic outline of gene trap mutagenesis screens. FIG. 8B shows gene trap insertion sites (SEQ ID NOS: 51-69, respectively) in cells exposed to 6-thioguanine, TRAIL or Gleevec (left panel). Schematic outline of the insertion sites (right panel) indicates that all gene trap insertions are predicted to interrupt the coding sequences of the trapped genes (gray boxes).

FIG. 8C shows an immunoblot analysis of FADD, Caspase-8, NF1, and HPRT expression levels in clones that contain independent gene trap insertions in the respective loci. CDK4 was used as a loading control. FIG. 8D is a phase-contrast picture of wild type, caspase-8 and FADD gene trap cells treated with TRAIL.

FIG. 9A shows flow cytometric analysis of control KBM-7 cells (left) and KBM-7 cells after exposure to CDT purified from *E. coli* (right panel). Exposure of cells to CDT results in an increase of cells in the G2/M phase of the cell cycle (see arrow A) and cell death (see arrow B). FIG. 9B shows insertion site (SEQ ID NOS: 70-83, respectively) analysis in mutant cells unresponsive to CDT (upper panel)

and schematic outline of the insertion sites in the affected loci. FIG. 9C illustrates CDT resistance of TMEM181 mutant cells and SGMS1 mutant cells to CDT. Mutant cells reconstituted with the respective cDNAs re-acquire toxin sensitivity. FIG. 9D shows immunoblot analysis of cell lysates from control and HA-TMEM181 expressing cells that were incubated with immobilized anti-Flag antibodies in the presence or absence of Flag-CDT. Bound proteins were detected by immunoblot analysis. As shown in FIG. 9E, NIH3T3, U2OS and HELA cells infected with a TMEM181 expressing retrovirus were treated with increasing amounts of CDT. After 5 days viable cells were stained with crystal violet. FIG. 9F shows a putative model for cell entry and intoxication by *E. coli* CDT.

FIG. 10A shows an analysis of insertion sites (SEQ ID NOS: 84-88, respectively) in cells resistant to influenza virus (right panel). Schematic outline of the identified insertion sites indicates that they interrupt the coding sequence of the affected genes (gray boxes). As shown in FIG. 10B, cells were exposed to influenza virus and stained 12 hours later using antibodies directed against influenza A nucleoprotein. Mutant cells reconstituted with cDNAs that correspond to the mutated gene products re-acquire virus sensitivity.

*charomyces cerevisiae* YBR246W (SEQ ID NO: 123). FIG. 19B lists the ten most significant fitness defects specific for YBR246W homozygous yeast cells out of 1144 different conditions. FIG. 19C lists the yeast mutants that most significantly phenocluster with YBR246W and the enriched GO terms for the interacting genes. Data was obtained using the yeast fitness database (http://fitdb.stanford.edu/; web supplement from (M. E. Hillenmeyer et al., *Science* 320:362 (Apr. 18, 2008))).

DETAILED DESCRIPTION OF CERTAIN EMBODIMENTS OF THE INVENTION

Figures 2B, 2C:
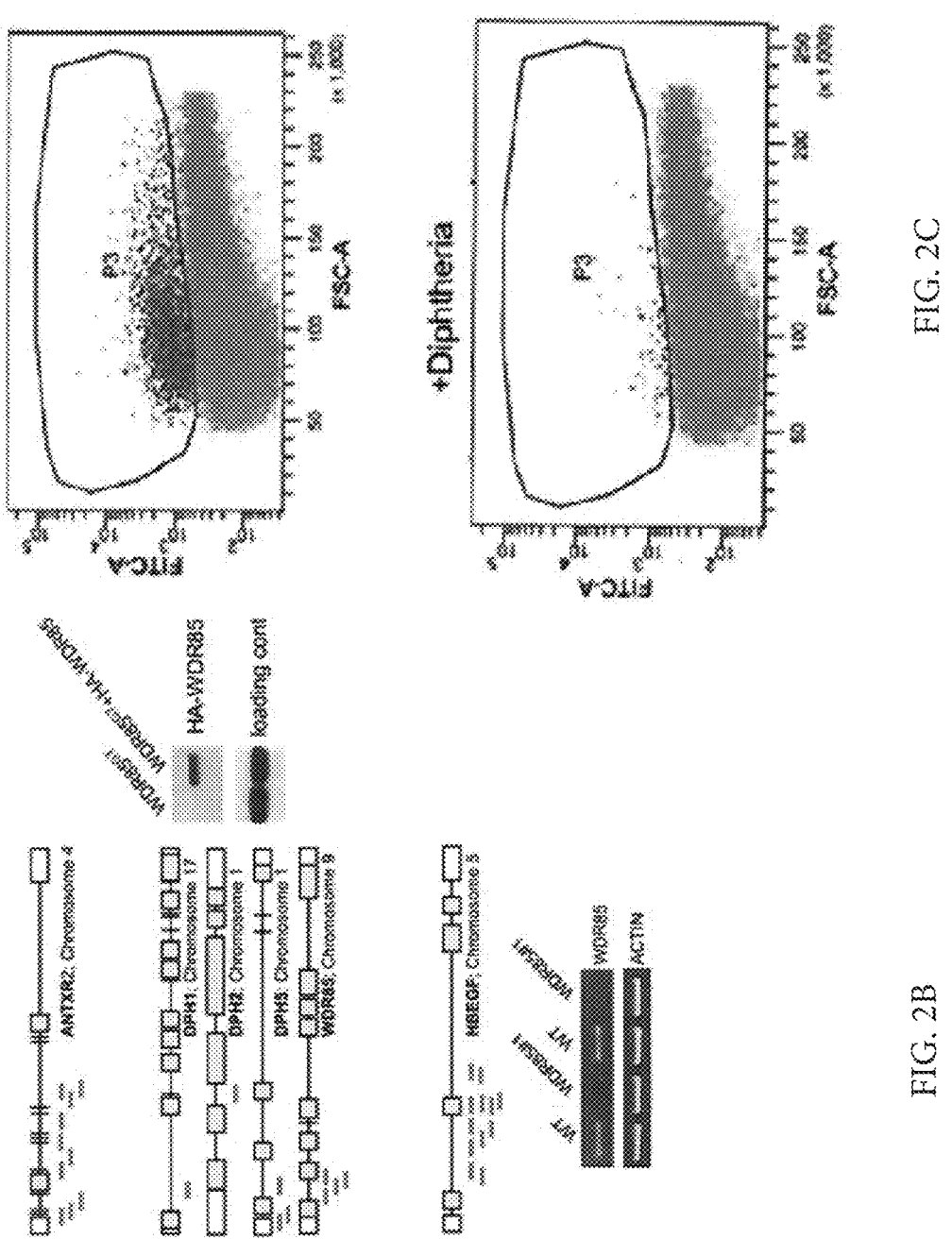
FIG. 2B illustrates add back of WDR85 cDNA in cells that contain a gene trap in the respective locus.
FIG. 2C demonstrates that cells expressing WDR85-ires-GFP (upper panel) become selectively killed when treated with Diphtheria toxin (lower panel).

The present invention relates to new approaches for performing mammalian cell genetics and/or to mammalian cells, nucleic acid constructs, and compositions of use in performing genetic screens in mammalian cells. In some aspects, the invention relates to novel methods of performing genetic screens using gene trap vectors in mammalian cells. Gene trap mutagenesis has been employed to produce gene trap alleles for a number of mouse genes in ES cells (Nord, A S, et al., The International Gene Trap Consortium Website: a portal to all publicly available gene trap cell lines in mouse Nucleic Acids Research Vol. 34, Database issue D642-D648, 2006). The resulting cells are typically used to generate mice that are homozygous for the mutant allele. By analyzing the phenotype of these mice one may gain insight into the function of the disrupted gene. However, this approach is time-consuming and does not lend itself to approaches that seek to identify genes that affect particular cell phenotypes or biological pathways of interest. The invention encompasses the discovery that gene trap vectors can be used to effectively identify genes that affect mammalian cell phenotypes of interest in haploid or near-haploid mammalian cells. The inventive approach does not require generating a non-human mammal homozygous for the mutant allele. Instead, cells can be directly screened to identify those bearing a mutation in a gene that affects cell phenotype.

The invention provides methods of performing forward genetic screens in mammalian cells, i.e., screens that involve providing a population of mutant cells and detecting a cell having a particular phenotype of interest, followed by identification of gene(s) that affect the phenotype. Certain of the methods comprise steps of: (a) introducing a gene trap vector into near-haploid mammalian cells in culture, wherein said gene trap vector integrates into the genome of said near-haploid mammalian cell, and wherein the gene trap vector comprises a nucleic acid that allows the identification of a cell containing said nucleic acid; (b) identifying a cell containing said gene trap vector integrated into its genome, wherein the cell exhibits a phenotype of interest; and (c) identifying a gene into which the gene trap vector integrated, thereby identifying a gene that affects cell phenotype. The invention also provides compositions useful for performing the inventive methods.

Gene Trap Vectors

The term "gene trap vector" refers to a vector that comprises a nucleic acid construct capable of inserting into and potentially inactivating an endogenous cellular gene. Typically, insertion of the nucleic construct into the gene both disrupts the gene and facilitates its identification. A cell having such an insertion may be referred to as a "mutant cell". The inserted DNA serves as a "molecular tag", which can be used to isolate or otherwise identify endogenous genomic DNA located nearby, as discussed further below. The nucleic acid construct often comprises DNA that encodes a reporter that, when expressed, allows identification of a cell that contains the construct inserted into its genome. The construct typically lacks a genetic element, such as a promoter or a polyadenylation (polyA) sequence, that is normally required for or significantly increases expression, so that effective expression of the reporter following introduction of the vector into a cell occurs only if the construct inserts into an endogenous gene.

Figures 1A, 1B, 1C:
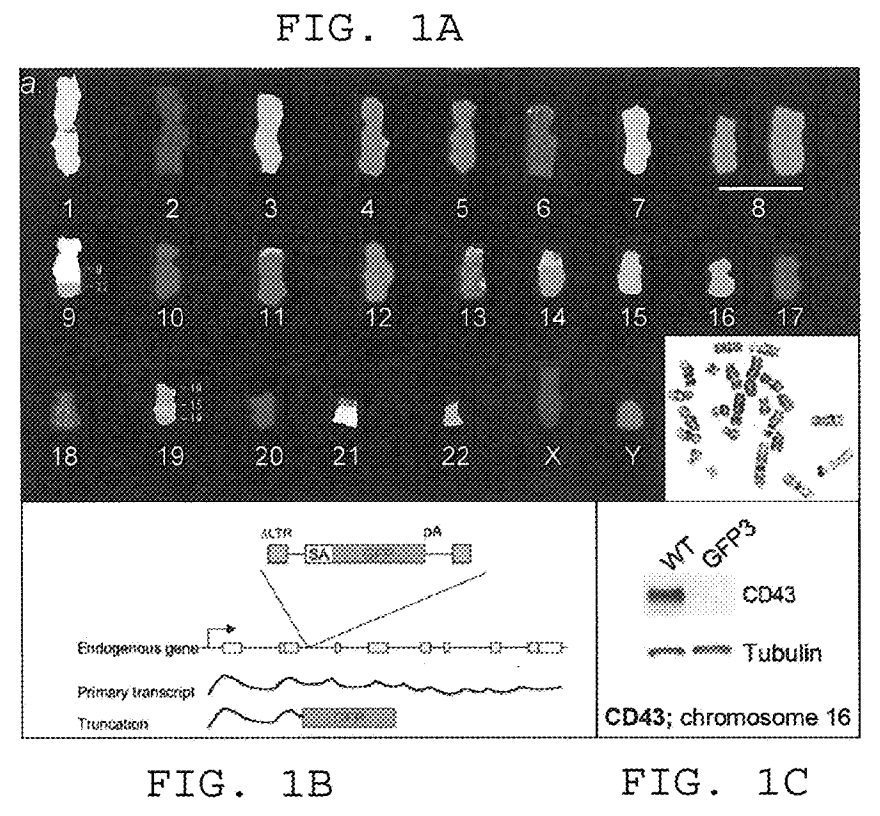

Gene trap vectors of a variety of different designs may be used in various embodiments of the invention. In some embodiments of the invention the gene trap vector comprises a nucleic acid construct comprising a promoterless reporter gene flanked by an upstream splice acceptor (SA) site and a downstream polyadenylation sequence. In other words, the promoterless reporter gene is positioned downstream from a splice acceptor site and upstream from a polyA sequence (also referred to as a "polyA site" or "polyA signal". FIG. 1B shows an exemplary promoterless gene trap construct in schematic form, wherein the reporter gene encodes green fluorescent protein (GFP). When inserted into an intron of an expressed gene, the gene trap construct is transcribed from the endogenous promoter of that gene in the form of a fusion transcript in which the exon(s) upstream of the insertion site is spliced in frame to the reporter/selectable marker gene. Transcription terminates prematurely at the inserted polyadenylation site, so that the resulting fusion transcript encodes a truncated and non-functional version of the cellular protein fused to the reporter. The reporter allows identification of cells in which the gene trap vector has inserted into an actively transcribed locus. Thus, these gene trap vectors both inactivate and report the expression of the trapped gene at the insertion site and provide a nucleic acid tag that permits rapid identification of the disrupted gene. A variety of splice acceptor sites can be used in the gene trap vector. In some embodiments of the invention the SA site is an adenoviral SA site. In some embodiments a SA from the long fiber gene of adenovirus type 40 is used (Carette et al. 2005 The Journal of Gene Medicine 7(8) 1053-1062). Other strong adenoviral SA sites are those derived from the fiber or hexon geneof different adenoviral serotypes. A variety of polyA sequences can be used in the gene trap vector. In some embodiments of the invention the polyA sequence is a bovine growth hormone polyA signal.

In some embodiments of the invention the gene trap vector is a polyA trap vector. A polyA trap vector comprises a nucleic acid construct comprising (i) a reporter gene comprising a nucleic acid sequence that encodes a reporter, operably linked to a promoter; and (ii) a splice donor (SD) site located downstream of the reporter gene. The gene trap vector lacks a polyA sequence, so that efficient synthesis of the reporter can only occur if the vector inserts in an intron and a polyA site is provided by splicing to downstream exons. When inserted into an intron of an endogenous gene, the transcript expressed from the gene trap promoter is spliced to the downstream exons of the endogenous gene, the most 3' of which comprises a polyA sequence, resulting in a fusion transcript that terminates with the polyA sequence of the endogenous gene. Since the fusion transcript is expressed from the inserted promoter, polyA trap vectors trap genes independently of whether the endogenous gene is expressed. The reporter allows identification of cells in which the gene trap vector has inserted into an intron, and the inserted DNA can be used to identify genomic sequences close to the insertion site. In some embodiments of the invention the SD site is an adenoviral SD site. In some embodiments, a polyA trap vector further comprises an IRES sequence downstream of the termination codon of the reporter gene and upstream of the splice donor site. This approach can be useful to overcome nonsense-mediated decay that might otherwise occur, e.g., if the termination codon of the reporter gene is e.g., more than about 55 nucleotides upstream of the final splice junction site.

In some embodiments, a gene trap vector comprises a genetic element that facilitiates the selective identification of genes having a property of interest, such as genes that encode transmembrane or secreted proteins. For example, in some embodiments the gene trap vector is a secretory gene trap vector. In some embodiments the secretory gene trap vector comprises a nucleic acid construct comprising a portion that encodes a type II transmembrane (TM) domain located N-terminal to a portion that encodes a reporter, wherein the reporter has the property that its activity is significantly different (e.g., reduced) if located in the lumen of the endoplasmic reticulum (or other secretory compartment) relative to activity if not located in such lumen.

A variety of different promoters can be used in a polyA trap vector (or other gene trap vector that comprises a promoter), provided that the promoter is capable of directing expression in a near haploid mammalian cell in which the gene trap vector is used. In many embodiments the promoter is an RNA polymerase II promoter (i.e., a promoter that directs transcription by RNA polymerase II). In some embodiments the promoter is a constitutive promoter. In some embodiments the promoter is a strong promoter active in a wide range of mammalian cell types, such as the CMV immediate-early promoter or major intermediate-early promoter, or other mammalian viral promoters such as the herpes simplex virus (HSV) promoter, SV40 or other polyoma virus promoters, and adenovirus promoters. In some embodiments the promoter is a mammalian gene promoter, such as the elongation factor-1alpha (EF1alpha), phosphoglycerate kinase-1 (PGK), histone, or hTERT promoter. In some embodiments the promoter is active in one or more cell types or cell lineages of interest and is not active, or is substantially less active, in many or most other cell types or lineages. For example, if the near-haploid mammalian cell is a hematopoietic cell, a promoter active in hematopoietic lineage cells may be used. In some embodiments the promoter is regulatable, e.g., inducible. Examples of regulatable promoters include heat shock promoters, metallothionein promoter, and promoters that comprise an element responsive to a small molecule such as tetracycline or a related compound (e.g., doxycycline), or a hormone. For example, inducible promoters can comprise a tetracycline-regulatable element or a hormone response element that renders the promoter responsive to a ligand for a hormone receptor. Exemplary receptors include the estrogen, progesterone, and glucocorticoid receptors. Exemplary ligands include physiological ligands, e.g., estrogen, progesterone, or cortisol, and non-physiological ligands, e.g., tamoxifen, dexamethasone. It will be understood that the cell should express the appropriate trans-acting proteins typically comprising a DNA binding domain, activation or repression domain, and ligand-binding domain.

In some embodiments a gene trap vector comprises first and second nucleic acid constructs that contain first and second reporter genes, respectively. The reporter genes are typically different. The first nucleic acid construct comprises a reporter gene operably linked to a promoter active in a near-haploid mammalian cell of interest. The other nucleic acid construct comprises a promoterless gene trap construct or a polyA trap construct such as those described above. A reporter encoded by the first reporter gene is used to identify cells in which the gene trap vector has integrated into the genome. A reporter encoded by the second reporter gene is used to identify cells in which such integration occurs in an endogenous gene. In some embodiments a first reporter gene encodes a selectable marker and a second reporter gene encodes a detectable marker.

Gene trap constructs may be made using standard methods of recombinant DNA technology and genetic engineering and can be introduced into cells using various types of vectors. In certain embodiments of the invention the gene trap vector is a viral vector, e.g., a retroviral (e.g., lentiviral), adenoviral, or herpes viral vector that comprises the gene trap construct, e.g., as part of its genome. The viral vector can be a virus (viral particle), which is used to infect cells, thereby introducing the gene trap construct. Following infection, at least a portion of the viral genome or a copy thereof integrates into the cellular genome, typically at random sites within the cell's DNA. In certain embodiments of particular interest, a retroviral vector is employed to deliver the gene trap construct to a near-haploid mammalian cell. Retroviral vectors and methods of using retroviruses to introduce exogenous DNA into mammalian cells are well known in the art. A retroviral vector typically comprises LTRs, which can be derived from various types of retroviruses. The LTR(s) may be genetically modified to provide desired properties, and the viral genome can be modified, e.g., to lack promoter activities and/or to comprise regulatory elements suitable for propagation and selection in bacteria, such as an origin of replication and an antibiotic resistance marker. The gene trap construct is positioned between the LTRs. Infectious, replication-competent retroviral gene-trap particles can be produced by transfecting a retroviral plasmid comprising the gene trap construct into a retrovirus packaging cell line using standard methods. The cells are cultured and viral particles released into the media are collected (e.g., as supernatants) and used to infect mammalian hear-haploid cells. In some embodiments the ratio of cells to particles is kept relatively low, e.g., below about 0.25, to reduce the likelihood of multiple integrations.

In some embodiments of the invention the gene trap vector is a plasmid, which is used to introduce the gene trap construct into near-haploid mammalian cells.

Reporters and Reporter Genes

The term "reporter" often refers to an RNA or protein that, when expressed by a cell, can be used to distinguish or separate the cell from otherwise similar cells that do not express the RNA or protein or can be used to distinguish or separate the cells from other cells that express the RNA or protein at different levels or in which the RNA or protein has a lower or higher activity. The term "reporter gene" refers to a nucleic acid that encodes a reporter. Often, a reporter gene comprises DNA that is transcribed to mRNA that is translated by the cell to produce a protein. The protein has a property that allows the cell to be distinguished or separated from cells that do not produce the protein.

A variety of different reporters are of use in various embodiments of the invention. In some embodiments, the reporter comprises a selectable marker. As used herein, the term "selectable marker" refers to a reporter that, when expressed by a cell, confers on the cell a proliferation or survival advantage under at least some conditions ("selective conditions"), relative to otherwise similar cells not expressing the reporter. Selectable markers that confer a proliferation or survival advantage and methods of selecting cells based on expression of such markers are known in the art. Examples of selectable markers include proteins that confer resistance to various drugs ("drug resistance markers"). Selective conditions for drug resistance markers typically comprise culturing cells in media that contains the relevant drug in concentrations sufficient to significantly reduce cell viability and/or proliferation. One of skill in the art will be aware of appropriate concentrations. Optimum concentrations for any particular cell type or cell line can be readily determined. Examples of drug resistance markers include enzymes conferring resistance to various aminoglycoside antibiotics such as G418 and neomycin (e.g., an aminoglycoside 3'-phosphotransferase, 3' APH II, also known as neomycin phosphotransferase II (nptII or "neo")), Zeocin™ or bleomycin (e.g., the protein encoded by the ble gene from *Streptoalloteichus hindustanus*), hygromycin (e.g., hygromycin resistance gene, hph, from *Streptomyces hygroscopicus* or from a plasmid isolated from *Escherichia coli* or *Klebsiella pneumoniae*, which codes for a kinase (hygromycin phosphotransferase, HPT) that inactivates Hygromycin B through phosphorylation), puromycin (e.g., the *Streptomyces alboniger* puromycin-N-acetyl-transferase (pac) gene), or blasticidin (e.g., an acetyl transferase encoded by the bls gene from *Streptoverticillum* sp. JCM 4673, or a deaminase encoded by a gene such as bsr, from *Bacillus cereus* or the BSD resistance gene from *Aspergillus terreus*). Other exemplary drug resistance markers are dihydrofolate reductase (DHFR), adenosine deaminase (ADA), thymidine kinase (TK), and hypoxanthine-guanine phosphoribosyltransferase (HPRT). Proteins such as P-glycoprotein and other multidrug resistance proteins act as pumps through which various cytotoxic compounds, e.g., chemotherapeutic agents such as vinblastine and anthracyclines, are expelled from cells. (See Ambudkar S V, et al., Oncogene, 22(47): 7468-85, 2003) could also be used as selectable markers. In some embodiments the sequence of a gene encoding a reporter, e.g., a drug resistance marker, is optimized for expression in mammalian cells. In some embodiments of the invention, a drug resistance marker other than neo, such as a puromycin-N-acetyl-transferase, is used.

Proteins that function in biosynthetic pathways and confer prototrophy with respect to particular compounds required for cell viability or proliferation ("nutritional markers") may also be used as selectable markers. Selective conditions for nutritional markers often comprise culturing cells in media that lacks sufficient concentration of the relevant compound to support cell viability and/or proliferation. In general, under nonselective conditions the required compound is present in the environment or is produced by an alternative pathway in the cell. Under selective conditions, functioning of the biosynthetic pathway is needed since the cell must produce the compound. HPRT and TK are examples. Cells lacking HPRT expression (e.g., lacking a functional copy of the HPRT gene) or lacking TK expression (e.g., lacking a functional copy of the TK gene) can grow in standard culture medium but die in HAT medium, which contains aminopterin, hypoxanthine, and thymidine). In cells lacking HPRT or TK expression, HPRT or TK, respectively, can be used as a selectable marker whose presence may be selected for in HAT medium.

Culturing a population of cells under selective conditions, wherein some of the cells express a selectable marker that confers a proliferation or survival advantage and other cells do not express the selectable marker, will, in general, eventually result in a population enriched for cells that express the selectable marker. In many embodiments, most or all cells that do not express the selectable marker will be eliminated from the population after a sufficient time. The time required to eliminate a given percentage of cells not expressing the selectable marker will depend on the marker, the conditions, and the cells, and can be readily determined by the skilled artisan. It will be understood that "selective conditions" can refer to a single set of conditions or to multiple sets of conditions, which may be applied in sequence. It will also be understood that cells need not be maintained continuously under the selective conditions.

In some embodiments, the reporter allows physical separation based on presence of a cell surface molecule on cells that express it. As used herein, "cell surface molecule" (CSM) refers to a protein at least part of which is located outside the plasma membrane of a cell so that it is accessible to a specific binding agent present in the environment in which such cell is located. Examples include CD molecules, receptors with an extracellular domain, channels, and cell adhesion molecules. In many embodiments, the reporter gene encodes the CSM. Methods known in the art can be used to separate cells that express a cell surface molecule from cells that do not. A specific binding agent can be used to physically separate cells that express a CSM from cells that do not. The term "specific binding agent" refers to a molecule or molecular complex that specifically binds to another molecule. Antibodies and aptamers are exemplary specific binding agents. In some embodiments of the invention an antibody or other specific binding agent is attached to a support. The support can be, e.g., a vessel or receptacle in which cells can be placed or a population of particles, such as magnetic particles or aa, chromatography resin. Cells are contacted with the support in a liquid medium. Cells that express the marker bind to the specific binding agent and can thus be separated from cells that do not express the marker. Cells can subsequently be released from the support using standard methods. In other embodiments, flow cytometry is used to separate cells that express a CSM from cells that do not. For example, cells are contacted with a fluorescently labeled antibody that binds to the CSM. Fluorescence activated cell sorting (FACS) is then used to separate cells based on fluorescence.

In some embodiments, the reporter is or comprises a readily detectable marker, e.g., a protein that can be readily detected such as a fluorescent or luminescent protein or an enzyme that acts on a substrate to produce a colored, fluorescent, or luminescent substance. In some embodiments the readily detectable marker produces a signal or a change in a signal based on light or an interaction with light (an "optically detectable signal"), which signal can be detected e.g., visually or using suitable instrumentation. Fluorescent markers include green fluorescent protein (GFP), blue, sapphire, yellow, red, orange, and cyan fluorescent proteins and fluorescent variants such as enhanced GFP (eGFP), mCherry, etc. Luminescent proteins such as luciferase (e.g., firefly or *Renilla* luciferase) are also of use. In the case of an enzyme that acts on a substrate, cells are contacted with a cell-permeable substrate. Cells expressing the enzyme can then be distinguished from cells that do not.

Selection can be based at least in part on lack of expression of a protein. In some embodiments cells are engineered to express a CSM or a protein that is toxic or results in cytotoxicity under certain conditions (e.g., an enzyme that generates a toxic metabolite when cultured in medium containing a precursor of the metabolite). The gene encoding the CSM or toxic protein, or a portion thereof essential for function, is flanked by sites recognized by a recombinase, so that a recombination event would remove or disable the gene. The recombinase can then serve as a reporter. Cre recombinase and flp recombinase (which recognize LoxP and Frt sites, respectively) are exemplary recombinases. In yet other embodiments, a first reporter modulates, e.g., enhances or inhibits, the expression of a second reporter, e.g., a drug resistance marker, nutritional marker, CSM, or enzyme. For example, the first reporter may be a transcription factor. Cells are selected based on expression or lack of expression of the second reporter.

It will be understood that a reporter can be used for a variety of purposes other than identifying or selecting cells based on expression or activity of the reporter. For example, expression or activity of a reporter can "report on", e.g., provide information relating to, a cell process such as transcription, translation, degradation, signal transduction, protein translocation, enzyme activity, metabolism, protein-protein interaction, or any of a variety of other processes or phenotypes of interest. Such information may relate to particular genes, RNAs, proteins, or signaling pathways. The information be qualitative or, in some embodiments, quantitative.

Near-Haploid Mammalian Cells

In almost all mammals, including humans, most somatic cells that comprise the body are normally diploid, i.e., they contain two homologous copies of each chromosome (other than the two sex chromosomes, which can be either homologous or non-homologous depending on the sex and particular species). The members of a homologous pair are non-identical chromosomes that both contain the same genes at the same loci but possibly have different alleles (i.e., different genetic variants) of those genes. In contrast, a haploid cell contains only only a single copy of each chromosome. A near-haploid mammalian cell, as used herein, refers to a mammalian cell in which no more than 5 chromosomes are present in two or more copies. In some embodiments a near-haploid mammalian cell has no more than 1, 2, 3, or 4 chromosomes present in two or more copies. For purposes of convenience the term "near-haploid" cell as used herein should be understood to include haploid cells. It will be appreciated that some cells contain chromosomal translocations or fusions, wherein portions of two chromosomes are exchanged or a portion of one chromosome is fused to another chromosome. Translocations or fusions can be recognized by a number of techniques, e.g., by detecting alterations in banding pattern or by fluorescence in situ hybridization. For purposes herein, if at least half of the genetic information present on a normal chromosome, as assessed using FISH or by examining banding pattern, remains present within a cell, the chromosome is considered to be present.

In some embodiments of the invention the near-haploid mammalian cell is a human cell. In some embodiments of the invention the near-haploid mammalian cell is a non-human mammalian cell, e.g., a non-human primate cell or a rodent cell, e.g., a mouse, rat, or rabbit cell. In some embodiments of the invention the near-haploid mammalian cell is a hematopoietic lineage cell, e.g., a lymphoid or myeloid cell. In some embodiments of the invention the near-haploid mammalian cell is a tumor cell, e.g., a descendant of a cell that was originally obtained from a tumor. The tumor may be benign or malignant (a "cancer"). In some embodiments the tumor is a carcinoma, sarcoma, or hematologic malignancy, e.g., a leukemia (such as chronic or acute myelogenous leukemia, chronic or acute lymphocytic leukemia) or a lymphoma or a myeloma. In some embodiments the tumor cell is a hematopoietic tumor cell, e.g., a leukemia or lymphoma or myeloma cell. In some embodiments a near-haploid mammalian cell line is isolated, e.g., subcloned, from a population of cells comprising at least some near-haploid cells. For example, subclones can be generated from individual cells and screened, e.g., using flow cytometry, to identify subclones that have a near-haploid karyotype. In some embodiments, a near-haploid cell line is haploid except with respect to chromosome 8.

In some embodiments of particular interest the near-haploid mammalian cell is a cell of the KBM7 cell line, or a subclone thereof (see Examples). In other embodiments of the invention the near-haploid mammalian cell is a leiomyosarcoma cell (Dal Sin, P., et al., J Pathol., 185(1):112-5, 1988).

In some embodiments a near-haploid cell comprises a gene that encodes a reporter or sensor. In some embodiments the reporter or sensor is of use to identify a cell that has or does not have a phenotype of interest. In some embodiments the gene encoding the reporter is stably integrated into the genome. For example, transcriptional reporter gene could comprise a nucleic acid encoding a reporter protein wherein the nucleic acid is operably linked to a transcriptional regulatory element of interest, e.g., a promoter of interest. Activation of the promoter results in transcription of an mRNA encoding the reporter protein. Detection of the reporter protein indicates that the promoter is active, and the level of expression of the reporter protein provides an indication of the level of activity of the promoter. A variety of genetically encoded sensors are known (Deuschle, K, et al. Cytometry A. 64(1):3-9, 2005).

A variety of reporter systems known in the art could be used, e.g., employing reporters such as those described above. The activity of the reporter can be used as a readout to identify a cell having an gene trap construct insertion in a gene of interest, as described further below. It will be appreciated that a reporter or sensor used for purposes of identifying a gene that affects a phenotype of interest will often not be the same as that used for purposes of identifying cells that have the gene trap construct inserted into their genome.

The invention provides a near-haploid mammalian cell comprising a gene trap vector. The invention further provides a near-haploid mammalian cell having a gene trap construct inserted into its genome, wherein the gene trap construct disrupts a gene. In some embodiments the construct is stably integrated, so that it is inherited by daughter cells when the cell divides.

A wide variety of methods are suitable for introducing a gene trap vector into near-haploid mammalian cells. Examples include viral infection (e.g., retroviral infection), tranfection (e.g., using calcium-phosphate or lipid-based transfection reagents), electroporation, microinjection, etc. One of skill in the art can select an appropriate method based, e.g., on the nature of the vector and cell. In some embodiments, a plasmid gene trap vector is linearized prior to introducing it into cells. It will be appreciated that not all cells contacted with a gene trap vector will take up the vector, and not all cells that take up the vector will result in stable insertion of the construct into the genome. In some embodiments, after contacting cells with a gene trap vector under conditions suitable for uptake and insertion of the construct, cells that have taken up and, in some embodiments have the construct inserted into their genome, are identified or selected based on the reporter. For example, cells can be subjected to sorting or are cultured under selective conditions so as to eliminate at least, e.g., 95%, 98%, 99%, 99.9%, or more of the cells that do not express a reporter.

The invention provides collections ("libraries") of near-haploid mammalian cells, wherein at least some of the cells comprise a gene trap construct as described herein integrated into their genome. The libraries may be produced by (a) introducing (e.g., by infecting, transfecting, electroporating, etc.) a gene trap vector into a population of near-haploid mammalian cells (e.g., a population of largely or essentially genetically identical near-haploid cells, such as a subclone derived from a single cell), wherein a gene trap construct becomes stably inserted into the genome of a at least some of the cells; and (b) identifying or selecting for cells that comprise the gene trap construct, e.g., cells that have the gene trap construct stably integrated into their genome. Typically, the libraries comprise multiple cells at least some of which have a gene trap construct integrated at a different site in their genomes, i.e., so that the library collectively comprises cells in which a plurality of different genes are inactivated. In some embodiments of the invention, individual cells in the library are isolated and clonally expanded. If desired, the isolated and clonally expanded genetically altered cells can be analyzed to identify genomic sequences that flank the integrated construct as discussed further below. In some embodiments the library of near-haploid mammalian cells comprises at least 100, at least 1,000, at least 5,000, at least 10,000, at least 25,000, at least 50,000, at least 100,000, at least 500,000 cells or more. In some embodiments the library comprises cells that collectively have insertions in at least 50%, at least 75%, at least 90%, at least 95%, or about 100% of the genes present in cells of that species.

Gene Identification and Genetic Screens

The invention provides methods for performing genetic screens in near-haploid mammalian cells. In some aspects, the methods provide a way to identify a gene that affects cell phenotype. According to some of the inventive methods, a gene trap vector comprising a gene trap construct is introduced into near-haploid mammalian cells. In some embodiments, cells that have taken up the vector and have the gene trap construct inserted into their genome are identified. In some embodiments, cells in which the insertion has occurred into a gene, e.g., an actively transcribed gene (rather than in an integenic region) are identified. One or more cells having a phenotype of interest is/are identified. In some embodiments cells are manipulated or subjected to a process such as being contacted with an agent, e.g., a pathogen or compound or being exposed to a condition, and cells that exhibit a particular phenotype following such manipulation or process are identified. Genomic sequences flanking or near the site of insertion of the construct are identified. For example, they may be cloned and sequenced. The gene into which the construct inserted is identified, e.g., by comparing the sequence with a genome database. Because disrupting the gene results in the phenotype of interest, it can be inferred that the gene affects the phenotype.

In some embodiments the invention provides a method of identifying a gene that affects cell phenotype, the method comprising steps of: (a) introducing a gene trap vector into near-haploid mammalian cells in culture, wherein said gene trap vector comprises a nucleic acid construct that integrates into the genome of said near-haploid mammalian cell, and wherein the nucleic acid construct comprises a nucleic acid that allows the identification of a cell containing said nucleic acid; (b) identifying a cell containing said gene trap vector integrated into its genome, wherein the cell exhibits a phenotype of interest; and (c) identifying a gene into which the nucleic acid construct integrated, thereby identifying a gene that affects cell phenotype.

A variety of methods can be used to identify genes into which a gene trap vector has inserted. In some embodiments inverse PCR is used to identify genomic sequences flanking the insertion (see, e.g., Examples). In some embodiments splinkerette PCR is used (Horn, C., et al., Nat. Genet., 39:

807-8, 2007). In some embodiments 5'-RACE (rapid amplification of cDNA ends) is used to amplify cellular sequences contained in a gene-trap fusion transcript (see, e.g., Nature Methods, 2(8), 2005). See also Stanford, W., et al. Methods in Enzymology, Vol. 420, 2006).

Once the DNA is amplified it can be cloned into a vector and/or sequenced. The DNA can be used as a probe to identify further sequences located nearby in the genome, e.g., by probing a cDNA or genomic library. The sequence can be used to search sequence databases, e.g., publicly available databases such as Entrez, GenBank, etc., available at the National Center for Biotechnology Information website (http://www.ncbi.nlm.nih.gov/). Since the human genome is completely sequenced it will generally be possible to readily identify most genes based on a relatively small amount of partial sequence data. In some embodiments, the sequences flanking the insertion are recovered and sequenced from large populations of cells simultaneously using "high throughput" or "massively parallel" sequencing. Such sequencing techniques can comprise sequencing by synthesis (e.g., using Solexa technology), sequencing by ligation (e.g., using SOLiD technology from Applied Biosystems), 454 technology, or pyrosequencing. In some embodiments thousands, tens of thousands or more sequencing reactions are performed in parallel, generating millions or even billions of bases of DNA sequence per "run". See, e.g., Shendure J & Ji H. *Nat Biotechnol.*, 26(10):1135-45, 2008, for a non-limiting discussion of some of these technologies. It will be appreciated that sequencing technologies are evolving and improving rapidly. In some embodiments massively parallel sequencing by synthesis is used. The pools or populations of cells could be selected for a phenotype of interest and genomic regions that are enriched for insertions are identified. Such regions contain candidate genetic elements, e.g., genes, involved in the phenotype studied. Without wishing to be bound by any theory, such approaches, in which large numbers (e.g., 10,000 or more, e.g., between 10,000 and 100,000; 10,000 and 500,000; or between 10,000 and 1 million, 5 million, 10 million, 20 million, 50 million, 100 million, or more. Insertions are analyzed may help recover genes and genetic elements into which the frequency of insertion is relatively low compared with the frequency of insertion into at least some other genes or genetic regions that affect the phenotype and may facilitate performing saturation screens. Methods for simultaneous identification of multiple insertion sites using high throughput or massively parallel sequencing techniques are an aspect of the invention.

The inventive genetic screens can be applied to identify genes affecting a wide variety of cell phenotypes. For example, in some embodiments the invention provides a method of identifying host factors used by pathogens such as viruses or specific bacterial toxins or cell components needed for the response to therapeutic agents or execution of programmed cell death. In some embodiments, a screen is applied to any phenotype that can be recognized in a population of mutant cells, e.g., a population of mutant cells generated using a gene trap vector.

The invention provides a method of identifying a mammalian gene that affects susceptibility of a mammalian cell to infection by a microorganism, which term is used herein to encompass viruses, bacteria, fungi, and protozoa. "Infection" refers to the usually detrimental colonization of a cell or multicellular organism (sometimes such cell or multicellular organism is referred to as a "host") by a microorganism and encompasses entry of the microorganism into the cell (invasion) or into at least some cells of a multicellular organism and the resulting effects of the micoorganism on the host. In some embodiments of interest the microorganism is a pathogen, i.e., it is at least in part responsible for causing a disease or undesirable clinical condition in a host, e.g., a mammalian host, e.g., a human. In most embodiments the microorganism is an intracellular pathogen, i.e., a pathogen that replicates intracellularly and/or resides intracellularly during at least part of its life or during one or more stages of its life cycle. In some embodiments the organism is one that establishes a latent or chronic infection in at least some individuals. In some embodiments the invention provides a method of identifying a gene that encodes a host cell factor that affects susceptibility to a pathogen, wherein the pathogen produces a virulence factor. In some embodiments the invention provides a method of identifying a gene that encodes a host cell factor that affects susceptibility to a virulence factor. "Susceptibility" typically refers to vulnerability or propensity to become infected by or adversely affected by a pathogen or deleterious agent. "Host cell factor" refers to a molecule produced by a host, e.g., a nucleic acid or protein. A host cell factor may be a cell surface protein, cytoplasmic protein, nuclear protein, or protein that at least in part localizes to an organelle. In some embodiments a host cell factor is an enzyme. "Virulence factor" refers to a molecule produced by a pathogen that causes or contributes to disease or that affects a host's function so to allow or promote the pathogen's survival or proliferation. In some embodiments the virulence factor is a toxin. "Toxin" refers to the subset of virulence factors that act directly on the host, e.g., they physically interact with one or more cellular nucleic acids, proteins, or structures. For example, a toxin may covalently modify, and thereby activate or inactivate, a cellular protein resulting in deleterious effect on the cell. In some embodiments a virulence factor is a toxin produced by a pathogen that does not reside intracellularly during at least part of its life cycle. For example, during infection of a multicellular host, the toxin may be secreted by the pathogen and subsequently contact cells of the host. Such toxins are often referred to as "exotoxins". The toxin may interact with cell surface molecules and/or be taken up by the cells and act intracellularly. In some embodiments the toxin is secreted in inactive form by a pathogen and is processed (e.g., cleaved) or otherwise activated to a toxic form in the multicellular organism, e.g., intracellularly.

A number of bacterial exotoxins are of interest. For example, exotoxins produced by pathogenic *E. coli* play a major role in a number of serious illnesses ranging from food poisoning to toxic shock syndrome. Anthrax toxin is a major virulence factor of the spore-forming bacterium *Bacillus anthracis* and is largely responsible for some of the potentially lethal symptoms associated with the disease anthrax. Other toxins of interest include, e.g., diphtheria toxin, *Pseudomonas* exotoxin, and Panton-Valentine leukocidin (PVL). PVL is a cytotoxin and is one of the beta-pore forming toxins. The presence of PVL is associated with increased virulence of certain strains (isolates) of *Staphylococcus aureus*. It is present in the majority of community-associated Methicillin-resistant *Staphylococcus aureus* (CA-MRSA) isolates studied and is the cause of necrotic ("flesh-eating") lesions involving the skin or mucosa, including necrotic hemorrhagic pneumonia.

In some embodiments the toxin is produced by a multicellular organism. The multicellular organism may be a plant or an animal. The animal may be a vertebrate or invertebrate. In some embodiments the animal is an arthropod. In some embodiments the animal is a reptile or amphibian. In some embodiments the animal is an arachnid. In some embodiments the animal is an annelid. For example, toxins or venoms produced by snakes, insects, plants, fish, jellyfish, worms, spiders, scorpions, shellfish, or snails (e.g., cone snails) are of interest. In some embodiments the toxin is a marine or freshwater toxin, which term refers to a toxin produced by certain aquatic microorganisms such as phytoplankton and blue-green algae. In some embodiments the toxin is produced by a fungus, e.g., a mushroom. In certain embodiments the toxin is produced by a plant. For example, the $AB_1$ toxin family includes certain type II ribosome inactivating plant toxins such as ricin, abrin, cinnanomin, viscumin, ebulin, and nigrin b (Hartley, M R & Lord, J M, Cytotoxic ribosome-inactivating lectins from plants, Biochim Biophys Acta, 1701(1-2):1-14, 2004; Xu H, et al., Cinnamomin—a versatile type II ribosome-inactivating protein. Acta Biochim Biophys Sin (Shanghai) 36(3):169-76).

Further information regarding certain toxins discussed herein and many others may be found in the following references: Alouf, J E & Popoff, M R, (eds.) The Comprehensive Sourcebook of Bacterial Protein Toxins, Third Edition, Academic Press, 2006; Schmitt, MJ & Schaffrath, R (eds.) Microbial Protein Toxins, Topics in Current Genetics 11, Berlin, New York: Springer-Verlag, 2005; Proft, T. (ed.) Microbial toxins: molecular and cellular biology, Norfolk, England: BIOS Scientific, c2005.

In some embodiments the method comprises steps of: (a) introducing a gene trap vector into near-haploid mammalian cells, wherein the gene trap vector comprises a nucleic acid construct comprising a nucleic acid encoding a reporter that allows the identification of a cell expressing said nucleic acid, wherein said nucleic acid construct integrates into the genome of said haploid mammalian cell; (b) contacting the near-haploid mammalian cells with a pathogen or virulence factor (e.g., a toxin); (c) identifying a cell that contains said nucleic acid construct integrated into its genome and exhibits altered susceptibility to the pathogen or virulence factor; and (c) identifying a gene into which the nucleic acid construct integrated, thereby identifying a gene that encodes a host cell factor that affects susceptibility to a pathogen or virulence factor. It will be understood that a host cell factor that affects susceptibility is also considered a host cell factor that affects "resistance", e.g., ability to withstand or not be significantly adversely affected by a pathogen or potentially deleterious agent. The genes identified in the inventive screens may be genes that, when mutated, confer on a cell resistance to a pathogen or virulence factor (or other deleterious agent).

An inventive screen may be used to identify genes and/or host factors that affect susceptibility to a wide variety of pathogens or virulence factors produced by such pathogens. Viruses of interest include, e.g., single or double stranded DNA or RNA viruses, retroviruses, etc. They may belong, e.g., to the following families Adenoviridae, Picornaviridae, Herpesviridae, Hepadnaviridae, Flaviviridae, Retroviridae, Orthomyxoviridae, Paramyxoviridae, Papovaviridae, Rhabdoviridae, Reoviridae, Togaviridae. Specific examples are HBV, HCV, HIV, EBV, CMV, influenza virus, measles virus, rabies virus, Ebola virus, Marburg virus, and yellow fever virus. Non-limiting examples of viruses and information regarding them is found, e.g., in Knipe, D M and Howley, P M (eds.) Fields Virology, Volumes I and II. 5th ed. Lippincott Williams and Wilkins, 2007; Büchen-Osmond, C. (Ed), (2006) Index to ICTVdB virus descriptions. In: ICTVdB—The Universal Virus Database, version 4. ICTVdB Management, Mailman School of Public Health, Columbia University, New York, NY, USA; and "ICTVdB—The Universal Virus Database", version 4, April 2006. http://www.ictvdb.org/Ictv/ICTVindex.htm) and ICTVdb Virus Descriptions (http://www.ictvdb.org/ICTVdB/index.htm). (It is noted that the online database is currently being rewritten.) The most recent report of the International Committee on the Taxonomy of Viruses (ICTV) of the International Union of Microbiological Societies: "Virus Taxonomy: VIIIth Report of the International Committee on Taxonomy of Viruses", 2005, C. M. Fauquet, M. A. Mayo, J. Maniloff, U. Desselberger, and L. A. Ball (Eds), Elsevier Academic Press, is considered the standard and definitive reference for virus taxonomy (classification and nomenclature), as supplemented by taxonomic proposals subsequently approved by the ICTV (available as updates on the ICTV website as http://talk.ictvonline.org/media/22/default.aspx/. http://talk.ictvonline.org/files/ictv_official_taxonomy_updates_since_the_8th_report/default.aspx). Bacteria of interest include, e.g., gram positive bacteria, gram negative bacteria, acid fast bacteria, etc. Examples are Mycobacteria, e.g, *M. tuberculosis, Chlamydia*, e.g., *C. trachomatis, Staphylococcus, Streptococcus, Pseudomonas*, Enterococci, Enterobacteriaceae (*Klebsiella, Salmonella, Serratia, Yersinia*), Erysipelothrix, *Helicobacter, Legionella, Leptospires, Listeria, Mycoplasmatales, Neisseriaceae* (e.g., *Acinetobacter, Menigococci*), Pasteurellacea (e.g., *Actinobacillus, Heamophilus, Pasteurella*), *Rickettsia*, Bacillaceae (e.g., Anthrax, *Clostridium*), Bacteroidaceae, Corynebacteria, Cyanobacteria, etc. Fungi of interest include *Cryptococcus, Coccidia, Histoplasma, Candida, Aspergillus, Blastomyces*, etc. Parasites of interest include, e.g., Apicomplexans such as *Toxoplasma, Cryptosporidium*, or *Plasmodium*; kinetoplastids such as Trypanosomes, etc. Non-limiting examples of bacteria, fungi, parasites, viruses, and information regarding them is found, e.g., in B. Forbes, et al., ed., Bailey & Scott's Diagnostic Microbiology 12th ed., Elsevier/Mosby, 2007 and/or in Garcia, L., Diagnostic Medical Parasitology ASM Press; 5 edition, 2006. One of skill in the art will readily be able to obtain infectious agents for use in inventive screens. For example, many such agents may be obtained from American Type Culture Collection (ATCC), the culture collections of the Health Protection Agency of the UK, and/or numerous other depositories, collections, and laboratories worldwide. Further, it is noted that recombinant, modified, or pseudotyped versions of naturally occurring pathogens may be used in the methods of the invention. Such versions may have reduced or increased virulence relative to a naturally occurring strain or have an altered host range.

In some embodiments, infection of a mammalian cell by the pathogen or contacting the cell with a virulence factor results in cytotoxicity or significant reduction in cell proliferation. In such instances, in some embodiments, near-haploid mammalian cells, at least some of which have the gene trap construct integrated into their genome, are contacted with the pathogen under conditions suitable for the pathogen to enter the cells and establish an infection (i.e., conditions under which non-genetically modified cells would be expected to become infected by the organism). Cells that survive such infection and/or that proliferate are identified, and the gene(s) into which the gene trap construct integrated in such cells is identified. Such genes affect susceptibility to infection and are candidates for being host genes involved in one or more processes necessary for the pathogen to invade, survive intracellularly, replicate, and/or exert a detrimental effect. For example, such genes could encode cell surface receptors or other cellular genes that are required for, or that promote, invasion of the cell by the pathogen. Such genes could encode cellular proteins, e.g., enzymes, that are required for or promote replication, assembly, or release of the pathogen from the cell (which may result in cell lysis).

In some embodiments, near-haploid mammalian cells, at least some of which have the gene trap construct integrated into their genome, are contacted with a virulence factor under conditions in which non-genetically modified cells would be expected to exhibit toxic effects. Cells that survive such contact and/or that proliferate following or during such contact are identified, and the gene(s) into which the gene trap construct integrated in such cells is identified. Such genes affect susceptibility to the virulence factor and are candidates for being host genes involved in one or more processes necessary for the virulence factor to interact with or enter cells and/or exert a detrimental effect. For example, such genes could encode cell surface receptors or other cellular genes that are required for, or that promote, intoxication, e.g., that are required for or promote entry of the virulence factor into the cell (internalization) or transport of the virulence factor to its site of activity in the cell. Such genes could encode cellular proteins, e.g., enzymes, that are required activating an inactive virulence factor to a toxic form. Such genes could encode the direct cellular target of the virulence factor, i.e., a cellular molecule with which the virulence factor physically interacts (e.g., by covalently modifying it), in a manner that results in deleterious effects.

Toxins, virulence factors, or other agents may be produced or obtained using methods known in the art. In some embodiments the toxin, virulence factor, or agent is isolated from an organism that naturally produces it. In some embodiments an inventive screen is performed using a recombinantly produced toxin (or other virulence factor or agent). In some embodiments a chimeric toxin (e.g., a toxin that includes subunits derived from different toxins) is used. For example, an AB toxin (e.g, an $AB_5$ toxin) could have an A subunit derived from a first bacterial species and a B subunit derived from a second bacterial species. In some embodiments the toxin is "activated" in vitro before contacting the near-haploid cells. For example, the toxin may be subjected to cleavage or other processing in vitro prior to contacting the cells. In some embodiments, a holotoxin is used. In some embodiments, e.g., if a toxin is a multiple subunit toxin, it is sufficient to use only a cytotoxic portion of the toxin in performing a screen. In other embodiments, e.g., if a toxin is a multiple subunit toxin, a subunit other than the cytotoxic portion of the toxin is used. In some embodiments a genetically engineered mutant toxin, which may have altered (e.g., greater or lesser) toxicity than the wild type version, is used.

In some embodiments a pathogen or virulence factor of interest does not cause cytotoxicity or significant growth inhibition, at least in the near-haploid mammalian cell used for performing the screen. In such embodiments a variety of approaches may be taken to identify cells that have altered susceptibility to the pathogen or virulence factor. In some embodiments the pathogen or virulence factor is modified so as to render it cytotoxic to the near-haploid mammalian cell. For example, a non-cytotoxic intracellular pathogen can be genetically modified so that it produces a product that is toxic to cells. For example, a virus can be engineered to produce a bacterial exotoxin. A non-cytotoxic virulence factor can be modified to a more toxic version. For example, a non-cytotoxic bacterial exotoxin can be fused to a cytotoxic moiety, e.g., a cytotoxic bacterial exotoxin, thus resulting in a toxic version of the non-cytotoxic bacterial exotoxin (see Example 6A). Such proteins could be fusion proteins, which can be genetically encoded. In some embodiments, conjugation of the toxic moiety to the non-cytotoxic virulence factor, or synthesis of the toxic version is accomplished in vitro. In other embodiments, the near-haploid mammalian cell can be modified to as to render it susceptible to the pathogen or virulence factor. It will be appreciated that after identification of cells that have altered susceptibility and/or identification of genes that alter susceptibility, additional studies can be performed to distinguish between cells and/or genes that mediate susceptibility to the toxic moiety versus those that mediate susceptibility to the non-cytotoxic pathogen or virulence factor. In some embodiments, if the reason for lack of toxicity is known, a near-haploid cell can be genetically modified to render it susceptible. For example, if the cell lacks expression of a receptor for the pathogen or virulence factor, the cell can be genetically engineered to express such receptor. It will be appreciated that the screen may well recover at least some cells that have insertions of the gene trap construct inot the gene that encodes the receptor. However, additional genes will likely be identified as well.

In some embodiments, a genetic screen is based on a "readout" other than cytotoxicity or growth inhibition. For example, in some embodiments a virulence factor is modified so that it comprises a moiety that becomes readily detectable following cell uptake. For example, the moiety may emit an optically detectable signal following cell uptake. In some embodiments the modified virulence factor is cleaved by an intracellular protease to generate a fluorescent or luminescent or otherwise optically detectable moiety. In some embodiments, translocation of the modified virulence factor into the cytoplasm or into an intracellular compartment that has a different pH relative to the medium in which the cell is being maintained causes an alteration in the moiety resulting in an optically detectable signal. In some embodiments the signal is at least in part based on fluorescence resonance energy transfer (FRET). For example, a virulence factor can be modified to comprise an enzyme, e.g., a protease, capable of cleaving a fluorogenic substrate, wherein cleavage disrupts intramolecular FRET and changes the emission spectrum. Near-haploid mammalian cells having gene trap constructs inserted into the genome are contacted with the substrate under conditions in which the substrate is taken up (such process may be referred to as "loading" the cells with the substrate) and then contacted with the modified virulence factor. After cells internalize the modified virulence factor, cleavage of the substrate alters its emission spectrum. Thus cells that fail to internalize the modified virulence factor can be identified. For example, a system utilizing a virulence factor-β-lactamase fusion protein capable of hydrolyzing the cephalosporin-based fluorescein/coumarin fluorogenic substrate CCF2 can be used. Such hydrolysis disrupts intramolecular CCF2 FRET and changes emission from fluorescein (EM 530 nm) to coumarin (EM 460 nm) fluorescence. See, e.g., J. P. Hobson, et al. Nat. Methods 3: 259 (2006); M. Moayeri and S. H. Leppla, Curr. Opin. Microbiol. 7: 19 (2004); S. Liu and S. H. Leppla, J. Biol. Chem. 278: 5227 (2003). In some embodiments the substrate comprises a fluorophore and quencher joined to one another by a linker that comprises a cleavage site for an enzyme, wherein the quencher quenches emission from the fluorphore. Cells are loaded with the substrate. Internalization of the modified virulence factor results in cleavage, releasing the fluorophore from the quencher so that fluorescence is no longer quenched.

In other embodiments, expression or activity of a reporter or sensor, which may be genetically encoded, is used as a readout to identify genes affecting a phenotype of interest. Such reporters or sensors could be used to identify genes involved in a wide variety of cell processes or events, such as transcription of particular genes, transcriptional activation of certain promoters, protein modification such as phospho-rylation, intracellular calcium release or influx, nuclear translocation of particular proteins, or any of a wide variety of signaling events. In some embodiments, the reporter or sensor allows detection of a process, event, or detection of a substance such as a metabolite. Cells that have an insertion in a gene that encodes a gene product that plays a role in or affects such process, event, or in the synthesis or degrada-tion/removal of the substance exhibit a different phenotype than cells that do not have such an insertion and can thus be identified, thus permitting identification of the gene. In some embodiments a reporter is used to provide information regarding activity of the MAPK signaling pathway, mTOR signaling pathway, NF-κB signaling pathway, Hedgehog signaling pathway, TGF beta signaling pathway, JAK-STAT signaling pathway, p53 pathway, CDK pathway, Wnt sig-naling pathway, cAMP dependent pathway, or a biosynthetic or degradative pathway. See, e.g., the Kyoto Encyclopedia of Genes and Genomes (KEGG) PATHWAY Database (www.genome.jp/kegg/pathway.html.

In some embodiments, the invention provides methods for identifying genes that encode gene products that play a role in activity of an agent in a mammalian cell. The agent can be any substance of interest. The agent may be an organic or inorganic compound, e.g., a small molecule (which term refers to organic compounds, typically containing multiple carbon-carbon bonds, having a molecular weight of 2,500 daltons or less, e.g., 2,000 daltons or less, e.g., 1,500 daltons or less, e.g., 1,000 daltons or less), a nucleic acid, a protein, a lipid, or a carbohydrate. The agent may be a member of a compound library, which term refers to a collection of compounds that may be structurally related, structurally diverse, or unrelated. The library may comprise, e.g., between 100 and 500,000 compounds, or more. The agent may be a synthetic agent (e.g., an agent having a structure invented by man and not found in nature) or a naturally occurring agent. The agent may be a combination of sub-stances, which may be defined (i.e., their structure or iden-tity is known), or at least in part undefined (e.g., an extract or culture supernatant).

In some embodiments the agent is a "drug" (also referred to herein as a "therapeutic agent"), which term refers to a substance that is used to treat, prevent, or diagnose a disease or condition in a subject or to modify a chemical process in the body for a specific purpose, or a substance that is a candidate for such use. See, e.g., Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; $10^{th}$ ed. (2006) or 11th edition (July 2009). Typically the term "drug" does not refer to foodstuffs or substances that are adminis-tered primarily to provide general nutrition to a subject. "Treating" can refer to curing, alleviating one or more symptoms or signs, and/or slowing progression of a disease. "Preventing" can refer to administering an agent to a subject who has not developed a disease or condition, so as to reduce the likelihood that the disease or condition will occur or so as to reduce the severity of the disease or condition should it occur. The subject may be identified as at risk of devel-oping the disease or condition (e.g., at increased risk relative to many most other members of the population or as having a risk factor that increases likelihood of developing the disease). In some embodiments the agent is a deleterious agent, e.g., a toxic agent (which may or may not be a substance produced by a pathogen). In certain embodiments of the invention an agent of interest, e.g., drug, is an anti-neoplastic agent. In certain embodiments of the inven-tion the agent of interest is an enzyme inhibitor (e.g., kinase inhibitor or phosphatase inhibitor or protease inhibitor), proteasome inhibitor, receptor agonist, receptor antagonist, anti-metabolite, alkylating agent, hormone, cytokine, or chemokine. A subject can be, e.g., a vertebrate, e.g., a mammal or avian. Exemplary mammals include, e.g., humans, non-human primates, rodents (e.g., mouse, rat, rabbit), ungulates (e.g., ovine, bovine, equine, caprine spe-cies), canines, and felines. In some embodiments, the animal is a mammal of economic importance, e.g., such as a cow, horse, pig, goat, or sheep.

The invention provides a method of identifying a gene that encodes a gene product that plays a role in activity of an agent in mammalian cells, the method comprising steps of: (a) introducing a gene trap vector into near-haploid mam-malian cells, wherein the gene trap vector comprises a nucleic acid construct comprising a nucleic acid encoding a reporter that allows the identification of a cell expressing said nucleic acid, wherein said nucleic acid construct inte-grates into the genome of said near-haploid mammalian cells; (b) contacting the mammalian cells with an agent at a concentration sufficient to cause a detectable effect on non-mutant near-haploid cells; (c) identifying a cell that contains said nucleic acid construct integrated into its genome and does not exhibit said effect (or exhibits the effect to a greater or lesser extent); and (d) identifying a gene into which the nucleic acid construct integrated, thereby identifying a gene that encodes a gene product that plays a role in activity of the agent in mammalian cells. The phrase "in mammalian cells" should be understood to include agents that act at least in part outside the cell, e.g., agents that bind to cell surface molecules and do not need to be internalized in order to exert an effect on the cells. Such agents may interact with a cell surface molecule that has an intracellular domain or that interacts with another cell surface molecule that has an intracellular domain and thereby exert an effect intracellu-larly while remaining outside the cell. The "effect on the cells" can be an effect on a reporter in said cells and/or an intracellular reporter can be used as a readout or surrogate for the effect on the cells. A "concentration sufficient to cause a detectable effect on non-mutant cells" can be deter-mined empirically or may be known in the art. "Non-mutant" cells typically means near-haploid cells that do not have a gene trap construct integrated into their genome.

A pathogen may infect a cell type, organ or organ system of interest. For example, in some embodiments the pathogen infects the liver, e.g., hepatocytes. In some embodiments the pathogen infects immune system cells, e.g., lymphocytes or macrophages. In some embodiments the pathogen infects the respiratory system, e.g., respiratory epithelial cells. In some embodiments the pathogen infects the nervous system (e.g., neurons). In some embodiments the pathogen infects skin cells (e.g., keratinocytes). In some embodiments the pathogen infects mucosal cells, e.g., cells of the gastroin-testinal tract. In some embodiments the pathogen infects erythroid cells. A virulence factor or agent may affect a cell type, organ or organ system of interest. For example, in some embodiments the virulence factor or agent affects the liver, e.g., hepatocytes. In some embodiments the virulence factor or agent affects immune system cells, e.g., lympho-cytes or macrophages. In some embodiments the virulence factor or agent affects the respiratory system, e.g., respira-tory epithelial cells. In some embodiments the virulence factor or agent infects the nervous system (e.g., neurons), e.g., a neurotoxin. In some embodiments the virulence factor or agent affects skin cells (e.g., keratinocytes). In some embodiments the virulence factor or agent affects mucosal cells, e.g., cells of the gastrointestinal tract. In some embodiments the virulence factor or agent affects erythroid cells.

In some embodiments of the invention, the phenotype of interest is propensity to undergo apoptosis, e.g., in response to an agent or condition that has the capacity to induce apoptosis. The agent may be, e.g., a drug that induces programmed cell death (apoptosis).

Thus, in some aspects the invention provides a composition comprising a population of near-haploid mammalian cells and a pathogen. The absolute number of cell, pathogen, and the multiplicity of infection (MOI) can vary. "Multiplicity of infection" refers to the ratio of infectious agents to infection targets (e.g., cells). One of skill in the art will be able to determine a suitable amount of cells and pathogen to use. If desired, a range of dilutions of a pathogen stock can be tested to identify an appropriate amount. In some embodiments an MOI of between $10^{-4}$ and $10^2$ is used. For example, an MOI of between 0.001 and 10, e.g., between 0.01 and 1, can be used. In some embodiments, an amount of pathogen suitable to produce a detectable effect, e.g., a pathologic change, on between 10% and 100% of cells is used. In some aspects the invention provides a composition comprising a population of near-haploid mammalian cells and an agent, e.g., a toxin, drug, or other agent. In some embodiments, an amount of agent suitable to produce a detectable effect on between 10% and 100% of cells is used.

Once a gene is identified in an initial screen, additional studies may be performed to confirm and/or analyze the role of the gene in the phenotype of interest. Prior to such confirmation the gene may be referred to as a "candidate gene" to denote that the gene is a candidate for affecting the phenotype of interest. For example, the candidate gene can be "knocked down" in near-haploid cells not having a gene trap construct inserted into the gene or in any cell of interest. "Knock-down" typically refers to a reduction in expression, which may occur, e.g., at the level of transcription, mRNA stability, translation, or protein stability. Such knockdown can be accomplished, e.g., using RNA interference (RNAi). Such reduction can be complete (e.g., the amount of gene product is reduced to background levels) or less than complete. For example, expression at the RNA and/or protein level can be reduced by 50%, 75%, 90%, or more. If such knockdown has an effect on the phenotype, the gene is confirmed as affecting the phenotype. One of skill in the art will appreciate that RNAi can be achieved using a variety of approaches. For example, cells can be contacted with short interfering RNA (siRNA) targeted to the candidate gene, or cells can be modified to express a precursor molecule such as a short hairpin RNA (shRNA) targeted to the candidate gene, which precursor molecule is processed intracellularly to yield an siRNA. As known in the art, siRNAs typically comprise two separate nucleic acid strands that are hybridized to each other to form a duplex. They can be synthesized in vitro, e.g., using standard nucleic acid synthesis techniques or by cleavage of a longer dsRNA, e.g., by an RNase III or RNase III-like enzyme such as Dicer. In certain embodiments an siRNA or shRNA comprises a duplex portion about 15-29 nucleotides (nt) long, e.g., between 17-25 nt long, e.g., between 19-23 nt long, wherein either or both strands optionally has a 3' overhang of 1-5 nucleotides long (e.g., 2 nucleotides), which may be composed of deoxyribonucleotides. In some embodiments, the strands are perfectly complementary within the duplex portion, while in other embodiments, the duplex portion could contain one or more mismatched nucleotide pairs or bulges. In some embodiments, each strand of an siRNA is between 15-29 nucleotides in length, e.g., between 19-25 nt long, e.g., 21-23 nt long. shRNA comprise a single nucleic acid strand that contains two complementary portions separated by a predominantly non-self-complementary region. The complementary portions hybridize to form a duplex structure and the non-self-complementary region forms a loop connecting the 3' end of one strand of the duplex and the 5' end of the other strand. shRNAs can undergo intracellular processing to generate siRNAs. In some embodiments, at least two different siRNAs targeted to the candidate gene are used in order to help ensure that the effect of the knockdown is a result of inhibiting expression of the candidate gene (rather than being an "off-target" effect). In other embodiments, the near-haploid cells having an insertion into the candidate gene are genetically modified to express the candidate gene. If such expression reverses the effect of the insertion, the candidate gene is confirmed as affecting the cell phenotype. In some embodiments, genetic modification involves introducing into the cell a nucleic acid that encodes a gene product of a candidate gene. The nucleic acid may be introduced into the cell using a suitable vector, e.g., a virus or plasmid. Typically, the nucleic acid that encodes the gene product is operably linked to expression control element(s), e.g., a promoter or promoter/enhancer, suitable to direct expression in the cell. Expression control element(s) could be constitutive or regulatable (e.g., inducible), and may be cell or tissue type specific or may direct expression in many, most, or all cell types. In some embodiments, at least a portion of the introduced genetic material becomes integrated stably into the genome of the cell.

In some embodiments, near-haploid cells having an insertion into the candidate gene are genetically modified to express a variant of a gene product of the candidate gene. The variant may differ from a gene product encoded by the candidate gene by the addition, deletion, or substitution of one or more nucleotides or amino acids. In some embodiments, a variant is at least 70%, 80%, 90%, 95%, 96%, 97%, 98%, 99%, or more identical to the product encoded by the candidate gene over at least 50%, 60%, 70%, 80%, 90%, 95%, 96%, 97%, 98%, 99%, or 100% of the length of the gene product. Percent identity may be determined using methods known in the art. For example, the percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of $TG_A$ and $TG_B$ (here $TG_A$ and $TG_B$ are the sum of the number of residues and internal gap positions in sequences A and B in the alignment), and multiplying by 100. When computing the number of identical residues needed to achieve a particular percent identity, fractions are to be rounded to the nearest whole number. Sequences can be aligned with the use of a variety of computer programs known in the art. For example, computer programs such as BLAST2, BLASTN, BLASTP, Gapped BLAST, etc., generate alignments. The algorithm of Karlin and Altschul (Karlin and Altschul, Proc. Natl. Acad. Sci. USA 87:22264-2268, 1990) modified as in Karlin and Altschul, Proc. Natl. Acad Sci. USA 90:5873-5877,1993 is incorporated into the NBLAST and XBLAST programs of Altschul et al. (Altschul, et al., J. MoI. Biol. 215:403-410, 1990). In some embodiments, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. See the Web site having URL www.ncbi.nlm nih gov. Other suitable programs include CLUSTALW (Thompson J D, Higgins D G, Gibson T J, Nuc Ac Res, 22:4673-4680, 1994) and GAP (GCG Version 9.1; which implements the Needleman & Wunsch, 1970 algorithm (Needleman S B, Wunsch C D, J Mol Biol, 48:443-453, 1970.) The sequence of a variant may be, e.g., randomly produced, or designed by man. In some embodiments, a variant has reduced activity as compared with a product encoded by the candidate gene. For example, the activity may be reduced by at least 25%, 50%, 60%, 70%, 80%, 90%, or more) as compared with the product encoded by the candidate gene. In some embodiments, the variant is inactive (e.g., its activity is undetectable or within background levels) or is greatly reduced (e.g., reduced by at least 90%) as compared with the product encoded by the candidate gene. For example, if the gene product is an enzyme, the enzyme may be catalytically inactive or have greatly reduced catalytic activity. In some embodiments, the variant may have a deletion or substitution of a residue that is required for enzymatic activity. In some embodiments, the residue is predicted to be required based on homology with other enzymes. In some embodiments, the residue has been experimentally verified as being required for activity. If expression of a variant that is inactive or has greatly reduced activity fails to reverse the effect of the gene trap insertion, the candidate gene is confirmed as affecting the cell phenotype. For example, in some embodiments, an insertion renders a near-haploid mammalian cell resistant to infection by a pathogen. If expression of an inactive variant of a gene product of the candidate gene fails to restore susceptibility, the candidate gene product is confirmed as being required for infection by the pathogen. In some embodiments, if a gene product has multiple activities, failure of a variant that lacks a particular activity to reverse the effect of the gene trap insertion further verifies that the phenotype is attributable to the particular activity that is lacking in the variant. A variant that is inactive or has greatly reduced activity may have additional uses. In some embodiments, such variant may act as an inhibitor of a pathogen, virulence factor, toxin, or other agent. For example the variant may bind to the agent but may not mediate the effects of the agent on a cell. In some embodiments, a variant is a functional variant, i.e., the variant at least in part retains at least one biological activity of the molecule of which it is a variant. In some embodiments, a functional variant retains sufficient activity to be distinguishable from a non-homologous or inactive polynucleotide or protein. In some embodiments, a functional variant retains at least 10%, 20%, 30%, 40%, 50%, 60%, 70%, 80%, 90%, 95%, 96%, 97%, 98%, 99%, or more of the activity of the molecule of which it is a variant, e.g., about equal activity. In some embodiments, a functional variant may have greater activity than the molecule of which it is a variant.

In some embodiments, a variant of a protein comprises one or more conservative amino acid substitutions. Conservative substitutions may be made on the basis of similarity in side chain size, polarity, charge, solubility, hydrophobicity, hydrophilicity and/or the amphipathic nature of the residues involved. As known in the art, such substitutions are, in general, more likely to result in a variant that retains activity as compared with non-conservative substitutions. In one embodiment, amino acids are classified as follows:

Special: C
Neutral and small: A, G, P, S, T

28

Polar and relatively small: N, D, Q, E
Polar and relatively large: R, H, K
Nonpolar and relatively small: I, L, M, V
Nonpolar and relatively large: F, W, Y
Special: C See, e.g., Zhang, J. J. Mol. Evol. 50:56-68, 2000). In some embodiments, proline (P) is considered to be in its own group as a second special amino acid. Within a particular group, certain substitutions may be of particular interest, e.g., replacements of leucine by isoleucine (or vice versa), serine by threonine (or vice versa), or alanine by glycine (or vice versa). Of course non-conservative substitutions are often compatible with retaining function as well. In some embodiments, a substitution or deletion does not alter or delete an amino acid important for activity. In some embodiments, a functional variant comprises a polypeptide at least 95%, 96%, 97%, 98%, 99% or 100% identical to a polypeptide of which it is a variant, e.g., over at least 70%, 75%, 80%, 85%, 90%, 95%, 96%, 97%, 98%, or 99% or 100% of the full length of the polypeptide of which it is a variant. If desired, a variant could be tested in cell-free and/or cell-based assays to assess their activity.

In some embodiments, the invention provides a collection of near-haploid cells with an insertion in a candidate gene, wherein the near-haploid cells express variants of a product encoded by a candidate gene, wherein the variants differ in sequence. The alterations in sequence may affect, e.g., expression level, activity, localization, etc. A collection of near-haploid cells expressing the variants may be used, e.g., to further analyze the function of the gene product and/or the mechanism of action of an agent that acts on a cell or the role of the gene product in the life cycle of a pathogen.

In some embodiments, a variant comprises a heterologous sequence. For example, a variant of a polypeptide may comprise a heterologous polypeptide portion. The heterologous portion often has a sequence that is not present in or homologous to the polypeptide. A heterologous portion may be, e.g., between 5 and about 5,000 amino acids long, or longer. Often it is between 5 and about 1,000 amino acids long. In some embodiments, a heterologous portion comprises a sequence that is found in a different protein, e.g., a functional domain. In some embodiments, a heterologous portion comprises a sequence useful for purifying, expressing, solubilizing, and/or detecting the protein. In some embodiments, a heterologous portion comprises a "tag", e.g., an affinity tag or epitope tag. For example, the tag can be an affinity tag (e.g., HA, TAP, Myc, 6×His, Flag, GST), fluorescent or luminescent protein (e.g., EGFP, ECFP, EYFP, Cerulean, DsRed, mCherry), solubility-enhancing tag (e.g., a SUMO tag, NUS A tag, SNUT tag, or a monomeric mutant of the Ocr protein of bacteriophage T7). See, e.g., Esposito D and Chatterjee DK. Curr Opin Biotechnol.; 17(4):353-8 (2006). In some embodiments, a tag can serve multiple functions. A tag is often relatively small, e.g., ranging from a few amino acids up to about 100 amino acids long. In some embodiments a tag is more than 100 amino acids long, e.g., up to about 500 amino acids long, or more. In some embodiments, a tag is located at the N- or C-terminus, e.g., as an N- or C-terminal fusion. The polypeptide could comprise multiple tags. In some embodiments, a tag is cleavable, so that it can be removed from the polypeptide, e.g., by a protease. Exemplary proteases include, e.g., thrombin, TEV protease, Factor Xa, PreScission protease, etc. In some embodiments, a "self-cleaving" tag is used. See, e.g., PCT/US05/05763. In some embodiments a tag or other heterologous sequence is separated from the rest of the protein by a polypeptide linker. For example, a linker can be a short polypeptide (e.g., 15-25 amino acids). Often a linker is composed of small amino acid residues such as serine, glycine, and/or alanine. A heterologous domain could comprise a transmembrane domain, a secretion signal domain, etc. A variant of a polypeptide, or cells that express it, could be used, e.g., in assays to identify compounds that modulate (e.g., inhibit) the activity or expression of the polypeptide, to facilitate purification of the polypeptide, etc. Thus, in certain embodiments, the invention relates to use of tagged or otherwise modified versions of gene products (e.g., polypeptides) encoded by a candidate gene identified as described herein.

If desired, a polynucleotide or polypeptide, e.g., a polynucleotide or polypeptide having a sequence present in a cell, e.g., near-haploid mammalian cell, or a variant thereof, can be produced using standard recombinant DNA techniques. A nucleic acid encoding a polypeptide can readily be obtained, e.g., from cells that express the polypeptide (e.g., by PCR or other amplification methods or by cloning) or by synthesis based on a known cDNA or polypeptide sequence. One of skill in the art would know that due to the degeneracy of the genetic code, numerous different nucleic acid sequences would encode the desired polypeptide. Optionally, a sequence is codon-optimized for expression in a host cell of choice. A nucleic that encodes a variant can readily be generated, e.g., by modifying native sequence using, e.g., site-directed mutagenesis, or by other standard methods.

A nucleic acid encoding the desired polypeptide, operably linked to appropriate expression control elements, usually in a vector such as a plasmid or virus (e.g., as part of the viral genome), can be introduced into prokaryotic or eukaryotic cells. In other embodiments, a polypeptide is produced using in vitro translation. Exemplary cells include, e.g., bacterial cells (e.g., E. coli), insect cells, mammalian cells, plant cells, fungal cells (e.g., yeast). One of skill in the art will be aware of suitable expression control elements (e.g., promoters). Promoters may be constitutive or regulatable, e.g., inducible or repressible. Exemplary promoters suitable for use in bacterial cells include, e.g., Lac, Trp, Tac, araBAD (e.g., in a pBAD vectors), phage promoters such as T7 or T3. Exemplary expression control sequences useful for directing expression in mammalian cells include, e.g., the early and late promoters of SV40, adenovirus or cytomegalovirus immediate early promoter, or viral promoter/enhancer sequences, retroviral LTRs, promoters or promoter/enhancers from mammalian genes, e.g., actin, EF-1 alpha, metallothionein, etc. The polyhedrin promoter of the baculovirus system is of use to express proteins in insect cells. One of skill in the art will be aware of numerous expression vectors that contain appropriate expression control element(s), selectable markers, cloning sites, etc., and can be conveniently used to express a polypeptide of interest. Optionally, such vectors include sequences encoding a tag, to allow convenient production of a polypeptide comprising a tag. Suitable methods for introducing vectors into bacteria, yeast, plant, or animal cells (e.g., transformation, transfection, infection, electroporation, etc.), and, if desired, selecting cells that have taken up the vector and deriving stable cell lines. Transgenic animals or plants that express the polypeptide could be produced using methods known in the art.

To produce a polypeptide, cells may be maintained in culture for a suitable time period, and the polypeptide is isolated and optionally further purified. (Of course a polypeptide could also be isolated from cells or tissues obtained directly from an organism that expresses it.) Standard protein isolation/purification techniques can be used. In some embodiments, affinity-based methods are used. For example, an antibody to the polypeptide can be employed. In the case of tagged polypeptides, an appropriate isolation method can be selected depending on the particular tag used.

Genes identified using the inventive methods have a number of different uses. Such methods of use are an aspect of the invention. For example, host cell factors that play a role in pathogenesis of a microorganism or virulence factor or that play a role in toxicity of an agent (and/or the genes or RNAs that encode such host cell factors) are targets for development of therapeutic agents to treat infections or diseases or deleterious effects caused or contributed to by the microorganism or virulence factor or agent. The invention provides a method of identifying a target for drug development comprising identifying a gene that affects susceptibility to a pathogen or virulence factor or agent using an inventive gene trap vector-based method, wherein mutation of the gene reduces susceptibility to the pathogen or virulence factor or agent, thereby identifying a target for development of a drug to treat or prevent infection by the pathogen or to treat or prevent a disease or condition caused at least in part by the virulence factor or agent. The invention further provides a method of identifying a candidate drug comprising (i) identifying a gene that affects susceptibility to a pathogen or virulence factor or agent using an inventive gene trap vector-based method, wherein mutation of the gene reduces susceptibility to the pathogen or virulence factor; and (ii) identifying a compound that inhibits expression or activity of an expression product of the gene, thereby identifying a candidate drug. The exact nature of the inhibition desired, and the manner of identifying a compound, may depend at least in part on the identity and/or activity of the gene product and its role in affecting susceptibility. For example, if the gene encodes a cell surface receptor for a pathogen or virulence factor, a compound that physically blocks the cell surface receptor or inhibits its synthesis (transcription, translation, or post-translational processing), or trafficking may be desired. If the gene encodes an enzyme, e.g., an intracellular enzyme, a compound that inhibits the enzyme or its synthesis may be desired. It will be understood that the extent of inhibition (e.g., of a process, expression level, or activity) can vary. For example, inhibition can refer to a reduction by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, in various embodiments of the invention. A compound could "counteract" rather than inhibit expression or activity of the gene product. For example, the compound could upregulate a pathway that is downregulated by the gene product, or the compound could downregulate a pathway that is upregulated by the gene product. One of skill in the art will appreciate that an RNA encoded by a candidate gene may have one or more functions other than encoding a protein. For example, the RNA may be directly involved in gene or protein regulation, splicing, mRNA processing, post-transcriptional modification, DNA replication, protein synthesis, etc. Examples of such "functional RNAs" include, e.g., microRNA precursors, transfer RNAs, ribosomal RNAs, and longer RNAs sometimes referred to in the art as "long non-coding RNAs" or "long non-protein-coding RNA". It should be noted that certain functional RNAs may encode a protein in addition to having one or more other functions.

Compounds that act on the gene, gene product, or pathway may be identified using methods known in the art for discovering compounds. Such methods can involve screening compound libraries (e.g., using high throughput screening), structure-based and/or computational drug design (e.g., virtual screening), etc. A wide variety of test compounds can be used in the inventive methods. For example, a test compound can be a small molecule, polypeptide, nucleic acid, oligonucleotide, lipid, carbohydrate, or hybrid molecule. Compounds can be obtained from natural sources or produced synthetically. Compounds can be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In various embodiments of the invention, a nucleic acid comprises standard nucleotides (abbreviated A, G, C, T, U), e.g., DNA or RNA. In other embodiments a nucleic acid comprises one or more non-standard nucleotides. In some embodiments, one or more nucleotides are non-naturally occurring nucleotides or nucleotide analogs. A nucleic acid can in various embodiments comprise chemically or biologically modified bases (for example, methylated bases), modified sugars (2'-fluororibose, arabinose, or hexose), modified phosphate groups (for example, phosphorothioates or 5'-N-phosphoramidite linkages), locked nucleic acids, or morpholinos. In some embodiments, a nucleic acid comprises nucleosides that are linked by phosphodiester bonds. In some embodiments, at least some nucleosides are linked by a non-phosphodiester bond. A nucleic acid can be single-stranded, double-stranded, or partially double-stranded. An at least partially double-stranded nucleic acid can have one or more overhangs, e.g., 5' and/or 3' overhang(s). Nucleic acid modifications (e.g., nucleoside and/or backbone modifications), non-standard nucleotides, delivery vehicles and approaches, etc., known in the art as being useful in the context of RNA interference (RNAi), aptamer, or antisense-based molecules for research or therapeutic purposes are contemplated for use in various embodiments of the instant invention. See, e.g., Crooke, ST (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008. A nucleic acid may comprise a detectable label, e.g., a fluorescent dye, radioactive atom, etc. "Oligonucleotide" refers to a relatively short nucleic acid, e.g., typically between about 4 and about 60 nucleotides long. The terms "protein", "polypeptide", and "peptide" may be used interchangeably. Proteins of interest herein often contain standard amino acids (the 20 L-amino acids that are most commonly found in nature in proteins). However, other amino acids (either naturally occurring or not) and/or amino acid analogs known in the art can be used in certain embodiments of the invention. One or more of the amino acids in a polypeptide (e.g., at the N- or C-terminus or in a side chain) may be modified, for example, by addition, e.g., covalent linkage, of a moiety such as an alkyl group, carbohydrate group, a phosphate group, a halogen, a linker for conjugation, etc.

In some embodiments, a compound collection ("library") is tested. The library may comprise, e.g., between 100 and 500,000 compounds, or more. Compounds are often arrayed in multwell plates. They can be dissolved in a solvent (e.g., DMSO) or provided in dry form, e.g., as a powder or solid. Collections of synthetic, semi-synthetic, and/or naturally occurring compounds can be tested. Compound libraries can comprise structurally related, structurally diverse, or structurally unrelated compounds. Compounds may be artificial (having a structure invented by man and not found in nature) or naturally occurring. In some embodiments, a library comprises at least some compounds that have been identified as "hits" or "leads" in other drug discovery programs and/or derivatives thereof. A compound library can comprise natural products and/or compounds generated using non-directed or directed synthetic organic chemistry. Often a compound library is a small molecule library. Other libraries of interest include peptide or peptoid libraries, cDNA libraries, and oligonucleotide libraries.

A library can be focused (e.g., composed primarily of compounds having the same core structure, derived from the same precursor, or having at least one biochemical activity in common). Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays (see https://mli nih gov/mli/). The NIH Clinical Collection (NCC) is a plated array of approximately 450 small molecules that have a history of use in human clinical trials. These compounds are highly drug-like with known safety profiles. The NCC collection is arrayed in six 96-well plates. 50 μl of each compound is supplied, as an approximately 10 mM solution in 100% DMSO. In some embodiments, a collection of compounds comprising "approved human drugs" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test compound may be, e.g., an antineoplastic, antibacterial, antiviral, antifungal, antiprotozoal, antiparasitic, antidepressant, antipsychotic, anesthetic, antianginal, antihypertensive, antiarrhythmic, antiinflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or anti-hormonal drug, etc. In some embodiments, a compound is one that has undergone at least some preclinical or clinical development or has been determined or predicted to have "drug-like" properties. For example, the test compound may have completed a Phase I trial or at least a preclinical study in non-human animals and shown evidence of safety and tolerability. In some embodiments, a test compound is substantially non-toxic to cells of an organism to which the compound may be administered or cells in which the compound may be tested, at the concentration to be used or, in some embodiments, at concentrations up to 10-fold, 100-fold, or 1,000-fold higher than the concentration to be used. For example, there may be no statistically significant effect on cell viability and/or proliferation, or the reduction in viability or proliferation can be no more than 1%, 5%, or 10% in various embodiments. Cytotoxicity and/or effect on cell proliferation can be assessed using any of a variety of assays (some of which are mentioned above). In some embodiments, a test compound is not a compound that is found in a cell culture medium known or used in the art, e.g., culture medium suitable for culturing vertebrate, e.g., mammalian cells or, if the test compound is a compound that is found in a cell culture medium known or used in the art, the test compound is used at a different, e.g., higher, concentration when used in a method of the present invention.

Suitable assays can be cell-free or cell-based in various embodiments. For example, a gene product may be produced (e.g., using recombinant techniques or chemical synthesis) or purified (e.g., from cells that express it) and used in a suitable assay to identify compounds that modulate (e.g., inhibit) expression or activity of the gene product, or cells can be contacted with compounds and those that modulate (e.g., inhibit) activity or expression can be identified. A variant of a candidate gene product, e.g., a tagged version of a polypeptide, can be used if desired in certain embodiments of the invention. The details of the assay can be selected based, e.g., on the nature of the particular gene product. For example, if the gene product is an enzyme, an appropriate assay for activity of the enzyme can be used. Binding assays can be used. Reporter-based assays can be used, e.g., to assess effects on expression. In some embodiments, a high throughput screen (HTS) is performed. A high throughput screen can utilize cell-free or cell-based assays. High throughput screens often involve testing large numbers of compounds with high efficiency, e.g., in parallel. For example, tens or hundreds of thousands of compounds can be routinely screened in short periods of time, e.g, hours to days. Often such screening is performed in multiwell plates containing, e.g., e.g., 96, 384, 1536, 3456, or more wells (sometimes referred to as microwell or microtiter plates or dishes) or other vessels in which multiple physically separated cavities are present in a substrate. High throughput screens can involve use of automation, e.g., for liquid handling, imaging, data acquisition and processing, etc. Without limiting the invention in any way, certain general principles and techniques that may be applied in embodiments of a HTS of the present invention are described in Macarrón R & Hertzberg RP. Design and implementation of high-throughput screening assays. Methods Mol Biol., 565: 1-32, 2009 and/or An W F & Tolliday N J., Introduction: cell-based assays for high-throughput screening. Methods Mol Biol. 486:1-12, 2009, and/or references in either of these. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser.

Compounds identified in initial screens may be used as starting points for medicinal chemistry efforts aimed at, e.g., improving one or more properties of the compound for use as a therapeutic agent and/or for identifying structurally related compounds that may have more desirable properties for use as a therapeutic agent. A compound may, for example, have one or more improved (i.e., more desirable) pharmacokinetic and/or pharmacodynamic properties as compared with an initial hit or may simply have a different structure. For example, a compound may have higher affinity for the molecular target of interest, lower affinity for a non-target molecule, greater solubility (e.g., increased aqueous solubility), increased stability, increased bioavailability, and/or reduced side effect(s), etc. Compounds that act on, e.g., inhibit, a gene product may be further characterized and/or tested to assess their ability to inhibit infection by the relevant pathogen and/or to inhibit deleterious effects (or other effects) caused by the relevant virulence factor or other agent. Such compounds may be characterized and/or tested in cell culture, in animal models, and/or in humans. Such methods are aspects of the invention.

In some embodiments the compound is an antibody or other agent such as an aptamer that specifically binds to a gene product of an identified gene. Methods for producing antibodies and aptamers that bind to a molecule of interest are well established in the art. The term "antibody" encompasses immunoglobulins and derivatives thereof containing an immunoglobulin domain capable of binding to an antigen. An antibody can originate from a mammalian or avian species, e.g., human, rodent (e.g., mouse, rabbit), goat, chicken, etc., or can be generated ex vivo using a technique such as phage display. Antibodies include members of the various immunoglobulin classes, e.g., IgG, IgM, IgA, IgD, IgE, or subclasses thereof such as IgG1, IgG2, etc. In various embodiments of the invention "antibody" refers to an antibody fragment or molecule such as an Fab', F(ab')2, scFv (single-chain variable) that retains an antigen binding site and encompasses recombinant molecules comprising one or more variable domains (VH or VL). An antibody can be monovalent, bivalent or multivalent in various embodiments. The antibody may be a chimeric or "humanized" antibody. An antibody may be polyclonal or monoclonal, though monoclonal antibodies may be preferred. In some aspects, an antibody is an intrabody, which may be expressed intracellularly. In some embodiments a compound comprises a single-chain antibody and a protein transduction domain (e.g., as a fusion polypeptide). The invention thus provides antibodies and aptamers that specifically bind to a gene product encoded by a candidate gene identified using an inventive gene trap insertion screen.

In some embodiments the compound is an RNAi agent, e.g., an siRNA, designed to specifically inhibit expression of an identified gene, e.g., by inducing cleavage of the corresponding mRNA. The invention thus provides RNAi agents that inhibit expression of a candidate gene identified using an inventive gene trap insertion screen.

In some aspects, the gene product encoded by a candidate gene can be used as a therapeutic agent or for research purposes. For example, in some embodiments, a candidate gene encodes a gene product to which a pathogen or toxic agent binds, e.g., a receptor that mediates entry of a pathogen or toxic agent into a cell. A recombinant, purified, or chemically synthesized version of such a gene product (or a variant thereof that retains ability to bind to the pathogen or toxic agent) could be administered to a subject and may compete with the endogenous cellular gene product for binding to the pathogen or toxic agent, thus reducing the effect of the pathogen or toxic agent on cells.

In some embodiments a compound that acts on the gene product or on a biological pathway involving the gene product is already known. This approach may help identify new uses for known compounds, e.g., FDA-approved drugs. In some embodiments, a target for drug development is a gene or host cell factor identified using an inventive screen, wherein the gene or host cell factor is not essential for cell viability and/or proliferation. In some embodiments, a target for drug development is a gene or host cell factor identified using an inventive screen, wherein inhibiting expression or activity of the gene or host cell factor does not have detectable deleterious effects on the cell.

It is noted that certain toxins are of use as therapeutic or diagnostic agents. For example, botulinus toxin blocks neuromuscular transmission and is used for a variety of therapeutic and cosmetic purposes. Identification of genes involved in mediating toxicity or in mediating other effects of useful toxins may be of use, e.g., to facilitate development new agents to be used for similar purposes or reducing potential side effects, or for purposes of improving or modifying the activity of such toxins. Identification of genes that mediate effects of toxins may offer targets for development of new agents that target the biological pathway(s) in which such toxins exert their effects, which may be of use, e.g., to develop therapeutic agents to treat diseases in which such pathways are involved.

The invention also provides methods of identifying a gene product required for an agent to have an effect on a cell. One such method comprises identifying a gene in a near-haploid mammalian cell, wherein insertion of a gene trap construct into the gene inhibits or prevents the effect. In some embodiments the gene identified encodes a direct or indirect target of the agent, e.g., a gene product that is altered by the agent in a manner that affects cell phenotype. In some embodiments the gene identified encodes a protein that is needed for activity of the agent, e.g., a transporter that mediates entry of the agent into the cell, or an enzyme that converts the agent into an active form. The method can be used to elucidate the mechanism of action of an agent, e.g., a drug. If the agent is a drug, the identified gene products are targets for drug development, e.g., to treat the same or similar disease or condition as that for which the drug is used. In some embodiments the method is used to identify a gene that encodes a gene product involved in resistance to a drug. For example, cancer cells often become resistant to antineoplastic agents. The inventive method may be used to identify genes that mediate such resistance. Compounds that inhibit the RNA or protein encoded by such genes may be of use to prevent or reverse drug resistance.

The invention provides genes that affect a number of different cell phenotypes, and methods of use thereof. As described in Examples 6A, 6B, and 7, genetic screens to identify genes encoding host cell factors that affect susceptibility to Anthrax and Diphtheria toxin and cytolethal distending toxin were performed, and genes whose mutation conferred resistance were identified. As described in Example 8, a genetic screen to identify genes encoding host cell factors that affect susceptibility to influenza virus was performed, and genes whose mutation conferred resistance were identified. Methods of using the genes identified in the screens, e.g., as targets for drug development, are aspects of the invention. Thus, in some aspects, the invention provides methods comprising identifying an inhibitor of a gene product encoded by a candidate gene that reduces susceptibility (increases resistance) to anthrax toxin, thereby identifying a candidate agent for treating a subject suffering from or at risk of infection by a pathogen that produces anthrax toxin (e.g., *B. anthracis*) or suffering from or at risk of deleterious effects due to anthrax toxin. In some embodiments, the candidate gene is WDR85. In some aspects, the invention provides methods comprising identifying an inhibitor of a gene product encoded by a candidate gene that reduces susceptibility (increases resistance) to diphtheria toxin, thereby identifying a candidate agent for treating a subject suffering from or at risk of infection by a pathogen that produces diphtheria toxin (e.g., *Corynebacterium diphtheriae*) or suffering from or at risk of deleterious effects due to diphtheria toxin. In some embodiments, the candidate gene is WD repeat domain 85 (WDR85; Gene ID for human gene: 92715; Gene ID for mouse (*Mus musculus*) gene: 67228). In some aspects, the invention provides methods comprising identifying an inhibitor of a gene product encoded by a candidate gene that affects susceptibility to a cytolethal distending toxin, thereby identifying a candidate agent for treating a subject suffering from or at risk of infection by a pathogen that produces a cytolethal distending toxin (CTD) or suffering from or at risk of deleterious effects due to a cytolethal distending toxin. CTDs are produced by a variety of bacteria, e.g., gram-negative bacteria such as Aggregatibacter, actinomycetemecomitans, *Camplyobacter* species, *E. coli, Heamophilus ducreyi, Helicobacter species, Salmonella* species (e.g., *S. typhi*), and *Shigella* species. In some aspects, the inventive methods relate to *E. coli* CTD.

In some embodiments, the candidate gene is transmembrane protein 81 (TMEM81; GeneID for human gene: 388730; Gene ID for mouse (*Mus musculus*) gene: 74626), sphingomyelin synthase 1 (SGMS1; GeneID for human gene: 259230; Gene ID for mouse (*Mus musculus*) gene: 208449), ATP6V0A2 (GeneID for human gene: 23545; Gene ID for mouse (*Mus musculus*) gene: 21871), or golgi glycoprotein 1 (also called golgi apparatus protein 1; Glg1; GeneID for human gene: 2734, Gene ID for mouse (*Mus musculus*) gene: 20340). In some aspects, the invention provides methods comprising identifying an inhibitor of a gene product of a candidate gene that reduces susceptibility (increases resistance) to influenza virus, thereby identifying a candidate agent for treating a subject suffering from or at risk of influenza virus infection. In some embodiments, the candidate gene is solute carrier family 35 (UDP-galactose transporter), member A2 (SLC35A2; GeneID for human gene: 7355; GeneID for mouse (*Mus musculus*) gene: 22232) or cytidine monophospho-N-acetylneuraminic acid synthetase (CMAS; GeneID for human gene: 55907; GeneID for mouse (*Mus musculus*) gene: 12764). One of skill in the art will readily be able to find amino acid sequences for these polypeptides, and sequences of the genes that encode them (e.g., in humans or other species) using public databases such as those available at the National Center for Biotechnology Information website, e.g., the Gene, Protein, and/or Nucleotide, database.

Compounds that inhibit a gene product may be further characterized and/or tested to assess their ability to inhibit infection by the relevant pathogen and/or to inhibit deleterious effects caused by the relevant toxin. Such compounds may be tested in cell culture, in animal models, and/or in humans. Such methods are aspects of the invention.

Compounds of therapeutic use may optionally be combined with one or more appropriate pharmaceutically acceptable carriers or excipients, e.g., as known in the art, to produce a pharmaceutical composition. A pharmaceutical composition may be administered to a subject by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or by inhalation, e.g., as an aerosol. The characteristics and ingredients of the pharmaceutical composition and route of administration may be selected, e.g., based at least in part on the condition to be treated. The term "pharmaceutically acceptable carrier or excipient" refers to a carrier (which term encompasses carriers, media, diluents, solvents, vehicles, etc.) or excipient which does not significantly interfere with the biological activity or effectiveness of the active ingredient(s) of a composition and which is not excessively toxic to the subject at the concentrations at which it is used or administered. Other pharmaceutically acceptable ingredients can be present in the composition as well. Suitable substances and their use for the formulation of pharmaceutically active compounds is well-known in the art (see, for example, "Remington's Pharmaceutical Sciences", E. W. Martin, 19th Ed., 1995, Mack Publishing Co.: Easton, PA, and more recent editions or versions thereof, such as Remington: The Science and Practice of Pharmacy. 21st Edition. Philadelphia, PA. Lippincott Williams & Wilkins, 2005, for discussion of pharmaceutically acceptable substances and methods of preparing pharmaceutical compositions of various types. A pharmaceutical composition is typically formulated to be compatible with its intended route of administration. For example, preparations for parenteral administration include sterile aqueous or non-aqueous solutions, suspensions, and emulsions. Aqueous carriers include water, alcoholic/aqueous solutions, emulsions or suspensions, including saline and buffered media, e.g., sodium chloride solution, Ringer's dextrose, dextrose and sodium chloride, lactated Ringer's. Examples of non-aqueous solvents are propylene glycol, polyethylene glycol, vegetable oils such as olive oil, and injectable organic esters such as ethyl oleate. fixed oils, polyethylene glycols, glycerine, propylene glycol or other synthetic solvents; preservatives, e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. pH can be adjusted with acids or bases, such as hydrochloric acid or sodium hydroxide. Such parenteral preparations can be enclosed in ampoules, disposable syringes or multiple dose vials made of glass or plastic. Pharmaceutical compositions and compounds for use in such compositions may be manufactured under conditions that meet standards or criteria prescribed by a regulatory agency. For example, such compositions and compounds may be manufactured according to Good Manufacturing Practices (GMP) and/or subjected to quality control procedures appropriate for pharmaceutical agents to be administered to humans.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Suitable excipients for oral dosage forms are, e.g., fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art.

Formulations for oral delivery may incorporate agents to improve stability in the gastrointestinal tract and/or to enhance absorption.

For administration by inhalation, inventive compositions may be delivered in the form of an aerosol spray from a pressured container or dispenser which contains a suitable propellant, e.g., a gas such as carbon dioxide, a fluorocarbon, or a nebulizer. Liquid or dry aerosol (e.g., dry powders, large porous particles, etc.) can be used. The present invention also contemplates delivery of compositions using a nasal spray or other forms of nasal administration.

For topical applications, pharmaceutical compositions may be formulated in a suitable ointment, lotion, gel, or cream containing the active components suspended or dissolved in one or more pharmaceutically acceptable carriers suitable for use in such composition.

For local delivery to the eye, the pharmaceutically acceptable compositions may be formulated as solutions or micronized suspensions in isotonic, pH adjusted sterile saline, e.g., for use in eye drops, or in an ointment.

Pharmaceutical compositions may be formulated for transmucosal or transdermal delivery. For transmucosal or transdermal administration, penetrants appropriate to the barrier to be permeated may be used in the formulation. Such penetrants are generally known in the art. Inventive pharmaceutical compositions may be formulated as suppositories (e.g., with conventional suppository bases such as cocoa butter and other glycerides) or as retention enemas for rectal delivery.

In some embodiments, a pharmaceutical composition includes one or more agents intended to protect the active agent(s) against rapid elimination from the body, such as a controlled release formulation, implants, microencapsulated delivery system, etc. Compounds may be encapsulated or incorporated into particles, e.g., microparticles or nanoparticles. Biodegradable, biocompatible polymers can be used, such as ethylene vinyl acetate, polyanhydrides, polyglycolic acid, PLGA, collagen, polyorthoesters, polyethers, and polylactic acid. Methods for preparation of such formulations will be apparent to those skilled in the art. For example, and without limitation, a number of particle-based delivery systems are known in the art for delivery of siRNA. The invention contemplates use of such compositions. Liposomes or other lipid-based particles can also be used as pharmaceutically acceptable carriers.

In some embodiments, a pharmaceutically acceptable derivative of a compound identified or validated according to an inventive method is used. According to the present invention, a pharmaceutically acceptable derivative of a particular compound includes, but is not limited to, pharmaceutically acceptable salts, esters, salts of such esters, or any other adduct or derivative which upon administration to a subject in need thereof is capable of providing the compound, directly or indirectly. Thus, pharmaceutically acceptable derivatives can include salts, prodrugs, and/or active metabolites. The term "pharmaceutically acceptable salt" refers to those salts which are, within the scope of sound medical judgment, suitable for use in contact with the tissues of humans and/or lower animals without undue toxicity, irritation, allergic response and the like, and which are commensurate with a reasonable benefit/risk ratio. A wide variety of appropriate pharmaceutically acceptable salts are well known in the art. Pharmaceutically acceptable salts include, but are not limited to, those derived from suitable inorganic and organic acids and bases. A pharmaceutically acceptable derivative may be formulated and, in general, used for the same purpose(s).

Pharmaceutical compositions, when administered to a subject, are preferably administered for a time and in an amount sufficient to treat the disease or condition for which they are administered, e.g., to treat infection or ameliorate an effect of a toxic agent. Therapeutic efficacy and toxicity of active agents can be assessed by standard pharmaceutical procedures in cell cultures or experimental animals. The data obtained from cell culture assays and animal studies can be used in formulating a range of dosages suitable for use in humans or other subjects. Different doses for human administration can be further tested in clinical trials in humans as known in the an. The dose used may be the maximum tolerated. dose or a lower dose. A therapeutically effective dose of an active agent in a pharmaceutical composition may be within a range of about 0.001 to about 100 ma/kg body weight, about 0.01 to about 25 mg/kg body weight, about 0.1 to about 20 mg/kg body weight, about 1 to about 10 mg/kg. Other exemplary doses include, for example, about 1 μg/kg to about 500 mg/kg, about 100 μg/kg to about 5 mg/kg), in some embodiments a single dose is administered while in other embodiments multiple doses are administered. Those of ordinary skill in the art will appreciate that appropriate doses in any particular circumstance depend upon the potency, of the agent(s) utilized, and may optionally be tailored to the particular recipient. The specific dose level for a subject may depend upon a variety of factors including the activity of the specific agent(s) employed, severity of the disease or disorder, the age, body weight, general health of the subject, etc.

It may be desirable to formulate pharmaceutical compositions, particularly those for oral or parenteral compositions, in unit dosage form for ease of administration and uniformity of dosage. Unit dosage form, as that term is used herein, refers to physically discrete units suited as unitary dosages for the subject to be treated; each unit containing a predetermined quantity of active agent(s) calculated to produce the desired therapeutic effect in association with an appropriate pharmaceutically acceptable carrier.

It will be understood that a therapeutic regimen may include administration of multiple unit dosage forms over a period of time. The period of time may be selected based at least in part on the particular condition being treated and/or the response of the subject. The time period may range from days to week, months, or years. In some embodiments, a time period is from 1 day to about 4 weeks. In other embodiments, a longer course of therapy is administered, e.g., over between about 4 and about 10 weeks. In some embodiments a subject is treated at least until at least one symptom or sign of a condition has started to decrease in severity or has significantly decreased in severity or until a subject is no longer at risk of developing the condition. In some embodiments, treatment may be continued indefinitely, e.g., in order to achieve prophylaxis. A subject may receive one or more doses a day, or may receive doses every other day or less frequently, within a treatment period.

In some embodiments, two or more compounds are administered in combination, wherein at least one of the compounds inhibits a gene product identified using an inventive gene trap insertion screen. In some embodiments, a second compound is already known in the art to be useful to treat a condition of interest. The phrase "in combination, as used herein, with regard to combination treatment means with respect to administration of first and second compounds, administration performed such that (i) a dose of the second compound is administered before more than 90% of the most recently administered dose of the first agent has been metabolized to an inactive form or excreted from the body; or (ii) doses of the first and second compound are administered within 48 hours of each other, or (iii) the agents are administered during overlapping time periods (e.g., by continuous or intermittent infusion); or (iv) any combination of the foregoing. The compounds may, but need not be, administered together as components of a single composition. In some embodiments, they may be administered individually at substantially the same time (by which is meant within less than 10 minutes of one another). In some embodiments they may be administered individually within a short time of one another (by which is meant less than 3 hours, sometimes less than 1 hour, apart). The compounds may, but need not, be administered by the same route of administration. When administered in combination with a second compound, the effective amount of a first compound needed to elicit a particular biological response may be less or more than the effective amount of the first compound when administered in the absence of the second compound (or vice versa), thereby allowing an adjustment of the amount dose of the either or both agent(s) relative to the amount that would be needed if one compound were administered in the absence of the other. For example, in certain embodiments, when compounds are administered in combination, a sub-therapeutic dosage of either of the compounds, or a sub-therapeutic dosage of both, may be used in the treatment of a subject in need thereof. A "sub-therapeutic amount" as used herein refers to an amount which is less than that amount which would be expected to produce a therapeutic result in the subject if administered in the absence of the other compound, e.g., less than a recommended amount. The effects of multiple compounds may, but need not be, additive or synergistic. One or more of the compounds may be administered multiple times.

In some embodiments, an agent known in the art as being useful for treating a subject infected with a particular pathogen is used as a second compound in combination with a compound identified as described herein, e.g., an inhibitor of a candidate gene whose inhibition reduces susceptibility to infection by the pathogen. In some embodiments, a compound that is not sufficiently active to be therapeutically useful is rendered therapeutically useful when administered in combination with an inhibitor identified as described herein. In some embodiments, a lower dose of such compound can be used when administered in combination with a compound identified as described herein.

In some embodiments, the invention provides a composition comprising a compound identified as described herein and a second compound useful for treating the same condition. In some embodiments, a unit dosage form comprising the two (or more) agents is provided.

The compounds may be provided as pharmaceutical packs or kits comprising one or more containers (e.g., vials, ampoules, bottles) containing a pharmaceutically acceptable compound and, optionally, one or more other pharmaceutically acceptable ingredients. Optionally associated with such container(s) can be a notice in the form prescribed by a governmental agency regulating the manufacture, use or sale of pharmaceutical products, which notice reflects approval by the agency of manufacture, use or sale for human administration. The notice may describe, e.g., doses, routes and/or methods of administration, approved indications, mechanism of action, or other information of use to a medical practioner and/or patient. Different ingredients may be supplied in solid (e.g., lyophilized) or liquid form. Each ingredient will generally be suitable as aliquoted in its respective container or provided in a concentrated form. Kits may also include media for the reconstitution of lyophilized ingredients. The individual containers of the kit are preferably maintained in close confinement for commercial sale.

In some embodiments, invention permits identification of genes involved in biological processes such as synthesis or metabolism of compounds of interest. Identification of such genes may enable engineering of improved synthetic pathways and/or development of ways to improve drug action or reduce the likelihood of side effects.

It will be appreciated that, a candidate gene from the same species as a near-haploid mammalian cell can be used in the various aspects of the invention, or, in certain embodiments, a homologous gene from a different mammalian species (e.g., an ortholog or gene having the most similar sequence), can be used. For example, a candidate gene can be identified using a near-haploid human cell, and a screen for an inhibitor of the homologous gene of a non-human animal can be performed, or a genetically modified non-human animal in which the homologous gene is genetically modified can be produced. The homologous gene in a different species can readily be identified, e.g., by searching databases using the name and/or sequence of a candidate gene or gene product (or, the gene from a different species of interest can be cloned using methods known in the art). Similarly, a compound identified as a modulator (e.g., inhibitor) of a gene product produced by a first species may be used as a modulator, e.g., an inhibitor of the homologous gene product as found in a different species, e.g., in cells or animals of a different species. In some embodiments, a candidate gene has a homolog in a non-mammalian organism. For example, the organism may be a non-mammalian vertebrate, e.g., an avian, reptile, amphibian, fish, etc. The various aspects of the invention include embodiments relating to such homologous genes and uses thereof.

A host cell factor involved in infection by a particular pathogen can be involved in infection by similar pathogens, e.g., phylogenetically related pathogens. Thus, once a host cell factor that affects susceptibility to a pathogen (e.g., a virus) is identified it may be used as a target for discovery of compounds useful to treat infections caused by similar pathogens, e.g., pathogens within the same family or genus. Such pathogens may infect host cells of the same species as the near-haploid mammalian cell and/or may infect host cells of other species, e.g., other vertebrate animals. (It will be appreciated that the sequence of the candidate gene in a different species may differ from that present in the near-haploid mammalian cell, as typical for homologous genes conserved across multiple species.) Compounds that act on a host cell factor for a first pathogen may be used to treat infections caused by other pathogens within that family or genus. In some embodiments, a gene that encodes a host cell factor for a pathogen that has relatively low virulence (or for which an effective vaccine exists) is identified using an inventive method. Compounds that act on, e.g., inhibit, the gene product are identified. Such compounds may be useful to to treat infection by a related more virulent pathogen. Similarly, a host cell gene involved in mediating the activity of a toxin or other agent (e.g., a gene that encodes a gene product that is a target of such toxin or agent and/or is required for the activity of the toxin or agent) may be involved in mediating the activity of related agents (e.g., structurally and/or functionally related agents). Thus, the invention encompasses using such candidate genes for the discovery of compounds that modulate (e.g., inhibit) the effects of such related compounds and/or for investigating mechanism of action of such related compounds.

The invention encompasses identifying a candidate gene using an inventive screen and generating or identifying a cell that has altered (e.g., reduced) expression or activity of a gene product encoded by the candidate gene. In some embodiments, the invention provides a genetically modified cell, wherein the cell is not a hear-haploid mammalian cell, wherein the cell has an engineered alteration in one or both copies of a candidate gene and/or expresses a variant of a gene product encoded by a candidate gene. (It will be appreciated that the cell may have inherited a genetic alteration, i.e., the cell may be descended from originally produced genetically engineered cell). For example, the candidate gene may be at least partially deleted and/or exogenous genetic material may be introduced into the gene. The cell can be a haploid cell (e.g., a gamete), a diploid cell, or an aneuploid cell in various embodiments, and can be of any cell type of interest. The invention provides cell lines comprising a population of cells descended from any of the cells described herein.

In some embodiments, the invention provides a non-human genetically modified animal (also referred to as a "transgenic animal"), e.g., a mammal or avian, wherein some or all of the cells of the animal have an engineered alteration in a candidate gene and/or express a variant of a gene product encoded by a candidate gene. (It will be appreciated that the animal may have inherited a genetic alteration, i.e., the animal may be descended from originally produced genetically engineered animal). Usually the alteration is present in the genome of most or all of the animal's cells, typically including germ line cells. For example, the candidate gene may be at least partially deleted and/or exogenous genetic material may be introduced into the gene.

In some embodiments, the invention provides a non-human genetically modified animal, e.g., a mammal (e.g., a mouse) or avian, in which expression of a candidate gene is altered. For example, at least some cells of the transgenic animal may express a short hairpin RNA, microRNA precursor, or antisense RNA that inhibits expression of the candidate gene. Standard methods known in the art may be used to produce the non-human genetically modified animals of the invention.

In other aspects, an animal that has reduced or absent expression of a candidate gene is generated or identified. The invention provides a method of generating a non-human multicellular organism, e.g., a non-human animal, e.g., a non-human vertebrate, that has increased resistance to a pathogen (e.g., a virus) or deleterious agent. In one aspect, the non-human multicellular organism has reduced activity of a candidate gene product as compared with a normal, non-transgenic organism of the same species. In some embodiments, the organism is a transgenic, non-human vertebrate that has a targeted insertion into, or deletion of at least part of, one or both copies of a candidate gene, so that the animal has reduced expression of functional gene product. It will be appreciated that the alteration or disruption could be in a transcribed portion of a gene or in a non-transcribed region. In some embodiments, an alteration or disruption is in a regulatory region such as an expression control element (e.g., a promoter or enhancer).

In other embodiments, the transgenic non-human animal expresses an RNAi agent, e.g., a shRNA, microRNA, or antisense RNA that reduces expression of a candidate gene. In some embodiments, the organism is a rodent, e.g., a mouse. In some embodiments the organism is not a rodent. In some embodiments, the vertebrate is an animal of commercial importance. For example, the organism may contribute at least $10,000 to the gross national product of at least one country and/or be an object of interstate or international commerce. Exemplary animals of commercial importance are, e.g., cows, horses, sheep, goats, pigs, chickens, turkeys, fish. In some embodiments, an animal is a domesticated animal, e.g., a farm animal, e.g., livestock such as a cow, pig, sheep, goat, or horse. In some embodiments, the animal is of a non-domesticated species. Optionally the species is endangered. The method can be used to identify individuals that are resistant to pathogen infection or effect of a deleterious agent and have improved likelihood of surviving in the wild or in captivity. Animal resistance to infection may reduce the spread of pathogens that can infect both animal and human hosts. Mutations or deletions can be engineered using a variety of suitable methods known in the art, etc. The transgenic organism can be generated using standard methods known in the art for generating such organisms. For example, somatic cell nuclear transfer (SCNT) can be used.

In another aspect, the invention provides a method comprising identifying a non-human multicellular organism, e.g., a non-human vertebrate, e.g., a non-human animal, with reduced or absent functional product of a candidate gene identified using an inventive gene trap insertion screen. In some embodiments, the organism is not a rodent. In some embodiments the animal is not a mouse. In some embodiments, the organism has reduced expression of the gene product. In some embodiments the organism expresses a functionally inactive variant or fragment of the gene product. For example, the organism could have a frameshift mutation or a deletion or alteration of at least some residues needed for activity. The organism can be identified using, e.g., genotyping (e.g., to identify animals that have mutations or polymorphisms that result in decreased or altered expression or activity) and/or examining expression level in tissues and identifying animals with low or absent expression or activity. In some embodiments, polymorphisms, e.g., single nucleotide polymorphisms (SNPs) that are known in the art are examined. For example, genome projects and other sequencing efforts have identified numerous SNPs in animal genomes. SNPs, e.g., SNPs located in or near a candidate gene can be assessed to identify those that are associated with altered, e.g., reduced or absent, functional gene product. Animals carrying such SNPs can be identified. In some embodiments, the reduced or absent expression or activity occurs in at least some tissues and/or cells that are targets for infection by a pathogen or are targets for a deleterious agent (e.g., a toxin). In some embodiments, the reduced or absent expression or activity occurs in most or all tissues. Organisms with a desirable trait (e.g., reduced or absent expression or activity in at least some tissues) can be selected. Standard breeding techniques can be applied to produce animals with particularly low expression and/or activity. For example, standard methods of livestock breeding could be used. Traditional breeding schemes and/or marker-assisted selection may be employed. In some embodiments, a mutation or polymorphism is a spontaneously arising mutation, i.e., it is not generated by man. In some embodiments, a mutation is generated by man, e.g., using radiation or chemical mutagenesis. Thus the invention provides a method of producing a non-genetically modified non-human organism, e.g., non-human animal, with reduced or absent functional gene product. In some embodiments, the method comprising identifying or selecting an organism with reduced or absent functional gene product. In some embodiments, the non-human organism, is produced using selective breeding techniques. The invention further provides such organisms and methods of use thereof.

In some embodiments, a method comprises providing or using an organism with reduced or absent functional gene product in agriculture and/or animal husbandry. The organism can be a genetically modified organism or a non-genetically modified organism. The organism may have reduced likelihood of infection with a pathogen and/or may have reduced severity of infection. In some embodiments, the invention provides a method comprising (a) providing an animal that has reduced or absent functional expression or activity of a candidate gene product; and (b) engaging in animal husbandry using the animal. Animal husbandry encompasses the breeding and raising of animals for meat or to harvest animal products (such as milk, eggs, or wool) as well as the breeding and care of species for work and/or companionship. Agriculture refers to the production of food and/or goods through farming.

Reprogramming Near-Haploid Cells and/or Tumor Cells

It has recently been shown that mouse and human fibroblasts and various other normal somatic cell types can be reprogrammed in vitro to a pluripotent state through retroviral-mediated introduction of combinations of transcription factors, e.g., the four transcription factors Oct4, Sox2, Klf4, and c-Myc (with c-Myc being dispensable, although omitting c-Myc reduced reprogramming efficiency), or the four transcription factors Oct4, Nanog, Sox2, and Lin28 (see, e.g., Meissner, A., et al., Nat Biotechnol., 25(10):1177-81 (2007); Yu, J., et al, Science, 318(5858):1917-20 (2007); and Nakagawa, M., et al., Nat Biotechnol., 26(1):101-6 (2008). These transcription factors are often referred to as "reprogramming factors"). The resulting cells, termed induced pluripotent stem cells ("iPS cells"), appear essentially identical to embryonic stem (ES) cells, and can be used to generate viable chimeras with contribution to the germ line.

In some embodiments of the invention (e.g., as described in Example 12), a near-haploid cell is at least in part "reprogrammed" using somatic cell reprogramming technology. Such reprogramming can result in expression of genes that are not otherwise expressed by the near-haploid mammalian cell, which in some instances can include genes that encode host cell factors that are required for cytotoxicity or that are required for a process of interest. In some embodiments, reprogramming alters one or more properties of the cell or converts the cell into a cell that resembles a different cell type. In some embodiments a hematopoietic cell may be reprogrammed to a non-hematpoietic cell type as evidenced, for example, by alterations in expression of cell type specific markers and/or alteration in cell phenotype. For example, it was observed that transduction of the reprogramming factors allowed isolation of KBM7 derivative cells that grow in an adherent manner rather than in suspension. In some embodiments of the invention, near-haploid cells that have been subjected to reprogramming (or colonies comprising such cells) are transferred to non-ES cell medium, such as standard culture medium (e.g., DMEM), which may be supplemented with serum (e.g., fetal calf serum), and/or other components that promote cell growth. Reprogramming near-haploid mammalian cells according to the invention may expand the range of cell types and phenotypes that can be studied using the inventive methods. If desired, reprogrammed near-haploid mammalian cells can also be cultured using protocols known in the art to cause iPS cells or ES cells to differentiate along various differentiation pathways. For example, protocols that promote differentiation towards neural lineages, muscle cell lineages, etc., can be used.

The invention further provides methods of reprogramming somatic cells, wherein the somatic cells are tumor cells. Such reprogrammed tumor cells may be used, e.g., in screens to identify antineoplastic agents. In some embodiments a tumor cell originates from a carcinoma. In some embodiments a tumor cell originates from a sarcoma. In some embodiments a tumor cell originates from a hemato-logic malignancy, e.g., a lymphoma or leukemia or myeloma. In some embodiments a tumor cell originates from a breast, bladder, bone, brain, cervical, colon, endo-metrial, esophageal, head and neck, laryngeal, liver, lung (small cell or non-small cell), ovarian, pancreatic, prostate, stomach, renal, skin (e.g., basal cell, melanoma, squamous cell), testicular, or thyroid cancer. The tumor cell may be a cell of an established tumor cell line (e.g., one of the NCI-60 tumor cell lines) or another tumor cell line known in the art or newly established. In some embodiments a tumor cell is obtained from a biopsy or surgical sample, and is optionally expanded in culture prior to reprogramming In some embodiments, reprogramming methods that reduce the reliance on retroviral integration, such as tran-sient transfection and protein transduction approaches, are useed. Certain small molecules can enhance the reprogram-ming process. See, e.g., Shi, Y., et al., Cell Stem Cell, 2: 525-528 (2008); Huangfu, D., et al., Nature Biotechnology; Published online: 22 Jun. 2008|doi:10.1038/nbt1418. The invention encompasses use of such molecules or others, e.g., histone deacetylase inhibitors, methyltransferase inhibitors, Wnt pathway agonists, molecules that enhance expression of endogenous genes such as Oct4, Sox2, etc., in the methods of the invention, or molecules that can substitute for one or more reprogramming factors. See, e.g., PCT/US2008/010249 (WO/2009/032194) and PCT/US2008/004516 (WO/2008/124133); Lysiottis, et al., Proc Natl Acad Sci USA. 106(22):8912-7, 2009.

One skilled in the art readily appreciates that the present invention is well adapted to carry out the objects and obtain the ends and advantages mentioned, as well as those inherent therein. The details of the description and the examples herein are representative of certain embodiments, are exem-plary, and are not intended as limitations on the scope of the invention. Modifications therein and other uses will occur to those skilled in the art. These modifications are encom-passed within the spirit of the invention. It will be readily apparent to a person skilled in the art that varying substitu-tions and modifications may be made to the invention disclosed herein without departing from the scope and spirit of the invention.

The articles "a" and "an" as used herein in the specifica-tion and in the claims, unless clearly indicated to the contrary, should be understood to include the plural refer-ents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the inven-tion provides all variations, combinations, and permutations in which one or more limitations, elements, clauses, descrip-tive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element (s) can be removed from the group. It should be understood that, in general, where the invention, or aspects of the invention, is/are referred to as comprising particular ele-ments, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Where the claims or description relate to a composition of matter, e.g., a cell or gene trap vector it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., a method of using a cell or gene trap vector, it is to be understood that the cell or gene trap vector, and methods of using it, are aspects of the invention, unless otherwise indicated or unless it would be evident to one of ordinary skill in the art that a contradiction or inconsistency would arise.

Where ranges are given herein, the invention includes embodiments in which the endpoints are included, embodi-ments in which both endpoints are excluded, and embodi-ments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maxi-mum. Numerical values, as used herein, include values expressed as percentages. For any embodiment of the inven-tion in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that any product or composition of the invention may be "isolated", e.g., separated from at least some of the components with which it is usually associated in nature; prepared or purified by a process that involves the hand of man; and/or not occurring in nature.

The teachings of all documents, references, websites and databases referenced herein are incorporated herein by reference in their entirety for all purposes, including Carette, et al., "Haploid Genetic Screens in Human Cells Identify Host Factors Used by Pathogens," Science 326, 1231 (2009) and corresponding supporting online material. The invention will be further exemplified by the following non-limiting examples.

EXAMPLES

Classical genetic screens in model organisms have elucidated genetic programs underlying numerous basic biological processes. In mammalian cells, diploidy and asexual reproduction complicate large-scale gene disruption. Described herein is a versatile approach for genetic screens in which insertional mutagenesis is used to generate null alleles in a human cell line haploid for all chromosomes except chromosome 8. Using host-pathogen interactions as important targets, the validity and generality of this approach is demonstrated herein. WDR85 is identified as a gene required for the cytotoxic effects of diphtheria toxin and exotoxin A. Work described herein identifies the first human genes required for the action of cytolethal distending toxin (CDT), and identifies host factors essential for infection with influenza. WDR85 encodes an important element of the biosynthetic pathway of diphthamide, and CDT interacts with TMEM181, a cell surface receptor essential for intoxication.

Example 1: Characterization and Retroviral Infection of KBM7 Subclones

We first characterized a haploid genome setting in human cells that we believed would be permissive for efficient forward genetic approaches. A subclone of the CML cell line KBM7 has been described to carry a near haploid chromosome set [14]. First we examined if this cell line (generously provided by Dr. B. H. Cochran, Tufts University School of Medicine, Boston, Massachusetts) could be easily propagated, was tolerant to viral infection and could be efficiently subcloned. The term "KBM7 cell line" is used herein to refer to this near-haploid cell line or to a subclone thereof. Cells of the KBM7 cell line of a subclone thereof may be referred to as "KBM7 cells". KBM7 cells had a high subcloning efficiency (of around ~80%), and several of the subclones were examined further. The KBM7 subclones proliferated readily with a generation time of approximately 24 hrs and could be maintained at sparse and very high cell densities (e.g., ~1×10$^7$ cells/ml). Importantly, flow cytometric analysis indicated that KBM7 subclones had a hypodiploid karyotype as compared to diploid HCT116 colorectal carcinoma cells. One subclone was examined further by 24-color FISH spectral karyotyping. As indicated in FIG. 1a, these cells are haploid for all chromosomes except chromosome 8 and contain a Philadelphia chromosome (t(9;22)) characteristic of BCR-ABL transformed chronic myelogenous leukemia cells.

Example 2: Retroviral Infection of KBM7 Cells

We next determined whether it would be possible to infect KBM-7 cells with retroviruses. Virus was produced by transfection of a GFP expressing retroviral vector with packaging vectors in 293T cells (obtained from ATCC). The retroviral vector was pLIB-GFP (Clontech) but it will be understood that many different retroviral vectors could be used. Supernatant containing virus was used to infect KBM7 cells. To improve the infection efficiency of KBM7 cells with retroviruses, different conditions were tested. Centrifugation of the cells in a 24-well tissue culture dish for 45 minutes at 2,000 pm at room temperature resulted in a 2-fold increase in infection efficiency compared to no centrifugation. Next the effect of retronectin, polybrene and protamine sulphate addition was tested, yielding efficiencies of 25%, 33% and 44%, respectively. Eight microgram per milliliter culture medium of protamine sulphate is the preferred addition. Concentration of virus by ultracentrifugation for 1.5 h at 25,000 r.p.m. in a Beckman SW28 rotor dramatically improved infection rates compared to undiluted virus and was preferred over concentration by Amicon filters. In conclusion, cells are optimally infected when concentrated virus is used for a spin-infection in the presence of protamine sulphate. These subclones could be efficiently (~70-90%) infected with GFP expressing retroviral or lentiviral viruses that were VSV-G pseudotyped and maintained high levels of GFP expression for several months.

Example 2: Selection of Gene Trap Vectors for Insertional Mutagenesis in KBM7 Cells We next determined whether the observed haploid nature of the great majority of the genome sequence in the KBM7 subclone allowed the generation of knockout cells by mutagenesis. Since we knew that the cells could be readily infected by retroviruses, we explored the use in these cells of several viral gene-trap vectors designed to trap expressed genes. The large majority of promotorless gene trap vectors described in the literature are based on neomycin (G418, geneticin) selection. Surprisingly, initial experiments showed that KBM7 cells were inherently resistant to very high concentrations of neomycin, precluding use of preexisting vectors. A potentia exception was the UPA-Trap vector (described in Shigeoka et al. 2005 Nucleic Acids Res. 2005 33(2):e20.) that in addition to neomycin contains GFP. To test this vector, virus was produced by transfection of this vector with retroviral packaging vectors in 293T cells. Virus was harvested 36 hours post infection, concentrated by ultracentrifugation for 1.5 h at 25,000 r.p.m. in a Beckman SW28 rotor and resuspended in phosphate-buffered saline (200 µl). The virus was used to infect KBM7 cells using spin-infection. Conditions were used that resulted in an infection percentage of ~30% of pLIB-EGFP (Clontech) that was included in a separate infection as a control. Three days after infection GFP fluorescence was measured using FACS analysis in the UPA-Trap infected cells. Of the million counted cells no GFP positive cells were observed. We concluded that this vector was not useful for our approach. Next, the U3-CEO (Gebauer Metal., Genome Res. 2001 11(11):1871-7) vector was modified to replace the neomycin resistance gene with the puromycin resistance gene. For this purpose the coding sequence of the puromycin resistance gene was obtained by PCR amplification with primers containing overhanging BamHI and NcoI restriction sites: (5'-GATCGGATCCCACCGAGTACAAGCCCACGG-3' (SEQ ID NO: 124) and 5'-GATCC-CATGGTCAGGCACCGGGCTTGCG-3' (SEQ ID NO: 125)) and inserted in U-3-CEO replacing neomycin. Virus was produced from this vector and three days after infection puromycin at a concentration of 0.5 µg/ml was used to select infected cells. Puromycin resistant colonies developed at an efficiency of less than 1 out of 0.5 million infected cells. This efficiency was considerably lower than we desired for genome-wide insertional mutagenesis.

Example 3: Construction of Gene Trap Vectors Containing Vectors Containing Puromycin and GFP Selectable Markers Novel retroviral gene trap vectors that contain an inactivated LTR, a strong splice-acceptor site derived from the long fiber gene of Adenovirus serotype 40 (Carette et al. 2005 The Journal of Gene Medicine 7(8) 1053-1062), and either GFP or the puromycin resistance gene (PURO) followed by a SV40 polyadenylation signal were constructed as follows. The coding sequence of the PURO or GFP was obtained by PCR amplification with primers containing overhanging ClaI and NheI restriction sites as well as partial splice acceptor sites: (GFP:5'-GATCGCTAGCCGCAT-TTCTTTTTTCCAGATGGTGAGCAAGGGCGAGG-3' (SEQ ID NO: 126) and 5'-GATCGGATCCTTACTTGTA-CAGCTCGTCCATGC-3' (SEQ ID NO: 127) PURO: 5'-GATCGCTAGCCGCATTTCTTTTTTCCA-GATGACCGAGTACAAGCCCAC-3' (SEQ ID NO: 128) and 5'-GATCG-GATCCTCAGGCACCGGGCTTGCGGGTC-3' (SEQ ID NO:129)). These PCR products were inserted in pEGFPC1 (Clontech) replacing EGFP. Subsequently PCR was performed to introduce the complete splice acceptor site and to obtain either GFP or PURO followed by the poladenylation signal using primers containing overhanging ClaI and BamHI sites as well as the 5'end of the splice acceptor signal (GFP: 5'-GATCATCGATCGCAGGCGCAATCTTCGCAT-TTCTTTTTTCCAGATGG-3' (SEQ ID NO: 130) and 5'-GATCGGATCCTTACTTGTACAGCTCGTCCATGC-3' (SEQ ID NO: 131) PURO: 5'-GATCATC-GATCGCAGGCGCAATCTTCGCATTTCTTTTTTCCA-GATGAC-3' (SEQ ID NO:132) and 5'-GATCGGATCCT-TACTTGTACAGCTCGTCCATGC-3' (SEQ ID NO: 133)). These PCR products were inserted in pRETRO-SUPER (Brummelkamp et al. 2002 Cancer Cell. 2(3):243-7) replacing the polIII promoter. The resulting plasmids were named pGT-GFP and pGT-PURO. Gene trap constructs containing a GFP or a puromycin reporter gene in all three reading frames were generated.

The viral vectors contain an adenoviral splice acceptor site immediately upstream of a promoterless reporter and polyadenylation signal so that vector insertion into an intron of an active gene inactivates the native locus, and transcription driven by the gene's promoter results in a fusion transcript in which the upstream exon(s) are spliced to the GFP or PURO gene. Since transcription terminates at the inserted polyA site, the resulting fusion transcript encodes a truncated and nonfunctional version of the cellular protein and either GFP or PURO, as shown schematically in FIG. 1B for a gene trap vector in which the gene encoding GFP gene serves as a reporter gene.

Example 4: Generation of Mutant Cell Library

To generate a cell library with knock-out alleles in nearly all genes, the near-haploid KBM7-cells were infected with the gene traps generated as described in Example 3. Gene trap virus was made by transfection of 293T cells in T175 dishes with either pGT-GFP or pGT-PURO combined with retroviral packaging plasmids. The virus-containing supernatant was concentrated using ultracentrifugation for 1.5 h at 25,000 r.p.m. in a Beckman SW28 rotor. Batches of mutant KBM7 cells are typically made by infection of one 24-well tissue culture dish containing 1.5 million cells per well using the method described in Example 1. Cells infected with the gene trap containing the puromycin resistance gene were selected 2 days after infection using 500 ng puromycin per milliliter. After selection by limiting dilution, cells were expanded and frozen down for further screens. The GFP gene trap infected cells were either used for screens unselected to negate the gene trap introduced bias for actively expressed genes or were selected using FACS sorting for GFP-expressing cells. In some cases further stratification based on GFP expression was performed to obtain batches of cells with different levels of GFP. To increase the likelihood of identifying genes encoding gene products with a relatively longer half-life, the screens were performed on or after day 6 after gene trap infection, thereby allowing the gene products to dilute during cell proliferation.

Example 5: Methods for Mapping the Flanking Sequence of the Integrated Retroviral Gene Trap To retrieve the mutant allele created by the gene trap integration we made use of an inverse PCR protocol. For this, 4 microgram of genomic DNA was digested overnight at 37° C. with either NlaIII or MseI. Subsequently the digested DNA was column-purified (Qiagen) and 1 microgram DNA was ligated in a volume of 300 microliter using T4 DNA ligase (NEB) at room temperature overnight. After another round of column purification the DNA was used as template for an inverse PCR with outward facing primers. To identify genomic DNA sequences flanking the 5'-end of the LTR the following oligonucleotides were used: 5'-CTGCAGCATCGTTCTGTGTT-3'(SEQ ID NO: 134) and 5'-TCTCCAAATCTCGGTGGAAC-3' (SEQ ID NO: 135). To identify genomic DNA sequences flanking the 3'end of the LTR of the pGTGFP gene trap the following oligonucleotides were used: 5'-AACAGCTCCTCGCCCTTG-3'(SEQ ID NO: 136) and 5'-TCGTGACCACCCTGACCTAC-3' (SEQ ID NO: 137). To identify genomic DNA sequences flanking the 3'end of the LTR of the pGTPURO gene trap the following oligonucleotides were used: 5'-CTGCAGCATCGTTCTGTGTT-3' (SEQ ID NO: 138) and 5'-TCTCCAAATCTCGGTG-GAAC-3' (SEQ ID NO: 139). PCR products were columnpurified and directly sequenced using primer 5'-CTCGGTGGAACCTCCAAAT-3' (SEQ ID NO: 140) for DNA sequences flanking the 5'-end and primer 5'-AAGCCTCTTGCTGTTTGCAT-3' (SEQ ID NO: 141) for DNA sequences flanking the 3'-end. When multiple bands were present after PCR amplification, the products were first subcloned in a plasmid using Strataclone (Stratagene).

The majority of the integrations recovered in our initial experiments were relatively close to gene promoter regions and therefore predicted to create knockout alleles. We assessed this possibility in a subclone with a unique trap in the gene locus for the cell surface antigen CD43 (also named sialophorin, a major cell-surface sialoglycoprotein on T lymphocytes, monocytes, granulocytes, and some B lymphocytes) that had been identified by mapping several clones that were GFP positive. Western-blot analysis indicated expression of the endogenous gene was reduced to undetectable levels (FIG. 1C). Flow cytometric analysis for CD43 expression also showed no detectable CD43 expression in the trapped cell population (data not shown). These data indicate that, in the haploid genome context, single integrant gene-trap lines efficiently disrupt genes and eliminate gene expression.

Example 6A: Screens for Resistance to Anthrax and Diphtheria Toxin Cytotoxicity Next, we employed our haploid mutagenesis scheme in genetic screens to identify genes encoding host cell factors that affect susceptibility to bacterial toxins. For this we used the two bacterial toxins-Diphtheria toxin and Anthrax Lethal Factor (LF). Both toxins enter the cells through known receptors and the entry and cytotoxicity of Diphtheria toxin has been thoroughly studied for over 30 years [18, 19]. Diphtheria toxin enters by binding to the HB-EGF receptor and is cytotoxic to cells by targeting the Diphthamide residue in elongation factor-2 (EF-2) [19]. Anthrax-LF enters the cells in a complex with the bacterial Protective antigen (PA), which binds to the cell surface entry receptor [20]. Because Anthrax-LF itself is not cytotoxic to KBM7 cells, a protein in which Lethal factor is fused to the toxin domain of Diphtheria was used to select for resistant cells (LF-DT).

Several million cells of the near-haploid KBM7 subclone were infected with gene trap virus mixtures, which encode GFP and puromycin cassettes in three different reading frames. Cells were selected for GFP or puromycin expression and briefly cultured to maintain equal representation of gene trap mutations. We performed a genetic screen by plating these cells at 10,000 cells/well in a 96-well plate, and then treating with either toxin. Also, uninfected control cells were exposed to the bacterial toxins. About 30 wells of the gene-trap mutagenized cells showed cells that survived toxin treatment, whereas for the non-mutagenized cells only 5 wells contained living cells. Some mutants proliferated very poorly. Gene-trap mutagenized cells that survived were expanded and used to recover genomic sequences that flank the integration sites. Additionally, clones that were resistant to Diphtheria toxin were exposed to Anthrax LF-DT and vice versa. As indicated in FIG. 2, numerous independent integrations in the known entry receptors for Anthrax and Diphtheria toxins were recovered. All these integrations were in the sense orientation and predicted to disrupt essential parts of the corresponding receptors. Moreover, several integrations were recovered in genes that are known to be involved in the biosynthesis of Diphthamide [21, 22]; as the cell lethality by Anthrax Lethal Factor is mediated by fusion to the toxin domain of Diphtheria, these mutants score as 'double resistant' in our assay. Mutant alleles for this class of genes that are critical for Diphthamide biosynthesis were recovered at lower frequencies than the toxin receptors most likely because loss of these genes confers a strong growth disadvantage in KBM7 cells. These results indicate that new regulatory genes can be identified in biological processes that are well studied using our approach. Importantly, the outcome of this screen allows straightforward interpretation of the results because the recovery of multiple independent integrations points towards important components in the biological process of interest.

Figure 3B:
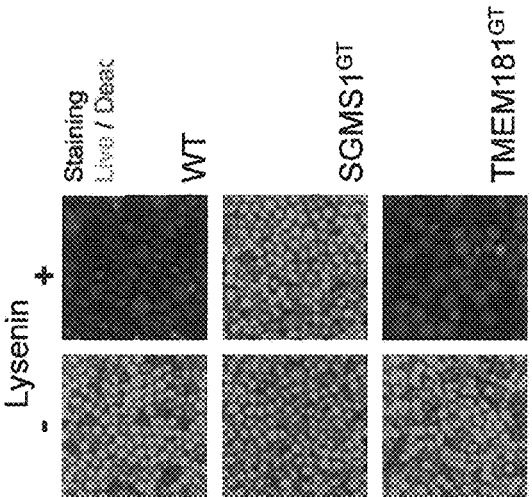
FIG. 3B shows that SGMS1 mutant cells are resistant to lysenin.
Figure 7:
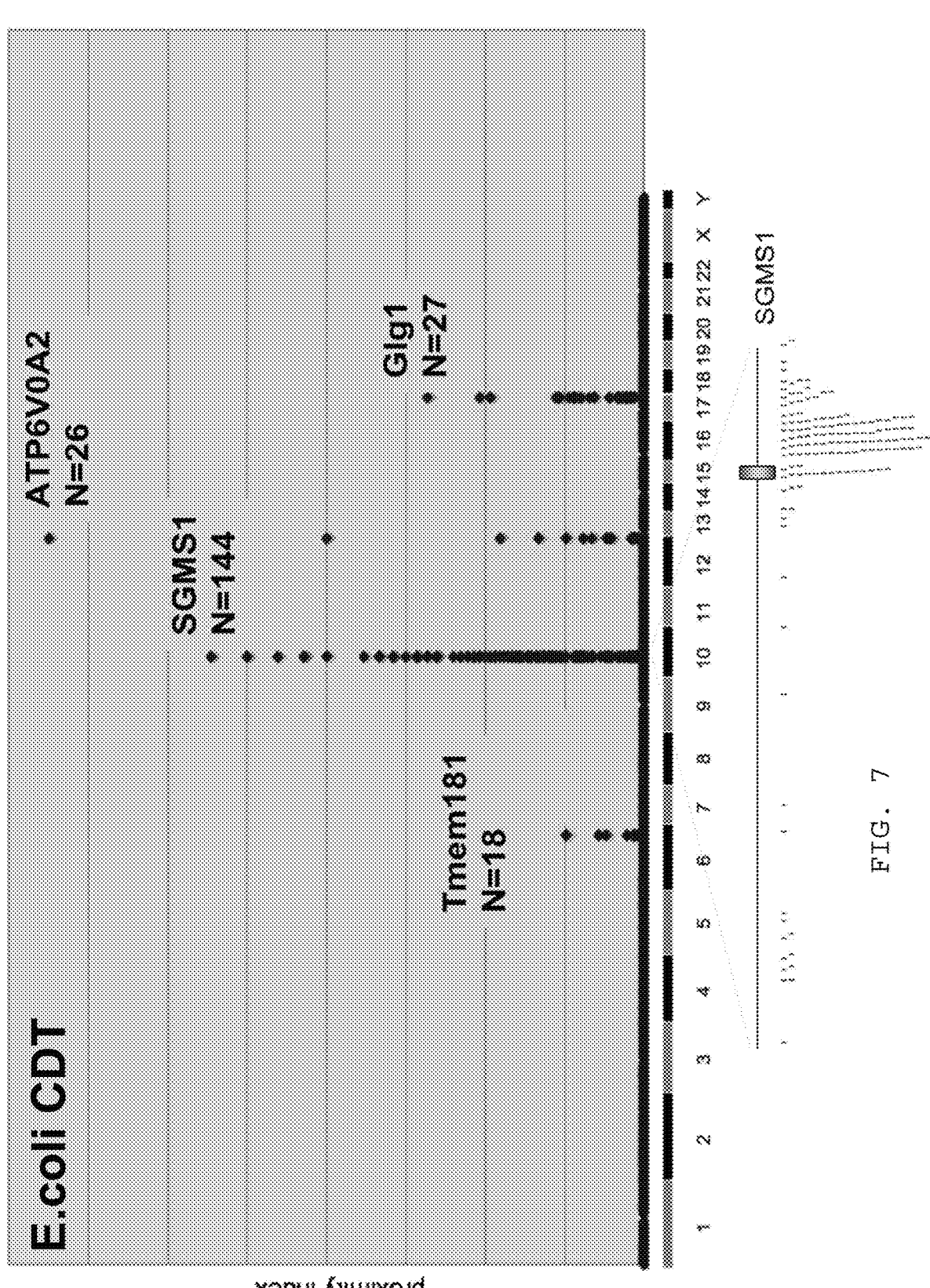
FIG. 7 is a plot showing insertion density across the genome after simultaneous mapping of multiple insertion sites identified in screen for host genes required for intoxication by *E. coli* cytolethal distending toxin.

Example 6B: Identification of the First Host Factors for *E. coli* Cytolethal Distending Toxin Cytolethal Distending Toxin (CDT) enters mammalian cells through an unknown mechanism and causes DNA damage by cleaving DNA resulting in the accumulation of cells in the G2/M phase of the cell cycle followed by cell death [23]. KBM7 cells are sensitive to this toxin and display the characteristic G2/M phase cell cycle arrest (FIG. 3A). In order to identify the first host factors that are used by the toxin we started a screen to identify knockout cells that are resistant to the cytotoxic effects of CDT. Fourteen mutants were recovered that were distributed in 3 genes: Sphingomyelin Synthase 1 (11 independent integrations), TMEM181 (2 independent integrations). As expected, loss of S GMS1 leads to cellular insensitivity to the earthworm toxin Lysenin that binds to cell surface Sphingomyelin and permeates the cells (FIG. 3B). In contrast, loss of TMEM181, a transmembrane containing GPCR family member, does not affect Lysenin sensitivity. Although more experimental follow-up is needed, it seems plausible that CDT initially binds to the newly identified cell surface receptor (TMEM181) and then undergoes lipid raft dependent endocytosis that can be perturbed by depletion of the lipid raft component Sphingomyelin. FIG. 7 furthers shows results on inventive screens for host genes required for intoxication by the *E. Coli* cytolethal distending toxin (CDT). Mutagenized cells were treated with CDT. After this selection step, gene trap insertion sites were comprehensively mapped using Solexa sequencing. Plotted are the retroviral insertion sites as mapped on their location on the genome. The proximity index is a measure of the distance of each insertion site relative to its neighbors. The closer to its neighbors, the higher the proximity index. Indicated are the genes to which the insertion sites cluster. N is the number of independent insertion in these genes.

Example 7: Identification and Initial Characterization of WDR85 as a Host Cell Factor Affecting Toxin Cytoxicity In the screens described in Example 6A, four independent integrations were identified in WDR85, a WD-40 repeat protein that has currently no known function. Cells containing integrations in WDR85 are resistant to both Diphtheria toxin and Anthrax LF-DT. There could be two explanations for the recovery of multiple WDR85 integrations in the DTA toxin resistance screen. First, it could be a common intergration site for retroviruses. Second, although Diphtheria toxin entry and cytotoxicity is very well studied, this gene could be a new critical player in this process. The fact that the WDR85 locus has not been reported to be an integration hotspot and all integrations are in the sense orientation argues for the latter explanation. We addressed this question by a cDNA complementation experiment. A retrovirus was generated that expresses both GFP and a HA-tagged WDR85 cDNA (see FIG. 2B). This virus was used to infect the KBM7 cells that contain a gene-trap integration in WDR85 (WDR85$^{GT}$). Flow cytometric analysis indicated that about 18% of the cells were infected and expressed GFP. Treatment of this cell population with Diphtheria toxin for 3 days revealed that GFP expressing cells were eliminated by the toxin, indicating that introduction of the WDR85 cDNA reverts the toxin resistance phenotype and makes the cells sensitive (FIG. 2C).

WDR85 could play a role in toxin entry or Diphthamide biosynthesis. To address this we have looked at EF-2 modification by Diphtheria, which results in a mobility shift detected using native gel electrophoresis. FIG. 2D indicates that KBM7 cell treatment with Diphtheria toxin results in a mobility shift of EF-2, indicating ADP-ribosylation, which is dependent on the presence of both the HB-EGF entry receptor and WDR85. Add-back of the WDR85 cDNA in WDR85GT cells makes EF-2 respond to toxin treatment as in wild-type cells.

Example 8: Screen for Resistance to Influenza Virus Infection

Figures 4A, 4B, 4C:
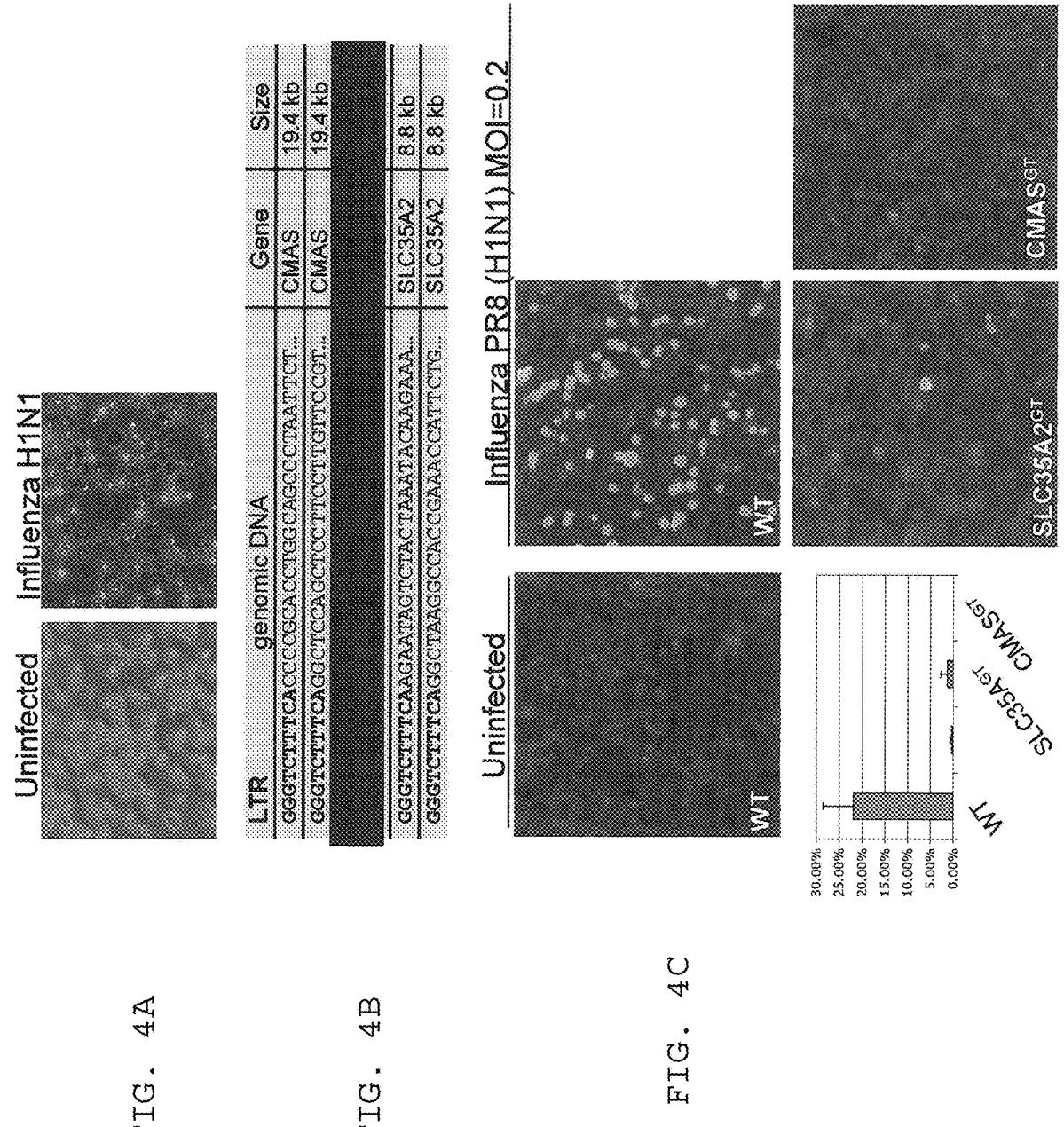
FIG. 4A illustrates that KBM7 cells can be infected by influenza virus.
FIG. 4B shows gene trap integration sites (SEQ ID NOS: 45-48, respectively) in clones that are resistant to influenza.
FIG. 4C shows detection of influenza virus infection in wild-type and mutant cell population by staining for Influenza A nucleoprotein (green) and Actin (red), 1 day after infection.

The identification of host factors needed for viral infection could provide valuable new targets for antiviral therapy. KBM7 cell can readily be infected with the flu virus H1N1 strain PR8 (FIG. 4A). In a genetic screen we isolated several mutant KBM7 cells that were resistant to flu infection. One million wild type or mutant KBM7 cells were incubated with 50,000 HA units of sucrose gradient purified influenza A/PR/8/34 virus (Charles River) in 100 μl serum free IMDM medium for 1 hour at room temperature. Subsequently, cells were taken up in IMDM medium containing 5 μg/ml trypsin and plated in a well of a 24-well tissue culture plate. Independent integrations were identified in 2 genes: CMAS and SLC35A2. Both CMAS and SLC35A2 affect the incorporation of sialic acid groups into glycosylated proteins, and since sialic acid is known to function as receptor for the flu virus, these experiments indicate that the flu virus binds and enters KBM7 cells in a conventional manner (FIG. 4C) [24]. Although the KBM7 genome has not been screened at saturation for resistance to flu, the transporter (SLC35A2) and enzyme (CMAS) identified here could serve as targets for flu therapeutics because they are not essential for either cell proliferation or viability. Neither gene has previously been identified as essential in determining susceptibility to flu.

Example 9: Sensitivity to TRAIL and Gleevec

Figures 6A, 6B, 6C:
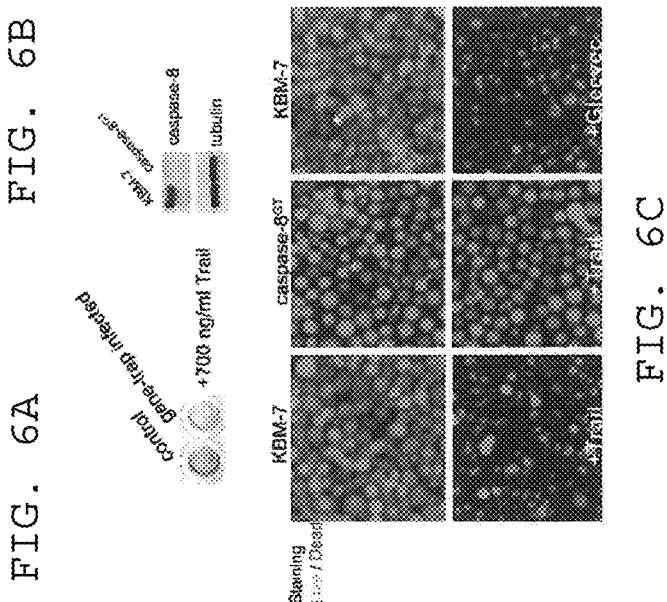
FIG. 6A shows identification of TRAIL resistant gene-trap knockouts that grow and acidify the culture medium.
FIG. 6B is a Western blot analysis of cells that have a gene-trap integration in caspase-8.
FIG. 6C shows induction of cell death in KBM-7 cells by TRAIL and Gleevec. Caspase-8 mutant cells are resistant to TRAIL. Living cells are stained green and dead cells are stained red.

We next analyzed if the near-haploid KBM7 subclone is sensitive to TRAIL-induced apoptosis. Control cells and a small number of gene-trap mutagenized cells were cultured in the presence of 700 ng/ml TRAIL. Cell viability was decreased dramatically after a period of 2 days, while some living cells remained in the gene-trap mutagenized pool (FIG. 6A). These cells were expanded and the gene-trap integration site was identified. The cells contained a single integration in the caspase-8 locus, a gene known to be involved in TRAIL-induced apoptosis. The gene-trap was in the sense orientation and predicted to perturb caspase-8 expression. Indeed, Western-blot analysis revealed that caspase-8 protein levels were reduced to undetectable levels (see FIG. 6B). These results indicate that gene-trap screens in TRAIL-sensitive KBM7 cells can identify genetic components (e.g., genes, gene products, gene functions, and genetic pathways) critical for this induced apoptotic response. Mutations in these genes required for the induced apoptotic response may contribute to resistance to the effects of chemotherapeutic agents that act at least in part by inducing apoptosis.

The near-haploid KBM7 cells contain a Philadelphia chromosome (t(9;22)) characteristic of BCR-ABL transformed chronic myelogenous leukemia cells. Gleevec, a small molecule inhibitor of the BCR-ABL kinase activity, is a successful treatment for chronic myelogenous leukemia [27]. Therefore we asked if the KBM7 cells were sensitive to Gleevec. FIG. 6C indicates that these cells are very sensitive to Gleevec and respond homogeneously by undergoing apoptosis. These data suggest that essential gene products for TRAIL and Gleevec-mediated cytotoxicity can be revealed through genetic screens in KBM7 cells. Mutations in genes required for Gleevec-mediated cytotoxicity may contribute to resistance to this agent.

Example 10: Gene Trapping without Selection

We examined in our screening system whether it would be feasible to use gene trapping with our viruses without any selection for expression of the locus in which the virus has integrated. To address this question, we used cells that were not drug- or GFP selected prior to selection of mutants that show the desired phenotype. In studies using Anthrax and Diphtheria toxins, this approach led to the recovery of the same mutant alleles as was achieved with selection (see Example 6A), suggesting that this strategy could be used to identify mutants that have integrations in genes that are expressed at very low levels.

Another option to help avoid a bias towards highly expressed genes is the use of poly-A based gene trapping instead of a strategy based on promoterless gene trap vectors. We will modify our existing vectors so that they will carry a strong promoter such as the CMV or PGK promoter and introduce a splice donor site downstream of the selection marker replacing the poly-A sequence. Mutagenized cell populations using gene trapping based on these strategies will be compared with strategies employing the promoterless gene trap vectors described above in terms of efficiency and genes identified.

Example 11: Optimizing the Identification of Mutants that Show a Phenotype of Interest The identification of the spectrum of genes involved in a cellular phenotype of interest using the approach described in the above Examples may currently be limited by the number of clones that we can individually culture and use for DNA isolation and mapping of the viral integration site using inverse PCR. If the mapping procedure was more efficient, we would in principle be able to increase the number of individual mutants recovered for a phenotype of interest at least 10-100 fold by infecting a larger population of cells with our gene trap viruses. This would potentially allow us to identify more genes by increasing the likelihood of finding integrations in smaller genes or possibly genes that are expressed at lower levels using a poly-A trap gene-trap vector. Here we propose to make use of new sequencing technologies to map hundreds or thousands of integrations simultaneously using Solexa sequencing technology.

To demonstrate the feasibility of mapping multiple integrations simultaneously we will use fifty clonal cell lines for which we know the exact location of the viral integration sites, and we will mix these cells in a 1:1 in a manner such that five clones represent 10% of the population, five clones 2%, five clones 0.5% and five other clones 0.01%. Next, DNA will be isolated from that cell population and setup an inverse PCR reaction using increasing amounts of genomic DNA ranging from 10 ng to 1 μg. A nested inverse PCR will be performed using primers containing Solexa adapter sequences that are designed to anneal very close to the junction of the virus LTR with the genomic DNA. This material will be used for Solexa sequencing. The sequences obtained will be mapped to the human genome and since we will know the exact input of the integration sites and their abundance, we can determine how large the population of clones can be that we can analyze in a single mapping reaction using Solexa sequencing.

Example 12: Generation of a New Cell Type and Identification of Host Factors for Poliovirus We wished to obtain an additional cell type suitable for haploid genetics. A method that has recently been described allowing reprogramming of the differentiated cell state employs the introduction of pluripotency-inducing transcription factors OCT4, SOX2, KLF4 and c-Myc [26]. As far as we are aware this method has not been used in cultured human cancer cell lines. We tested whether cellular reprogramming was able to alter the differentiated cell state of hematopoietic KBM7 cells. Introduction of the four transcription factors resulted in the formation of adherent cell clones. Some or most of these clones lost the hematopoietic cell surface markers CD43 and CD45. The majority of these cells were not pluripotent and HAP1 cells could be cultured in medium containing 10% FCS and could be expanded using trypsin. These cells were not hematopoietic and the majority of these cells had a single copy of each chromosome including chromosome 8.

Figure 5:
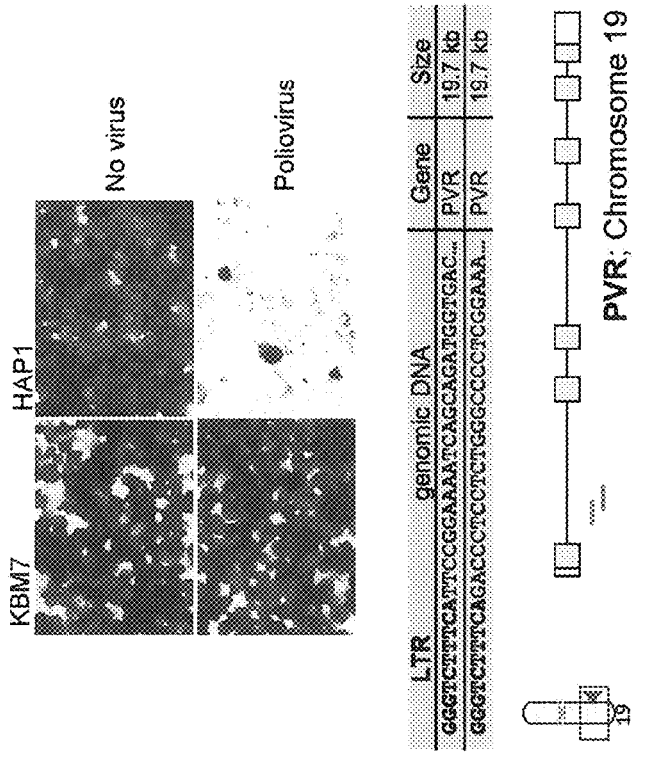
FIG. 5 shows infection of KBM7 and HAP1 cells with high titer poliovirus results in cell death in HAP1 cell population. Mutagenized cell clones that are resistant contain integrations in the poliovirus receptor PVR (SEQ ID NOS: 49-50, respectively).

Next we asked if this new cell type could be used to study biology that cannot be studied in KBM7 cells. In contrast to influenza virus, KBM7 cells cannot be productively infected with poliovirus (FIG. 5). HAP1 cells however, are very susceptible to poliovirus infection and undergo massive cell death within a few days. Subsequently, fresh HAP1 cells were infected with our gene trap retroviral construct and exposed to poliovirus. Two resistant colonies were expanded and the integrations were mapped. As indicated in FIG. 5, both mutants contained independent integrations in the known poliovirus entry receptor, PVR, thus explaining their resistance. These results indicate that factors essential for poliovirus infection can be found through haploid genetic screens in reprogrammed, non-hematopoietic cell lines derived from KBM7 cells. In addition, they demonstrate the utility of reprogramming techniques to generate cells with phenotypes of interest other than pluripotency (e.g., adherence, altered susceptibility to pathogens).

Example 13: Creation of New Near-Haploid Cell Types

As described in Example 12, the differentiated cell state of KBM7 cells can be altered though reprogramming mediated by the transcription factors c-Myc/OCT4/SOX2 and KLF4. This approach has yielded at least one new non-hematopoietic cell type that allows the study of at least some biological questions that cannot be addressed in KBM7 cells. We will generate and characterize additional non-hematopoietic cell lines derived from KBM7 cells using reprogramming. In some cases we will use other reprogramming genes or transcription factors or small molecules that stimulate cell reprogramming and/or non-integrating delivery strategies to supply the cells with reprogramming factors.

In the experiments described in Example 12, we used the vector system that had been used before successfully by others to reprogram somatic cells [26]. These retroviral vectors integrate into the genome, resulting in potential inactivation of gene sequences and continuous expression of these 4 factors as long as the retroviral vectors do not undergo silencing. To avoid these potential issues, non-hematopoietic cell types are generated using non-integrating adenoviral vectors expressing the four factors [30]. In an alternative approach, the four factors are transduced into near-haploid KBM7 cells using a modified retroviral expression vector that contains LoxP sequences in the LTR so that it allows excision of the introduced gene sequences when cells have reached an epigenetically stable altered differentiation state. We have already verified that recombination between LoxP sites takes place efficiently in our cell type upon infection with an Adeno-Cre virus.

Multiple (e.g., five) independently derived non-hematopoietic cell lines are characterized using gene expression analysis to elucidate what cell type they resemble. Microarray gene-expression profiles of KBM7 cells and the non-hematopoietic derived cell lines are generated and compared to publicly available gene expression patterns from 61 different pure cell cultures of different tissue origin (NCBI GEO accession GDS1402) or a gene expression atlas of the human genome derived from 79 different tissues (NCBI GEO accession GDS 594). This will allow identification of differentiated cell states that the non-hematopoietic cell clones most closely resemble.

Multiple (e.g., twenty) independently derived non-hematopoietic cell lines are characterized using karyotyping to identify cell populations that contain the most cells that are haploid for all chromosomes, including chromosome 8.

Example 14: Creation of Near-Haploid iPS Cells

To generate near-haploid iPS cells, KBM7 cells are infected with viruses that express OCT4/SOX2/KLF4 and c-Myc, and clones are expanded in growth conditions that are optimal for human ES cells, using mouse feeder cells, b-FGF and knockout serum replacement. Colonies that have the morphology of human ES cell clones are expanded, and the expression of markers for pluripotency is examined. Clones that express markers associated with pluripotency such as Tra-1-81, Lin-28, Nanog and/or alkaline phosphatase activity are karyotyped to determine whether they have maintained the near-haploid chromosome number and are be injected into mice to determine if these cells are pluripotent and able to give rise to tumors that contain cell types derived of each germ layer. Near-haploid pluripotent cells would allow the generation of many different cell types for future genetic screens. Notably, we have already observed the appearance of ES-like colonies that were positive for alkaline phosphatase (a marker used for human and mouse ES cells) in the experiments described in Example 12.

Example 15: Simultaneous Mapping of Multiple Insertion Sites

In examples described above, cells were subcloned prior to identification of the insertion site and mapping occurred on a one by one basis. The ability to efficiently map a multitude of insertion sites in a pool of cells that have been selected for a certain cellular phenotype would greatly expedite analysis. In addition this would allow enrichment screens or depletion screens in which the selection for the phenotype is less stringent than, for example, a screen based on cytotoxicity. To increase the number of insertions that can be mapped simultaneously, we set out to adapt the inverse PCR protocol mentioned in Example 5 to be used with massively parallel sequencing techniques. Genomic DNA was isolated from 30 million cells that had been infected with a gene trap vector. Four digestion reactions were performed per sample, two using NlaIII and two using MseI. Subsequently the digested DNA was column-purified (Qiagen) and 1 microgram DNA was ligated in a volume of 300 microliter using T4 DNA ligase (NEB) at room temperature overnight. After another round of column purification the DNA was used as template for an inverse PCR with outward facing primers. The oligonucleotides were designed to contain adaptor sequences required for use with the "Illumina Genome Analyzer", a massively parallel sequencing platform. Oligonucleotides used were: 5'-AATGA-TACGGCGACCACCGAGATCT-GATGGTTCTCTAGCTTGCC-3' (SEQ ID NO: 142) 5'-CAAGCAGAAGACGGCATACGACCCAGGTTAA-GATCAAGGTC-3' (SEQ ID NO: 143) for templates digested with NlaIII. Oligonucleotides used were: 5'-AAT-GATACGGCGACCACCGAGATCT-GATGGTTCTCTAGCTTGCC-3' (SEQ ID NO: 144) 5'-CAAGCAGAAGACGGCAT-ACGACGTTCTGTGTTGTCTCTGTCTG-3' (SEQ ID NO: 145) for templates digested with MseI. The four PCR reactions were pooled and used for analysis on an Illumina Genome Analyzer according to manufacturer's protocol. Typically ~20,000 insertions sites mapping to different positions on the human genome are obtained from this analysis. To facilitate identification of genomic loci that are enriched for gene trap insertions "insertion density" can be plotted in a graph. Insertion density is determined for every insertion by calculating 1/(average distance to three following insertions sites). FIG. 7 shows an example from such an analysis. The regions with high insertion density potentially indicate genomic regions containing genes whose knockout lead to the probed phenotype. It is immediately seen that 4 loci confer resistance.

REFERENCES

1. Berns, K., Hijmans, E. M., Mullenders, J., Brummelkamp, T. R., Velds, A., Heimerikx, M., Kerkhoven, R. M., Madiredjo, M., Nijkamp, W., Weigelt, B., Agami, R., Ge, W., Cavet, G., Linsley, P. S., Beijersbergen, R. L., and Bernards, R. (2004). A large-scale RNAi screen in human cells identifies new components of the p53 pathway. Nature 428, 431-437.
2. Brummelkamp, T. R., and Bernards, R. (2003). New tools for functional mammalian cancer genetics. Nat Rev Cancer 3, 781-789.
3. Brummelkamp, T. R., Nijman, S. M., Dirac, A. M., and Bernards, R. (2003). Loss of the cylindromatosis tumour suppressor inhibits apoptosis by activating NF-kappaB. Nature 424, 797-801.
4. Nijman, S. M., Huang, T. T., Dirac, A. M., Brummelkamp, T. R., Kerkhoven, R. M., D'Andrea, A. D., and Bernards, R. (2005). The deubiquitinating enzyme USP1 regulates the Fanconi anemia pathway. Mol Cell 17, 331-339.
5. Brummelkamp, T. R., Fabius, A. W., Mullenders, J., Madiredjo, M., Velds, A., Kerkhoven, R. M., Bernards, R., and Beijersbergen, R. L. (2006). An shRNA barcode screen provides insight into cancer cell vulnerability to MDM2 inhibitors. Nat Chem Biol 2, 202-206.
6. Jackson, A. L., Bartz, S. R., Schelter, J., Kobayashi, S. V., Burchard, J., Mao, M., Li, B., Cavet, G., and Linsley, P. S. (2003). Expression profiling reveals off-target gene regulation by RNAi. Nat Biotechnol 21, 635-637.
7. Ma, Y., Creanga, A., Lum, L., and Beachy, P. A. (2006). Prevalence of off-target effects in Drosophila RNA interference screens. Nature 443, 359-363.
8. Pebernard, S., and Iggo, R. D. (2004). Determinants of interferon-stimulated gene induction by RNAi vectors. Differentiation 72, 103-111.
9. Zdzienicka, M. Z., and Simons, J. W. (1987). Mutagensensitive cell lines are obtained with a high frequency in V79 Chinese hamster cells. Mutat Res 178, 235-244.

10. Adair, G. M., Stallings, R. L., Nairn, R. S., and Siciliano, M. J. (1983). High-frequency structural gene deletion as the basis for functional hemizygosity of the adenine phosphoribosyltransferase locus in Chinese hamster ovary cells. Proc Natl Acad Sci USA 80, 5961-5964.
11. Guo, G., Wang, W., and Bradley, A. (2004). Mismatch repair genes identified using genetic screens in Blm-deficient embryonic stem cells. Nature 429, 891-895.
12. Yusa, K., Horie, K., Kondoh, G., Kouno, M., Maeda, Y., Kinoshita, T., and Takeda, J. (2004). Genome-wide phenotype analysis in ES cells by regulated disruption of Bloom's syndrome gene. Nature 429, 896-899.
13. Wang, W., and Bradley, A. (2007). A recessive genetic screen for host factors required for retroviral infection in a library of insertionally mutated Blm-deficient embryonic stem cells. Genome Biol 8, R48.
14. Kotecki, M., Reddy, P. S., and Cochran, B. H. (1999). Isolation and characterization of a near-haploid human cell line. Exp Cell Res 252, 273-280.
15. Stanford, W. L., Cohn, J. B., and Cordes, S. P. (2001). Gene-trap mutagenesis: past, present and beyond. Nat Rev Genet 2, 756-768.
16. Collins, F. S., Rossant, J., and Wurst, W. (2007). A mouse for all reasons. Cell 128, 9-13.
17. Collins, F. S., Finnell, R. H., Rossant, J., and Wurst, W. (2007). A new partner for the international knockout mouse consortium. Cell 129, 235.
18. Van Ness, B. G., Howard, J. B., and Bodley, J. W. (1980). ADP-ribosylation of elongation factor 2 by diphtheria toxin. Isolation and properties of the novel ribosyl-amino acid and its hydrolysis products. J Biol Chem 255, 10717-10720.
19. Van Ness, B. G., Barrowclough, B., and Bodley, J. W. (1980). Recognition of elongation factor 2 by diphtheria toxin is not solely defined by the presence of diphthamide. FEBS Lett 120, 4-6.
20. Young, J. A., and Collier, R. J. (2007). Anthrax toxin: receptor binding, internalization, pore formation, and translocation. Annu Rev Biochem 76, 243-265.
21. Chen, C. M., and Behringer, R. R. (2005). OVCA1: tumor suppressor gene. Curr Opin Genet Dev 15, 49-54.
22. Liu, S., and Leppla, S. H. (2003). Retroviral insertional mutagenesis identifies a small protein required for synthesis of diphthamide, the target of bacterial ADP-ribosylating toxins. Mol Cell 12, 603-613.
23. Lara-Tejero, M., and Galan, J. E. (2000). A bacterial toxin that controls cell cycle progression as a deoxyribonuclease I-like protein. Science 290, 354-357.
24. Olofsson, S., and Bergstrom, T. (2005). Glycoconjugate glycans as viral receptors. Ann Med 37, 154-172.
25. Hamamoto, R., Furukawa, Y., Morita, M., Iimura, Y., Silva, F. P., Li, M., Yagyu, R., and Nakamura, Y. (2004). SMYD3 encodes a histone methyltransferase involved in the proliferation of cancer cells. Nat Cell Biol 6, 731-740.
26. Zaehres, H., and Scholer, H. R. (2007). Induction of pluripotency: from mouse to human. Cell 131, 834-835.
27. Ren, R. (2005). Mechanisms of BCR-ABL in the pathogenesis of chronic myelogenous leukaemia. Nat Rev Cancer 5, 172-183.
28. Bushman, F., Lewinski, M., Ciuffi, A., Barr, S., Leipzig, J., Hannenhalli, S., and Hoffmann, C. (2005). Genome-wide analysis of retroviral DNA integration. Nat Rev Microbiol 3, 848-858.
29. Friedel, R. H., Plump, A., Lu, X., Spilker, K., Jolicoeur, C., Wong, K., Venkatesh, T. R., Yaron, A., Hynes, M., Chen, B., Okada, A., McConnell, S. K., Rayburn, H., and Tessier-Lavigne, M. (2005). Gene targeting using a promoterless gene trap vector ("targeted trapping") is an efficient method to mutate a large fraction of genes. Proc Natl Acad Sci USA 102, 13188-13193.

30. Stadtfeld, M., Nagaya, M., Utikal, J., Weir, G., and Hochedlinger, K. (2008). Induced pluripotent stem cells generated without viral integration. Science 322, 945-949.

31. Tipping, A. J., Deininger, M. W., Goldman, J. M., and Melo, J. V. (2003). Comparative gene expression profile of chronic myeloid leukemia cells innately resistant to imatinib mesylate. Exp Hematol 31, 1073-1080.

32. Frank, O., Brors, B., Fabarius, A., Li, L., Haak, M., Merk, S., Schwindel, U., Zheng, C., Muller, M. C., Gretz, N., Hehlmann, R, Hochhaus, A., and Seifarth, W. (2006). Gene expression signature of primary imatinib-resistant chronic myeloid leukemia patients. Leukemia 20, 1400-1407.

Example 16

Materials & Methods

Construction of Gene Trap Vectors

Retroviral gene trap vectors that contain an inactivated 3' LTR, a strong adenoviral (Ad40) splice-acceptor site, either GFP or the puromycin resistance gene (PURO) and SV40 polyadenylation signal were constructed as follows. The coding sequence of PURO or GFP was obtained by PCR amplification with primers containing overhanging ClaI and NheI restriction sites as well as partial splice acceptor sites: (GFP:5'-GATCGCTAGCCGCATTTCTTTTTTCCA-GATGGTGAGCAAGGGCGAGG-3' (SEQ ID NO: 146) and 5'-GATCGGATCCTTACTTGTACAGCTCGTC-CATGC-3' (SEQ ID NO: 147) PURO: 5'-GATCGCTAGCCGCATTTCTTTTTTCCA-GATGACCGAGTACAAGCCCAC-3' (SEQ ID NO: 148) and 5'-GATCG-GATCCTCAGGCACCGGGCTTGCGGGTC-3' (SEQ ID NO: 149)). These PCR products were inserted in pEGFPC1 (Clontech) replacing EGFP. Subsequently PCR was per-formed to introduce the complete splice acceptor site and to obtain the marker gene including the poladenylation signal using primers: (GFP: 5'-GATCATC-GATCGCAGGCGCAATCTTCGCATTTCTTTTTTCCA-GATGG-3' (SEQ ID NO: 150) and 5'-GATCGGATCCT-TACTTGTACAGCTCGTCCATGC-3' (SEQ ID NO:151) PURO: 5'-GATCATCGATCGCAGGCGCAATCTTCG-CATTTCTTTTTTCCAGATGAC-3' (SEQ ID NO: 152) and 5'-GATCGGATCCTTACTTGTACAGCTCGTCCATGC-3' (SEQ ID NO: 153)). These PCR products were inserted in pRETRO-SUPER (1) replacing the polIII promoter. The resulting plasmids are pGT-GFP and pGT-PURO. These plasmids were used as PCR template to obtain gene trap vectors in two additional reading frames using forward primers (PURO: 5'-GATCATC-GATGCGCAGGCGCAATCTTCGCAT-TTCTTTTTTCCAGGATGACCGAGT A-3' (SEQ ID NO: 154) and GATCATCGATGCGCAGGCGCAATCTTCG-CATTTCTTTTTTCCAGGGATGACCGAG TA (SEQ ID NO: 155); GFP: 5'-GATCATC-GATGCGCAGGCGCAATCTTCGCAT-TTCTTTTTTCCAGGATGGTGAGCA AG-3' (SEQ ID NO: 156) and 5'-GATCATC-GATGCGCAGGCGCAATCTTCGCAT-TTCTTTTTTCCAGGGATGGTGAGC AAG-3' (SEQ ID NO: 157)) with reverse primer (AATTAGATCTTTACAAT-TTACGCG (SEQ ID NO: 158)). These PCR products were inserted in pRETRO-SUPER replacing the polIII promoter.

The resulting plasmids with +1 and +2 reading frames compared to the original vectors were called pGT+1-GFP, pGT+2-GFP, pGT+1-PURO and pGT+2-PURO.

Tissue Culture, Virus Production, and Generation of Mutant Library

293T, U205, HeLa and Swiss 3T3 were obtained from ATCC and were maintained in DMEM supplemented with 10% FCS. KBM-7 cells (generously provided by Dr. Brent Cochran, Tufts University School of Medicine, Boston, MA) were maintained in IMDM supplemented with 10% FBS and antibiotics. Gene trap virus was produced by transfection of 293T cells in T175 dishes with either pGT-GFP or pGT-PURO combined with retroviral packaging plasmids. The virus-containing supernatant was concentrated using ultra-centrifugation for 1.5 h at 25,000 r.p.m. in a Beckman SW28 rotor. Batches of mutant KBM7 cells were typically made by infection of one 24-well tissue culture dish containing 1.5 million cells per well using spin infection for 45 minutes at 2,000 rpm. Cells infected with the gene trap containing the puromycin resistance gene were selected 2 days after infec-tion using 0.5 µg/ml puromycin. After selection, cells were expanded and frozen down for further screens. The GFP gene trap infected cells were directly used for screens or first selected using FACS sorting for GFP-expressing cells. Screens were started at least 6 days after gene trap infection.

Screens

In general, mutagenized KBM7 cells were resuspended in medium containing the appropriate concentration of screen-ing agent and plated at 20,000 cells per well in a 96-well tissue culture plate. The cells were incubated for two to three weeks after which resistant cells formed clearly visible colonies. Because typically less than one colony was present per well, most of the picked colonies were clonal and used to map insertion sites.

Mapping of Insertion Sites

The host sequences flanking the proviral insertion site were determined using an inverse PCR protocol. Genomic DNA was isolated from 5 million cells using the QiaAmp DNA mini kit (Qiagen) and 4 µg was digested with NlaIII or MseI. After spin column purification (Qiagen), 1 µg digested DNA was ligated using T4 DNA ligase in a volume of 300 µl. The reaction mix was purified using spin columns and used in a PCR reaction with primers annealing to internal sequences in the gene trap vector (5'-CTGCAG-CATCGTTCTGTGTT-3' (SEQ ID NO: 159) and 5'-TCTC-CAAATCTCGGTGGAAC-3' (SEQ ID NO: 160)). The resulting PCR products that include the flanking sequence were sequenced using (5'-CTCGGTGGAACCTCCAAAT-3' (SEQ ID NO: 161)).

Construction of Retroviral and Lentiviral Vectors for Complementation

Different retroviral and lentiviral expression systems were used. pLIB-IRESpuro-GLUE was used to express WDR85 and EF2 as C-terminal fusions with an affinity tag. First, the IRESpuro-GLUE cassette was PCR amplified from pIRE-Spuro-GLUE (S. Angers et al., Nature Cell Biology 8: 348 (April 2006)); generously provided by Dr. Randall Moon, University of Washington School of Medicine, Seattle, WA) with primers containing SfiI and ClaI overhanging restric-tion sites (5'-GATCGGCCATTAAGGCCTTAATTAAGC-CACCATGGACG-3' (SEQ ID NO: 162) and 5'-GATCATC-GATAGTCGGTGGGCCTCGGGGGGCG-3' (SEQ ID NO: 163)) and the PCR product was inserted in the retroviral expression vector pLIB (Clontech) to obtain pLIB-IRE-Spuro-GLUE. The coding sequences of WDR85 and EF2 were PCR-amplified from cDNA derived from KBM-7 cells using primers with Nod overhanging restriction sites (WDR85: 5'-GATCGCGGCCGC-GATGGGCTGTTTCGCCCTGCAAACG-3' (SEQ ID NO: 164) and 5'-GATCGCGGCCGCTCAGTTCCCCTCC-CACTCCCAGAG-3' (SEQ ID NO: 165), EF2: 5'-GATCGCGGCCGCGGTGAACTTCACGGTAGACCA-GATC-3' (SEQ ID NO: 166) and 5'-GTACGCGGCCGCC-TACAATTTGTCCAGGAAGTTGTCC-3' (SEQ ID NO: 167)). The PCR products were inserted in pLIB-IRESpuro-GLUE. pWZL-hygro-HA was used to express TMEM181 as N-terminal fusion with the HA epitope. First the HA epitope was inserted in the retroviral expression vector pWZLhygro using EcoRI and SalI and annealed oligonucleotides (5'-AATTCAATACCCCTACGACGTGCCCGAC-TACGCCTAAG-3' (SEQ ID NO: 168) and 5'-TCGACT-TAGGCGTAGTCGGGCACGTCGTAGGGGTATTG-3' (SEQ ID NO: 169)) The coding sequence of TMEM181 was PCR amplified using primers containing overhanging BstXI restriction sites (5'-GG-GATCCCAGTGTGGTGGCCGAGATG-GAGCCGCTGGCG-3' (SEQ ID NO: 170) and 5'-CC-GATCCCACCACACTGGGTCACTATCTGACTCCTCC-TTG-3' (SEQ ID NO: 171)) and inserted in the resulting plasmid. pMXsIRESblast-FLAG was used to express candidates as C-terminal fusions with the FLAG epitope. First the FLAG epitope was inserted in the retroviral expression vector pMXsIRESblast (Cell Biolabs) using EcoRI and BamHI and annealed oligonucleotides (5'-GATCG-GATCCTCCACCATGGATTACAAGGATGACGACGA-TAAGCCACCAGACTG GGAATTCGATC-3' (SEQ ID NO: 172) and 5'-GATCGAATTCCCAGTCTGGTGGCT-TATCGTCGTCATCCTTGTAATCCATGGTGGA GGATCCGATC-3' (SEQ ID NO: 173)) to obtain pMX-sIRESblast. The coding sequences of SGMS1, CMAS and TMEM181 were PCR amplified using primers containing overhanging BstXI restriction sites (SGMS1: 5'-GATCC-CACCAGACTGGAAGGAAGTGGTTTATTGGTCAC-3' (SEQ ID NO: 174) and 5'-GATCCCAGTCTGGTGGT-TATGTGTCATTCACCAGCCG-3' (SEQ ID NO: 175), CMAS: 5'-GATCCCACCAGACTGGGACTCGGTG-GAGAAGGGG-3' (SEQ ID NO: 176) and 5'-GATCCCAGTCTGGTGGCTATTTTTGGCATGAATT-ATTAACC (SEQ ID NO: 177), TMEM181: 5'-GATCC-CACCAGACTGGGAGCCGCTGGCGCCCATG-3' (SEQ ID NO: 178) and GATCCCAGTCTGGTGGTCAGTCAC-TATCTGACTCCTCCTTG (SEQ ID NO: 179)). The PCR products were inserted in pMXsIRESblast. The coding region of SLC35A2 was PCR amplified using primers containing overhanging XbaI and NheI restriction sites (5'-GATCTCTAGAGAATTCAC-CATGGCAGCGGTTGGGGCTGGTG-3' (SEQ ID NO: 180) and 5'-ACTGGCTAGCCTT-CACCAGCACTGACTTTGG-3' (SEQ ID NO: 181)) and inserted in a bicistronic lentiviral vector encoding RFP (generously provided by Dr. Marius Wernig, Whitehead Institute for Biomedical Research, Cambridge, MA).
Cell Viability Assays for Toxin Treatments
KBM-7 wild type or mutant cells were seeded at 20,000 cells per well in a 96-well tissue culture plate and treated with indicated concentrations of toxin or left untreated. Four days after treatment cell viability was measured using a XTT colorimetric assay (Roche) according to manufacturers protocol. Viability is plotted as percentage viability compared to untreated control. To evaluate the effect of TMEM181 overexpression in Hela, U2OS or Swiss 3T3 cells, cells were transduced with retroviral vector pMxIRESblast-FLAGT- MEM181. Polyclonal populations were derived after selection with 25 µg/ml Blasticidin (invivogen). Cells were plated at 10,000 cells per well in a 24-well tissue culture plate and one day after seeding treated with indicated concentrations cdt holotoxin. Six days after treatment, viable, adherent cells were fixed with 4% formaldehyde in PBS followed by a 30 minutes staining with 0.5% crystal violet dye in 70% ethanol. After three gentle washes with water, air-dried plates were scanned. To determine viability quantitatively, cells were seeded at 2,000 cells per well in a 96-well plate and after one day treated with cdt. Six days after treatment indicated concentrations of toxin or left untreated. Four days after treatment cell viability was measured using a XTT colorimetric assay (Roche) according to manufacturers protocol.
Cell Cycle Analysis
For cell cycle analysis, KBM7 wild type and mutant cells were seeded at 0.5 million cell per well in a 24-well tissue culture plate and treated with indicated concentrations cdt. Twenty-four hours after intoxication, cells were processed for flow cytometry as follows. Cells suspensions were centrifuged and supernatants were removed, and the cell pellets were resuspended in 200 µl staining solution (propidium iodide 50 µg/ml in 0.1% sodium citrate plus 0.1% triton X-100). After incubation for 60 minutes on ice, the stained cells were analyzed by flow cytometry with a FACS LSR flow cytometer (Beckton Dickinson).
Western Blots Analysis to Determine Expression in Gene Trap Mutants
Cells were lysed directly in Laemmli sample buffer, separated on a NuPAGE Novex 4-12% Bis-Tris gel (Invitrogen), and transferred to a polyvinylidene difluoride membrane (Millipore) Immunoblots were processed according to standard procedures, using primary antibodies for HPRT (Abcam), FADD (FD19, Santa Cruz), Caspase 8 (Santa Cruz), NF1 (Santa Cruz), CDK4 (C-22, Santa Cruz), actin (Santa Cruz) and CMAS (abcam).
RT PCR to Determine Expression in Gene Trap Mutants
Total RNA was prepared as described in the RNeasy Mini Kit (Qiagen, Valencia, CA) with on-column DNase I digestion. One microgram total RNA from each sample was used for Oligo(dT)20-primed reverse transcription, which was carried out as described in the product protocol (Super-Script™ III First-Strand Synthesis System for RT-PCR, Invitrogen). PCR was performed using AccuPrime™ Taq DNA Polymerase High Fidelity using 28 PCR cycles. PCR primer sequences are WDR85 (5'-CAGCCCTTGAAGAT-CATCAGC-3' (SEQ ID NO: 182) and 5'-GCCAGTAATT-GAAAGCAGCAATC-3' (SEQ ID NO: 183)) SLC35A2 (CTCACAGGCGCCTGAAGTAC (SEQ ID NO: 184) and GGAAAGTGGCAGCTGGTAG (SEQ ID NO: 185)).
MEK Cleavage
To test whether MEK cleavage could occur in WDR85 mutant cells, anthrax protective (List Biologicals) was combined with anthrax lethal factor (LF; List Biologicals) and added to cells in final concentrations of 600 ng and 150 ng/ml, respectively. After 90 minutes incubation at 37° C., cells were lysed in Laemmli sample buffer separated on a NuPAGE Novex 4-12% Bis-Tris gel (Invitrogen), and transferred to a polyvinylidene difluoride membrane (Millipore) Immunoblots were processed according to standard procedures, using primary antibodies against MEK-3 (C-19 Santa Cruz).
Cell Treatment with Imatinib, 6-Thioguanine or TRAIL
For the antimetabolite 6-thioguanine (Sigma Aldrich) a concentration of 20 µM was used during the complete incubation period. For imatinib (Novartis) a concentration of 1 µM was used during four days followed by dilution to 300 nM for the following two weeks. Recombinant TRAIL (Sigma Aldrich) was added at a concentration of 1 µg/ml to 2 million cells in a 24-wells plate. After one week cells were plated in one 96-well plate, thereby diluting TRAIL 20-fold.

Diphtheria, LFN-DTA and CDT Treatment

For diphtheria toxin (Sigma Aldrich) a concentration of 400 ng/ml was used during the complete incubation period. LFN-DTA used in the anthrax screen was purified from *E. coli* transformed with pET-15b LFN-DTA (Milne et al., *Molecular Microbiology* 15: 661 (February 1995)); generously provided by Dr. John Collier, Harvard Medical School, Boston, MA) using Ni-NTA agarose (Qiagen) according to manufacturers protocol. This protein was combined with anthrax protective antigen (PA; List biologicals) to final concentrations of 600 ng and 150 ng/ml for PA and LFN-DTA, respectively. *E. Coli* derived cytolethal distending toxin was produced from plasmid pDS7.96 (Scott & Kaper, *Infection and Immunity* 62: 244 (January 1994)); generously provided by Dr. James Kaper, University of Maryland School of Medicine, Baltimore, MD). Filter-sterilized medium supernatant of DH5a strain transformed with the plasmid was concentrated to 5 µg total protein per µl. For the screen cytolethal distending toxin was used at a concentration of 5 µg/ml during the complete incubation period.

Influenza Infections

One million wild type or mutant KBM7 cells were incubated with 50,000 HA units of sucrose gradient purified influenza A/PR/8/34 virus (Charles River) in 100 µl serum free IMDM medium for 1 hour at room temperature. Subsequently, cell were taken up in IMDM medium containing 5 µg/ml trypsin and plated in a well of a 24-well tissue culture plate. Twelve hours after infection, cells were fixed with 4% formaldehyde in PBS, permeabilized with 0.1% Triton X-100 and stained using primary antibodies raised against influenza virus A nucleoprotein (AA5H, Abcam). Because viral proteins accumulate to detectable levels only when replication of the virus takes place, the percentage of fluorescent cells is considered to correspond to the percentage of infected cells. The percentage was calculated by counting ~200 cells per infection cells in four randomly chosen microscopic fields.

Lysenin Treatment

KBM7 wild type or mutant cells were incubated with 500 ng/ml lysenin from *Eisenia foetida* (Sigma Aldrich). Subsequently, cell viability was determined immediately using the LIVE/DEAD® Viability/Cytotoxicity Kit (Invitrogen) that is based on cellular integrity. Alternatively, the cells were plated at 30,000 cells per well in a 96 well tissue culture plate and two days after treatment viability was determined using a XTT colorimetric assay (Roche) according to manufacturers protocol.

Interaction of CDT with TMEM181

Anti-Flag M2 beads (Sigma) resuspended in 2 ml NETN buffer (50 mM Tris-HCl pH 7.8, 150 mM NaCl, 1 mM EDTA-NaOH, 1% (v/v) Nonidet P-40, supplemented with protease inhibitors) were incubated with 400 µl concentrated filter-sterilized medium supernatant of DH5alpha cells or DH5alpha cells expressing a FLAG-tagged version of CDT (tag introduced downstream to the signal secretion peptide of subunit CDTA, by site-directed mutagenesis (Stratagene)). After overnight incubation at 4° C. in an end-over-end shaker the beads were washed 3x with NETN buffer. Washed beads were incubated with cell lysates of KBM-7 cells and KBM-7 cells overexpressing HA-TMEM181 lysed in CHAPS lysis buffer (20 mM Tris pH 8.0, 100 mM NaCL, 1 mM EDTA, 0.3% CHAPS) in the presence of protease inhibitors. After centrifugation to remove insoluble material, the samples were halved and equal amounts of either control or FLAG-CDT-coupled beads were added. After 6 hours of incubation the beads were washed 4x with CHAPS lysis buffer, and protein complexes were eluted using 3×Flag peptide (Sigma) and analyzed by immuno-blotting.

Purification EF2

109 KBM-7 cells or KBM-7 cells infected with pLIB-Glue-EF2 were lysed in NETN buffer (150 mM NaCl, 1 mM EDTA, 50 mM Tris-HCl (pH 7.8), 1% Nonidet P-40) containing protease inhibitors (Roche) and protein complexes were purified using streptavidin sepharose (Amersham) and eluted using 50 mM biotin. Proteins were separated using SDS-PAGE gel electrophoreses and visualized using silverstaining. For mass spectrometry, the EF2 band was purified from gel and digested using trypsin.

In Vitro Ribosylation and In Vitro Methylation of EF2

In vitro ribosylation of EF2 was carried out in RIPA lysis buffer containing protease inhibitors using 5 ng LFN-DTA and 2.5 µM NAD-Biotin (Trevigen). Reactions were incubated for 45 minutes at 30° C. For in vitro methylation of 'intermediate' EF2 DPH5 mutant cells expressing pLIB-Glue-EF2 were lysed in M-buffer (30 mM TrisH·Cl (ph 7.5), 15 mM KCl, 5 mM MgAc, 6 mM β-mercaptoethanol and 0.5% NP40) containing protease inhibitors and EF2 was purified using streptavidin beads. Beads were washed twice using M-buffer and incubated with cell lysates derived from wild type cells and WDR85 and DPH5 deficient cells lysed in M-buffer. 5 µCi H3-AdoMet was added per reaction and the reactions were incubated at 30° C. for 60 minutes.

Results

Development of a New Approach for Loss of Function Genetics in Human Cells

To facilitate mutagenesis-based genetic approaches in human cells, we use a unique derivative of the KBM-7 CML cell line with a haploid karyotype except for chromosome 8 (7) (See FIG. 8A). In this cell line, gene inactivation should allow the generation of null alleles for most non-essential genes. We chose to inactivate genes using insertional mutagenesis, because this approach is highly mutagenic in a variety of organisms, and the integrated DNA sequences provide a molecular tag to quickly identify the disrupted gene. We used gene trap retroviruses that contain a strong adenoviral splice acceptor site and a marker gene (GFP or puromycin-resistance gene) in reverse orientation of the retroviral backbone (see supplemental methods). To examine whether gene trap insertions are indeed mutagenic, a pilot screen was performed with the nucleotide analogue 6-thioguanine (6-TG), converted to a toxic metabolite by the enzyme HPRT (hypoxanthine-guanine phosphoribosyltransferase). The gene trap virus was titrated to obtain a single viral integration in the majority of the infected cells. Cell lines resistant to 6-TG were recovered and the unique sequences of the proviral/host junctions indicated that five independent mutants carried insertions in intron 1 of the X-linked HPRT gene (FIG. 8B). We performed two genetic screens to target autosomal genes. KBM-7 cells are sensitive to the tumor necrosis factor ligand TRAIL and to inhibition of the BCR-ABL oncogenic fusion protein by the kinase inhibitor Gleevec. Gene trap-mutagenized KBM7 cells were exposed to either TRAIL or Gleevec and resistant mutants were recovered. Five TRAIL resistant clones showed independent insertions in Caspase-8 and two independent insertions in FADD, genes known to be required for TRAIL-induced apoptosis (8) (FIG. 8D). Resistance to TRAIL was confirmed in these mutants (FIG. 8C). Five independent Gleevec-resistant mutants contained insertions in NF1 and one in PTPN1; both genes play an important role in the response of CML cells to Gleevec (9). One insertion was found in PTPN12, a tyrosine phosphatase that interacts with c-abl and negatively regulates its activity (10). Our screen thus suggests that PTPN12 is critical for Gleevec sensitivity. All insertions were in the same transcriptional orientation as the target gene and immunoblot analysis of HPRT, FADD, Caspase-8 and NF-1 mutant cells failed to detect the corresponding gene products (FIG. 8C). The haploid background of KBM7 thus enables the generation of mutant alleles for autosomal genes and pinpoints genes involved in the biological processes under study.

Identification of Host Factors Required for CDT

Figures 9A, 9B, 9C, 9D, 9E, 9F:
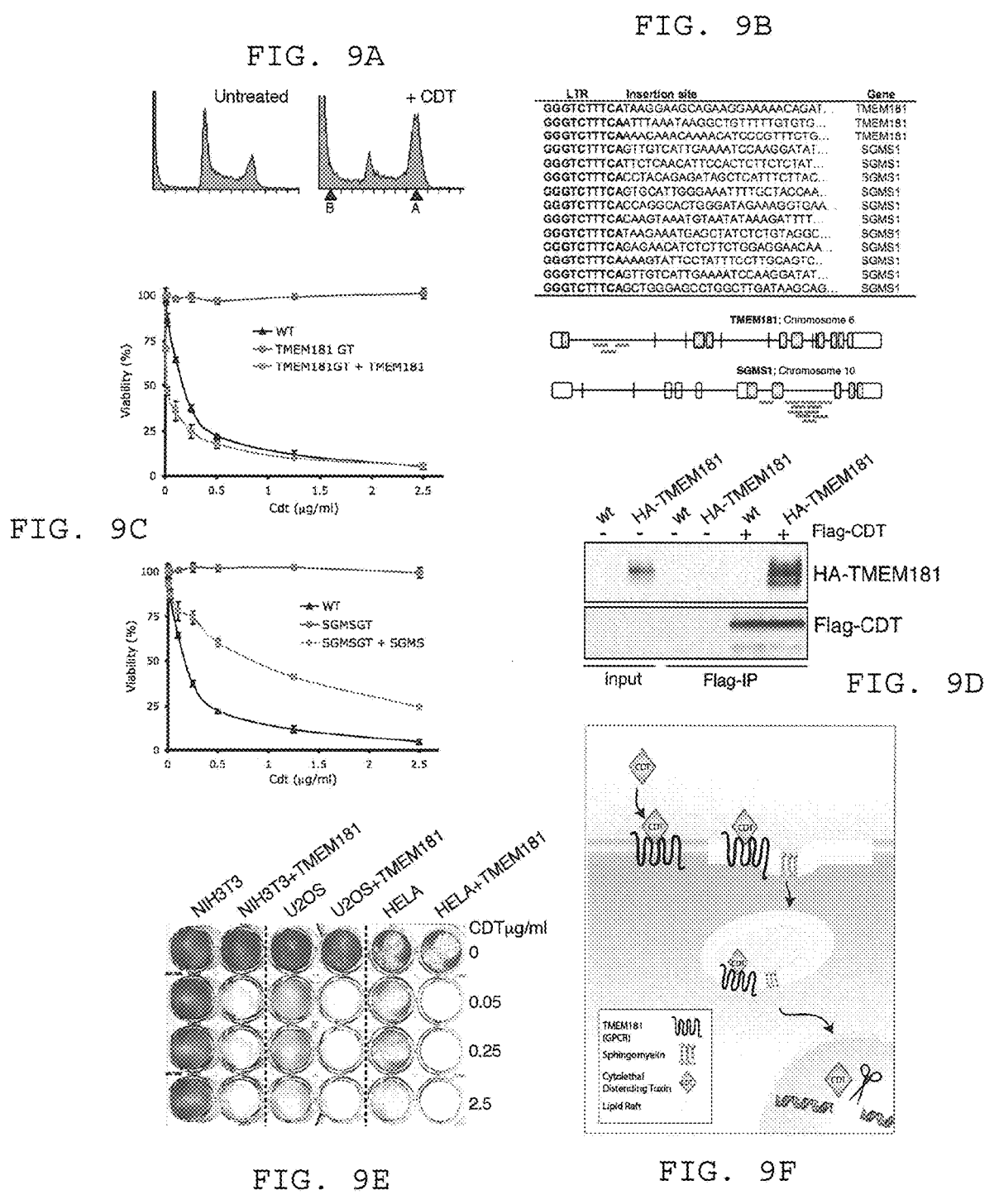
Figure 13:
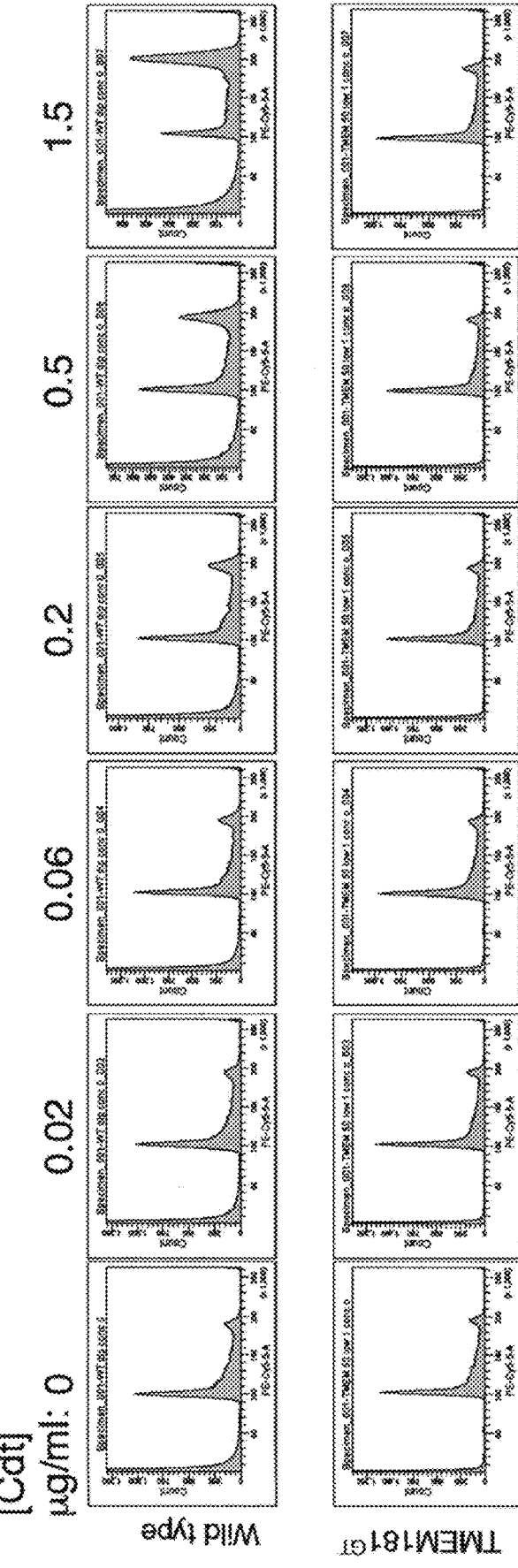
FIG. 13 shows CDT-induced accumulation of cells in the G2/M-phase of cell cycle requires TMEM181 and SGMS1, as illustrated by flow cytometric analysis of cells treated with increasing concentrations of CDT for 48 hours. The same mutant cells infected with a retrovirus or lentivirus expressing the mutated gene products regained responsiveness to toxin treatment.
Figure 13:
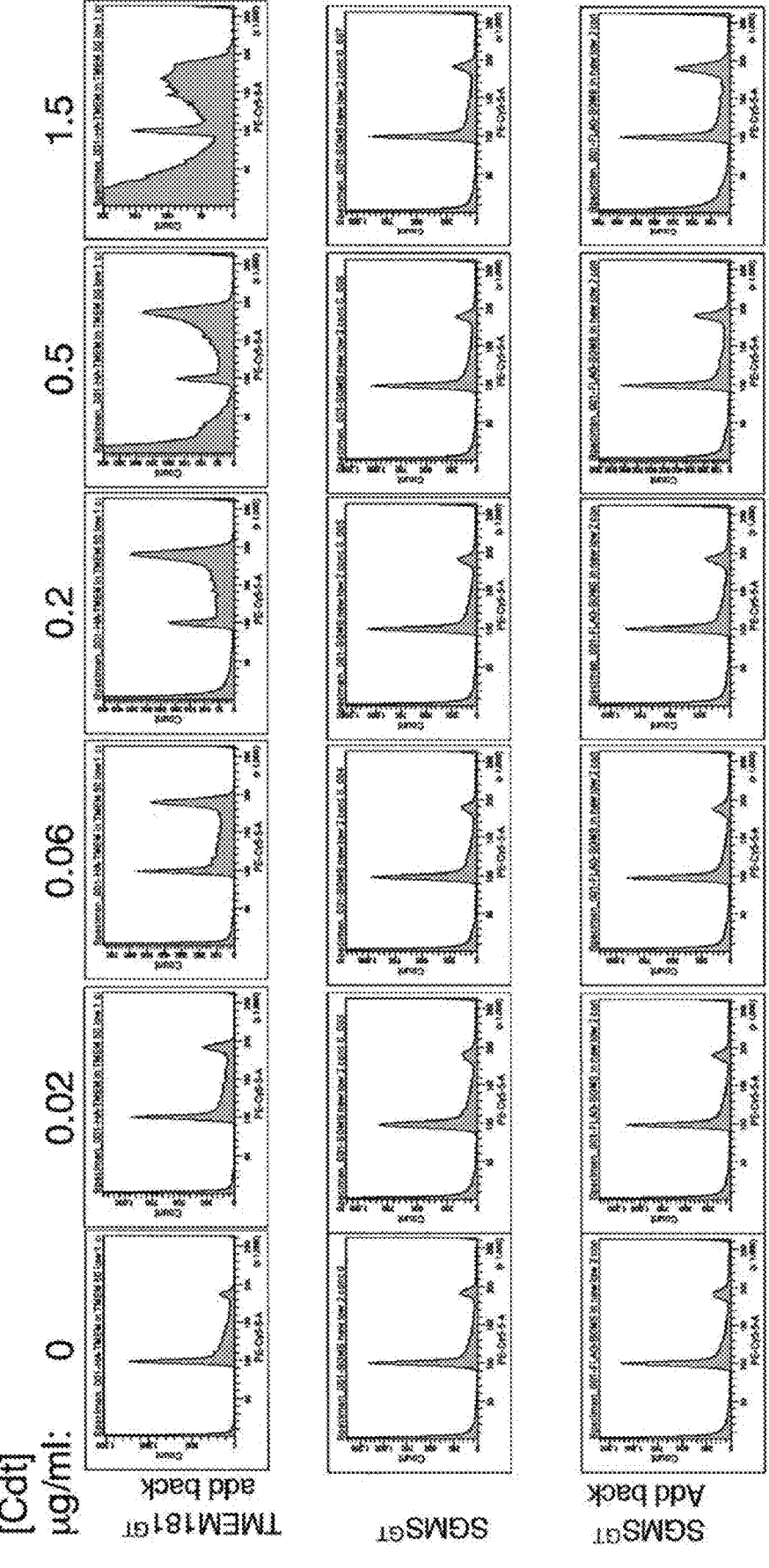
Figure 14A:
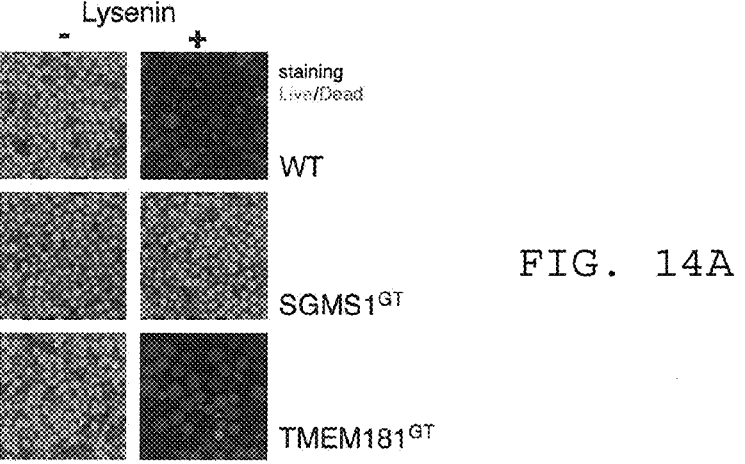
As shown in FIG. 14A, wild type cells and mutant cells for SGMS1 and TMEM181 were exposed to the pore-forming lysenin toxin, and cell viability was monitored using a vital stain.
Figure 14B:
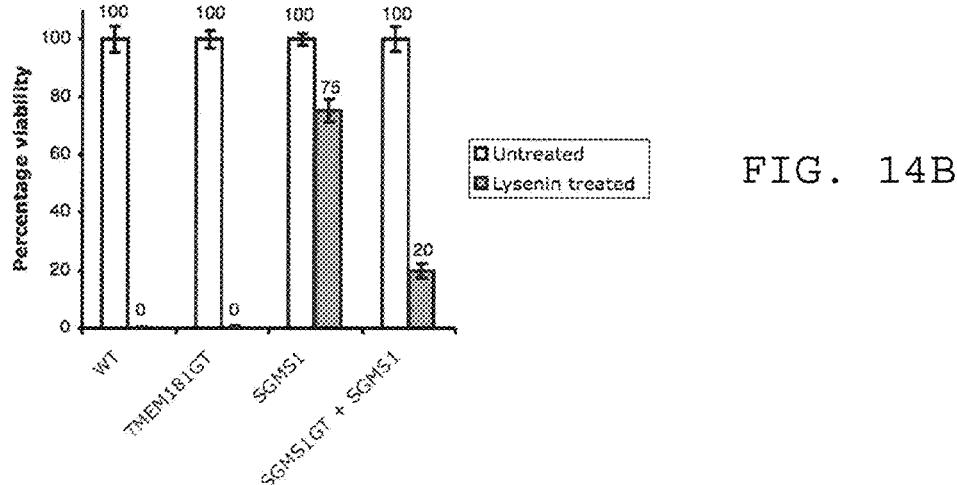
FIG. 14B illustrates results when the same cells were treated with lysenin toxin and cell viability was quantified. SGMS1 mutant cells infected with a lentiviral vector expressing SGMS1 partially regained sensitivity to the toxin.

Because many pathogenic agents such as bacterial toxins or viruses readily kill the cells they target, the large-scale production of knockout alleles for human genes may allow the identification of host factors essential for pathogenesis, such as enzymes that create structures recognized by toxins or viruses, or the receptors themselves. Several pathogenic bacteria such as *Escherichia coli, Shigella dysenteriae, Actinobacillus actinomycetemcomitans, Campylobacter jejuni, Helicobacter* spp., *Salmonella typhi* and *Haemophilus ducreyi* share a potent bacterial toxin named cytolethal distending toxin (CDT). The DNAse I-like CdtB subunit of these remarkable toxins enters the nucleus and causes cytotoxicity by inducing DNA breaks (11, 12). So far, no membrane receptor or other essential host genes have been identified that explain entry or action of CDT. KBM7-cells respond to *E. coli*-derived CDT in stereotypical fashion by undergoing an arrest in the G2/M-hase of the cell cycle (FIG. 9A) that precedes cell death. Mutagenized KBM7 cells were treated with CDT and resistant clones were isolated. Eleven independent insertions in sphingomyelin synthase 1 (SGMS1) and three insertions in TMEM181, a gene that encodes a putative G-protein coupled receptor (GPCR) (14,15), were recovered (FIG. 9B). SGMS1 and TMEM181 mutants were resistant to CDT, a phenotype reverted by complementing the mutant cells with the corresponding cDNAs (FIG. 9C and FIG. 13). The SGMS1 mutation reduced levels of sphingomyelin as verified by treatment of cells with lysenin, a sphingomyelin-specific pore-forming toxin (FIGS. 14A and 14B). Sphingomyelin is a key component of lipid rafts: depletion of SGMS1 activity disturbs lipid raft function and prevents receptor clustering (13), a trait of possible relevance for CDT binding and/or entry.

Figures 15A, 15B:
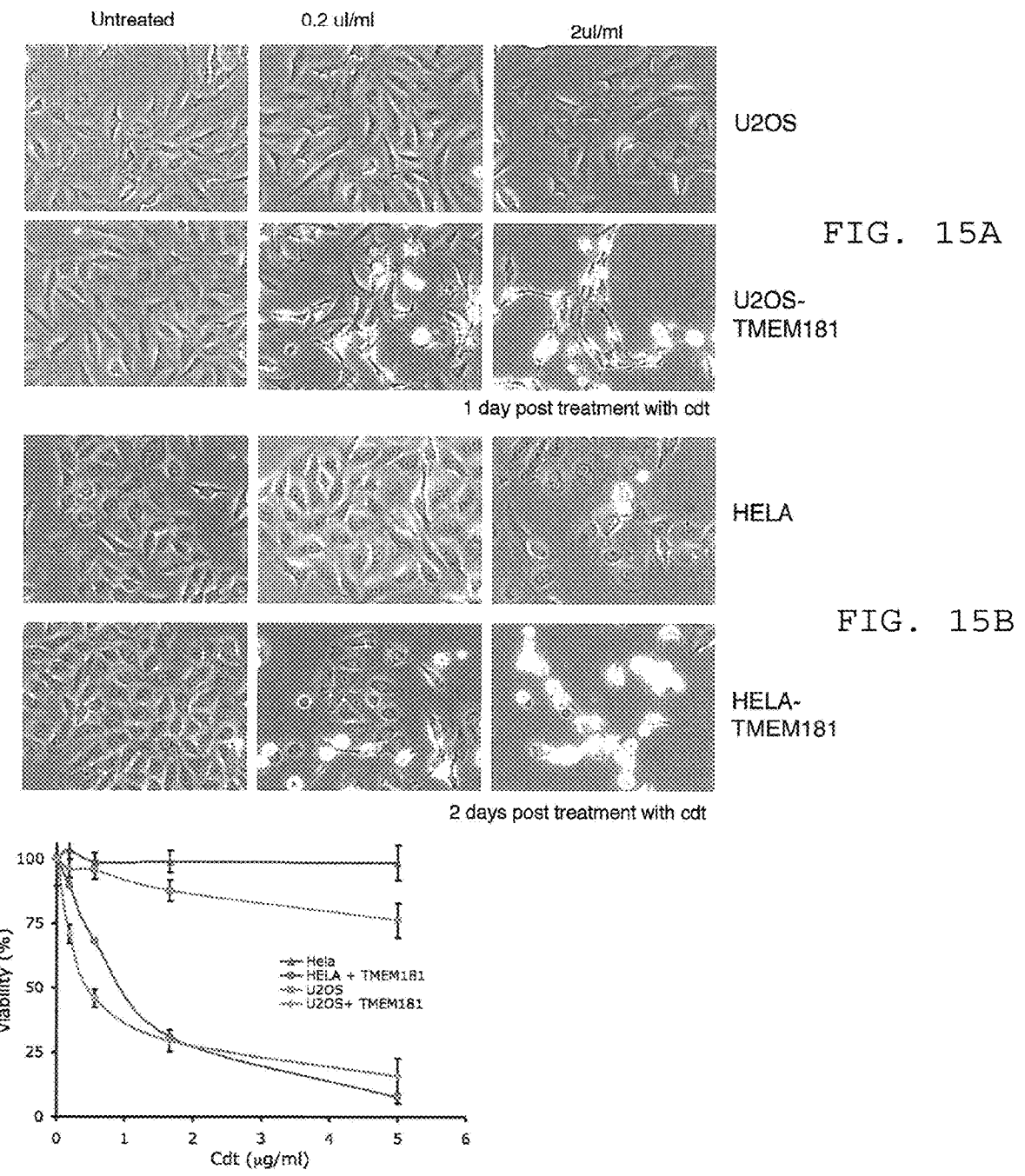
FIG. 15A depicts microscopic images of control cells or cells infected with a retrovirus directing the expression of TMEM181 treated with increasing concentrations of CDT. Experiments in U2OS cells were photographed one day after toxin treatment (upper panel) and experiments in HELA cells two days after toxin treatment.
FIG. 15B shows quantification of cell viability of the same cells after 4 days of toxin treatment.
Figure 16A:
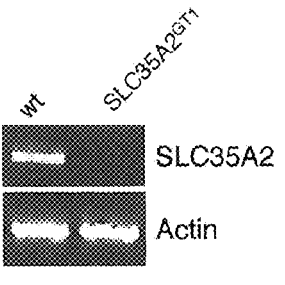
FIG. 16A shows RT-PCR analysis of SLC35A2 mRNA levels in gene trap cells.
Figure 16B:
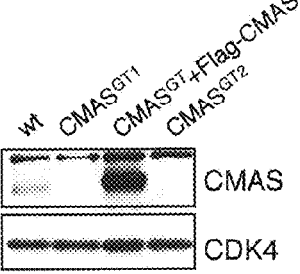
FIG. 16B shows immunoblot analysis of CMAS protein levels in wild type cells, CMAS deficient cells and in the same cells infected with a retrovirus expressing Flag-CMAS.
Figure 16C:
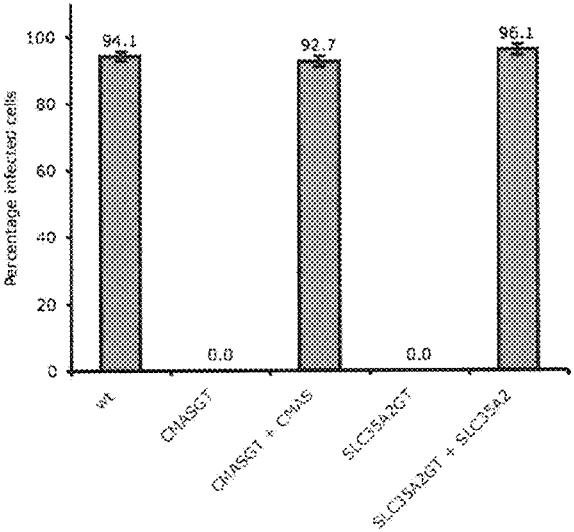
FIG. 16C is a graph showing quantification of influenza virus infection in wild type cells and in cells with mutations in CMAS or SLC35A2. Mutant cells complemented with the respective cDNAs were included. Cells were infected with influenza virus, stained 12 hours later for Influenza A Nucleoprotein and infected cells were scored.

TMEM181 mutants remained fully sensitive to lysenin, suggesting that TMEM181 resistance is accomplished by mechanisms other than sphingomyelin depletion. Because a receptor for CDT must localize to the plasma membrane, we tested whether CDT binds to TMEM181. FLAG-tagged CDT was adsorbed onto anti-Flag beads and incubated with cell lysates prepared from wild type KBM7 cells and from KBM-7 cells that express HA-tagged TMEM181. Immunoblot analysis showed robust binding of TMEM181 to CDT (FIG. 9D). When TMEM181 was over-expressed by retroviral transduction in Swiss 3T3, U2OS and Hela cells, it sensitized these unrelated cell types to CDT intoxication (FIG. 9E and FIG. 15), suggesting that TMEM181 expression levels are rate limiting for intoxication. We propose that CDT binds to the cell surface receptor TMEM181, an event both required and rate limiting for intoxication, and then enters the cell through sphingomyelin-dependent lipid-raft mediated endocytosis, followed by nuclear entry and cleavage of cellular DNA (FIG. 9F). For many GPCRs, their engagement not only leads to signal transduction but also triggers their rapid endocytosis. Whether G-protein signaling plays a role in cell intoxication by CDT remains to be determined.

Isolation of Host Factors Essential for Influenza Virus Infectivity

Figures 18A, 18B, 18C:
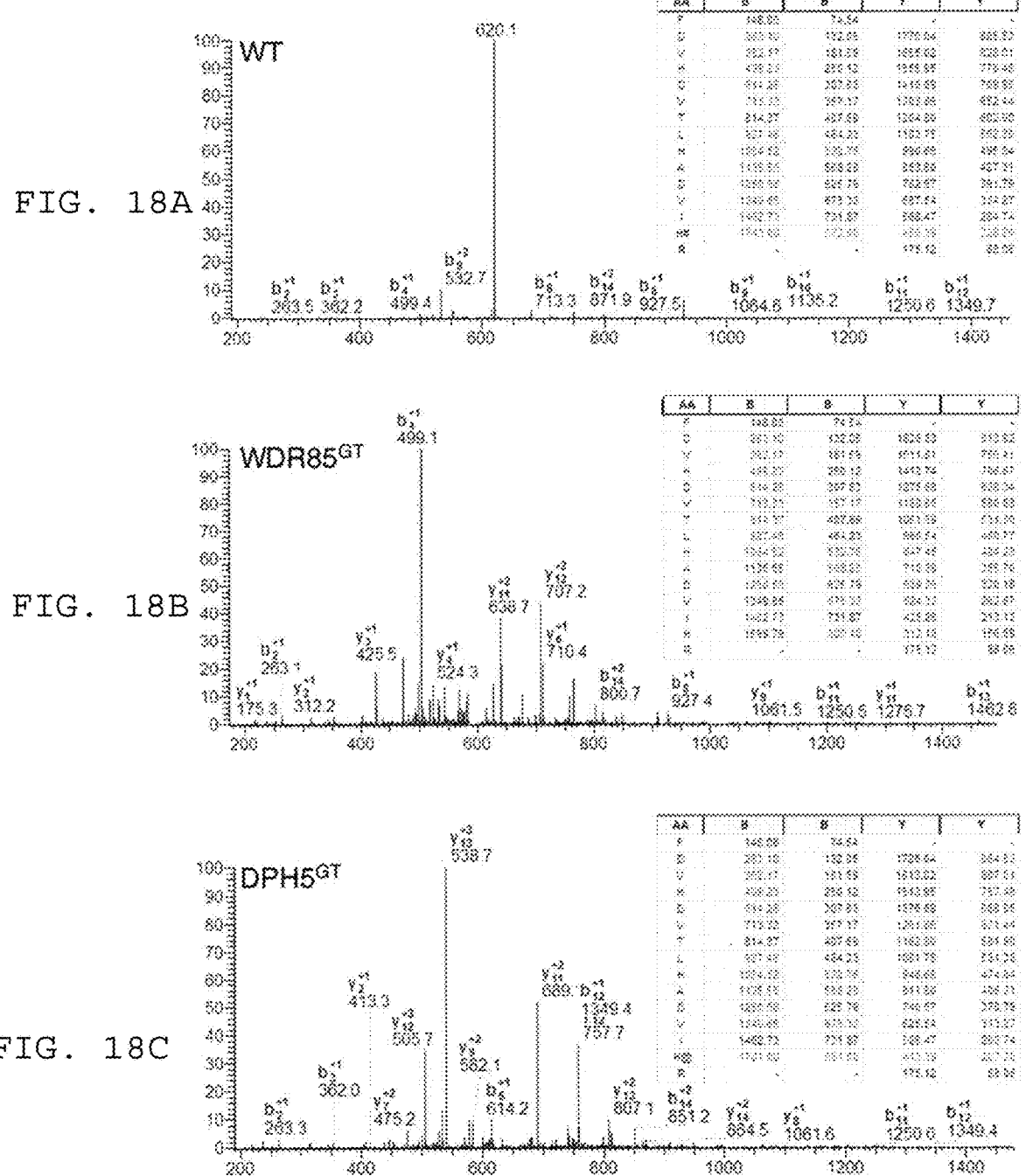
FIG. 18A shows the results of MS/MS spectra of tryptic fragment FDVHDVTLHADVIHR (SEQ ID NO: 186) derived from SBP-tagged EF2 purified from wild type cells. Fragmentation yielded peptides with a neutral loss of 58 Da, which is characteristic for the presence of diphthamide due to its unstable nature as a quaternary ammonium salt (Ortiz et al., *Journal of Biological Chemistry* 281: 32639 (Oct. 27, 2006)). Note that the SBP-tagged EF2 construct used for mass spectrometry contains a mutation (A713V) fortuitously introduced during PCR that has no effect on diphthamide biosynthesis.
FIG. 18B shows the results of MS/MS spectrum for the same peptide derived from WDR85 deficient cells consistent with the absence of any modification on His715.
FIG. 18C shows the results of MS/MS spectrum of the identical peptide derived from DPH5 deficient cells containing the +101 'intermediate' modification.

We next isolated mutant cells that were resistant to influenza virus A (PR/8/34; H1N1), as KBM7 cells are readily killed upon exposure to the virus. Proviral/host junction sequencing revealed two independent insertions in CMAS, the gene that encodes the enzyme responsible for activation of NeuAc to CMP-NeuAc, the glycosyl donor used in sialic acid-containing glycoconjugate synthesis. These structures can be recognized by flu hemagglutinin and are the receptors on flu-susceptible cells. We recovered three independent insertions in SLC35A2 (FIG. 10A), a gene whose product transports UDP-galactose from the cytoplasm to the Golgi, where it serves as a glycosyl donor (14) important for the generation of glycans to be modified with sialic acids. To determine whether mutant cells could be infected by flu, we exposed cells to virus and stained for influenza nucleoprotein 12 hours after infection. As expected, KBM7 cells showed high levels of infection (~95% infection), whereas CMAS and SLC35A2 mutant cells showed near-complete resistance to virus infection (<0.01% infection); see FIG. 10B and FIG. 18C. Absence of CMAS and SLC35A2 expression in the mutants was verified by RT-PCR or immunoblot analysis (FIGS. 18A & 18B). Transduction with cDNAs encoding the disrupted genes fully restored susceptibility to flu infection (FIG. 11B), indicating that the observed resistance is attributable to the mutated loci. Although the KBM7 genome has not been screened at saturation for resistance to flu, the transporter (SLC35A2) and enzyme (CMAS) identified here could serve as targets for flu therapeutics because they are not essential for either cell proliferation or viability. Neither gene has previously been identified as essential in determining susceptibility to flu.

Identification of Host Factors for ADP-Ribosylating Toxins

Figures 11A, 11B, 11C:
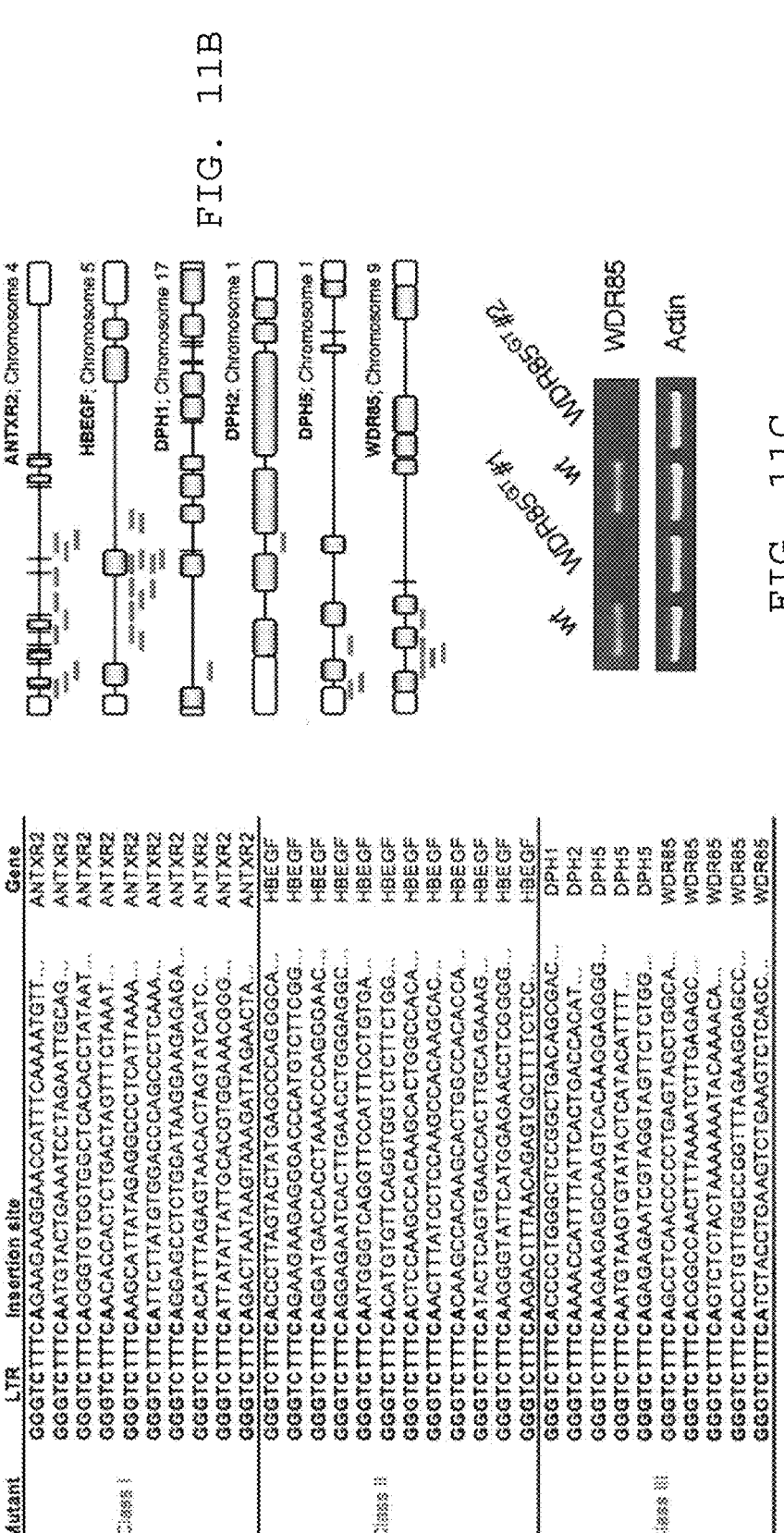
FIG. 11A shows gene trap insertion sites (SEQ ID NOS: 89-120, respectively) in clones that are resistant to diphtheria toxin (Class I), anthrax-DTA toxin (Class II) or both (Class III).
FIG. 11B is a schematic outline of the insertion sites indicates that all insertions cluster towards the 5' end of the gene.
FIG. 11C illustrates that RT-PCR for WDR85 shows undetectable WDR85 mRNA levels in independent clones with gene trap insertions in the WDR85 locus.
Figure 11D:
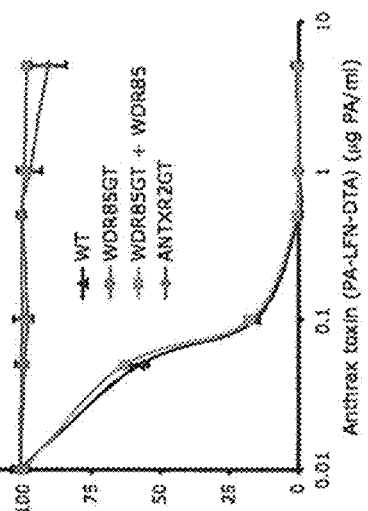
FIG. 11D illustrates the resistance of WDR85GT cells to diphtheria toxin (left), Exotoxin A (middle) or anthrax-DTA (right). Identified clones with mutations in HB-EGF, DPH5 and ANTRX2 served as insensitive controls for these respective toxins and WDR85GT cells reconstituted with a WDR85 cDNA re-acquired sensitivity to all three toxins.
Figure 11D:
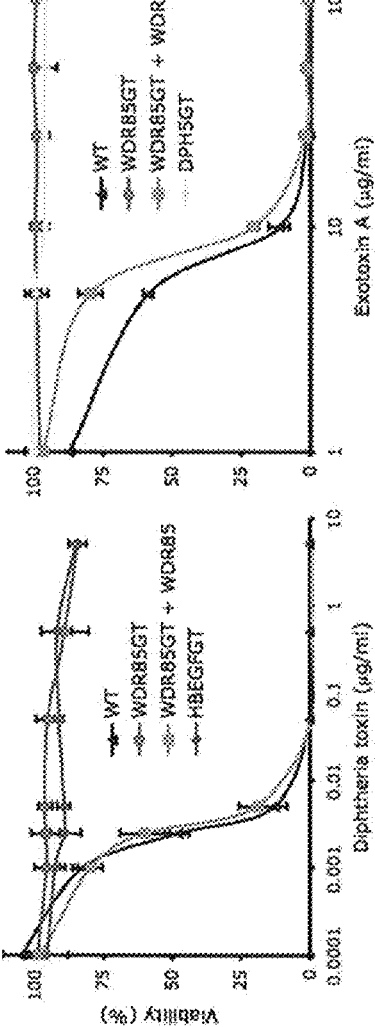

Diphtheria and anthrax toxins are AB toxins composed of a cell-binding moiety (B) and an active (A) subunit that targets a host function to increase virulence. We have a detailed molecular understanding of how diphtheria toxin enters the cell and induces cell death (15, 16). We screened mutagenized cells with diphtheria or anthrax toxin. Because native anthrax toxin is not cytotoxic for KBM7-cells, we exposed cells to the cell-binding component of anthrax toxin-protective antigen (PA)- and anthrax lethal factor (LFN) fused to the catalytic domain of diphtheria toxin (LFN-DTA) (17). Resistant mutants were classified as either being resistant to anthrax toxin (Class I), resistant to diphtheria toxin (Class II) or resistant to both (Class III). Mutants in the known anthrax toxin receptor (ANTXR2) (18) were recovered with ten independent insertions, and for the known diphtheria toxin receptor (HB-EGF) (19) with twelve insertions (FIG. 11A). The third class of mutants included genes involved in diphthamide biosynthesis (DPH1, DPH2 and DPH5, see (16)) and a previously uncharacterized gene named WDR85 (FIGS. 11A & 11B). All of these insertions were in the same transcriptional orientation as the mutated gene and therefore predicted to impair gene function. In the WDR85 mutant (hereafter referred to as WDR85GT), no WDR85 transcripts were observed as determined by RT-PCR (FIG. 11C). The resistance of WDR85GT was readily complemented by transfection with WDR85 cDNA, which restored sensitivity of WDR85GT cells to diphtheria toxin, anthrax toxin (PA-LFN-DTA) and a third toxin, *Pseudomonas* exotoxin A (FIG. 10D). Although native anthrax toxin is not lethal to most cell types, including KBM-7, its cellular entry and activity can be probed by monitoring cleavage of its cellular target MEK-3. WDR85GT cells were still responsive to the native anthrax toxin because the extent of proteolytic cleavage of MEK-3 was comparable for WDR85GT and wild-type cells (FIG. 17A), suggesting that toxin entry was normal in WDR85GT cells.

WDR85 is Part of the Dipthamide Biosynthetic Pathway

Figures 12A, 12B, 12C, 12D, 12E, 12F, 12G:
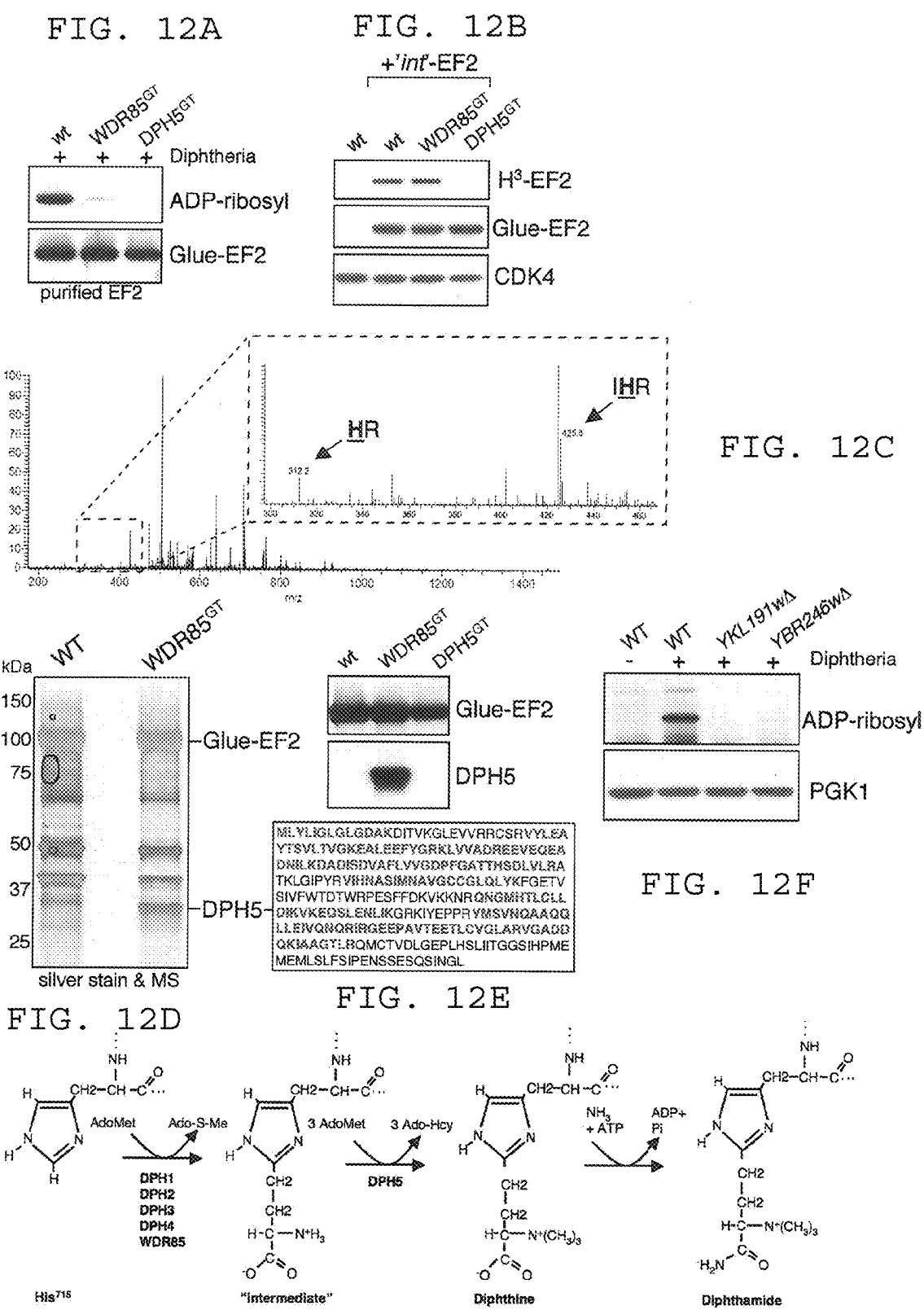
FIG. 12A shows in vitro ADP-ribosylation of SBP-tagged EF2 purified from wild type, WDR85 and DPH5 mutant cells by DTA-LFN in the presence of NAD-Biotin. Streptavidin-HRP was used to detect ADP-ribosylation and total EF-2 was detected by immunoblot analysis.
FIG. 12B shows methylation of 'intermediate' EF2 by wild type, WDR85 and DPH5 mutant cell lysates. SBP-tagged 'intermediate' EF2 was purified from DPH5 mutant cells and incubated in lysates derived from the indicated genotypes in the presence of [methyl-3H] Adenosylmethionine (Ado-S-Me) as methyl donor. The amount of supplied 'intermediate' EF2 was detected by immunoblot analysis, with CDK4 as loading control.
FIG. 12C shows MS/MS spectra of a tryptic peptide derived from SBP-tagged EF2 purified from WDR85 mutant cells. Peptide fragments characteristic for unmodified His715 are indicated.
FIG. 12D shows silverstain of SPB-EF2 purified from wild type and WDR85 deficient cells and peptide sequences derived from the protein that co-purifies with EF2 in WDR85 deficient cells.
As shown in FIG. 12E, IP-immunoblot analysis indicates that DPH5 (SEQ ID NO: 121) co-purifies with EF2 derived from WDR85 deficient cells.
As illustrated in FIG. 12F, protein extracts from WT, YKL191W and YBR246W deficient *Saccharomyces cerevisiae* strains were incubated with LFN-DTA in the presence of NAD-Biotin. Streptavidin-HRP was used to detect ADP-ribosylation and PGK1 was used as loading control.
FIG. 12G shows a suggested pathway for the stepwise biosynthesis of diphthamide. Ado-S-Me, methylthioadenosine; Ado-Hcy, S-adenosylhomocysteine.
Figures 17A, 17B, 17C:
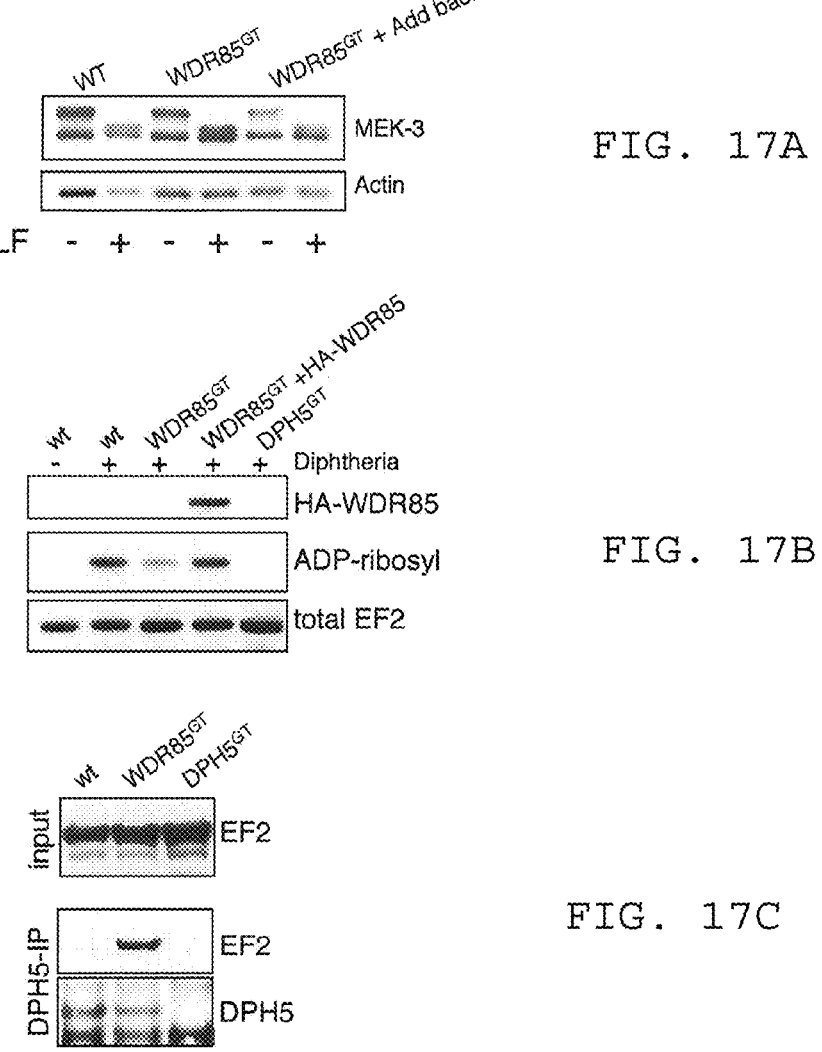
FIG. 17A shows immunoblot analysis demonstrating that anthrax lethal factor toxin causes MEK-3 cleavage in wild type, WDR85 mutant and WDR85 mutant cells complemented with WDR85. Actin was used as a loading control.
As shown in FIG. 17B, cell lysates of wild type and WDR85 deficient cells were exposed to LFN-DTA in the presence of NAD-Biotin. WDR85 mutant cells reconstituted with a WDR85 cDNA and DPH5 mutant cells served as controls. ADP-ribosylation was detected using Streptavidin-HRP and total amounts of EF2 were used as loading control.
FIG. 17C shows immunoblot analysis when wild type, WDR85 deficient and DPH5 deficient cell lysates were immunoprecipitated using DPH5 antibodies Immunoprecipitates were blotted for DPH5 and EF2 and whole cell extracts for EF2.
Figure 19A:
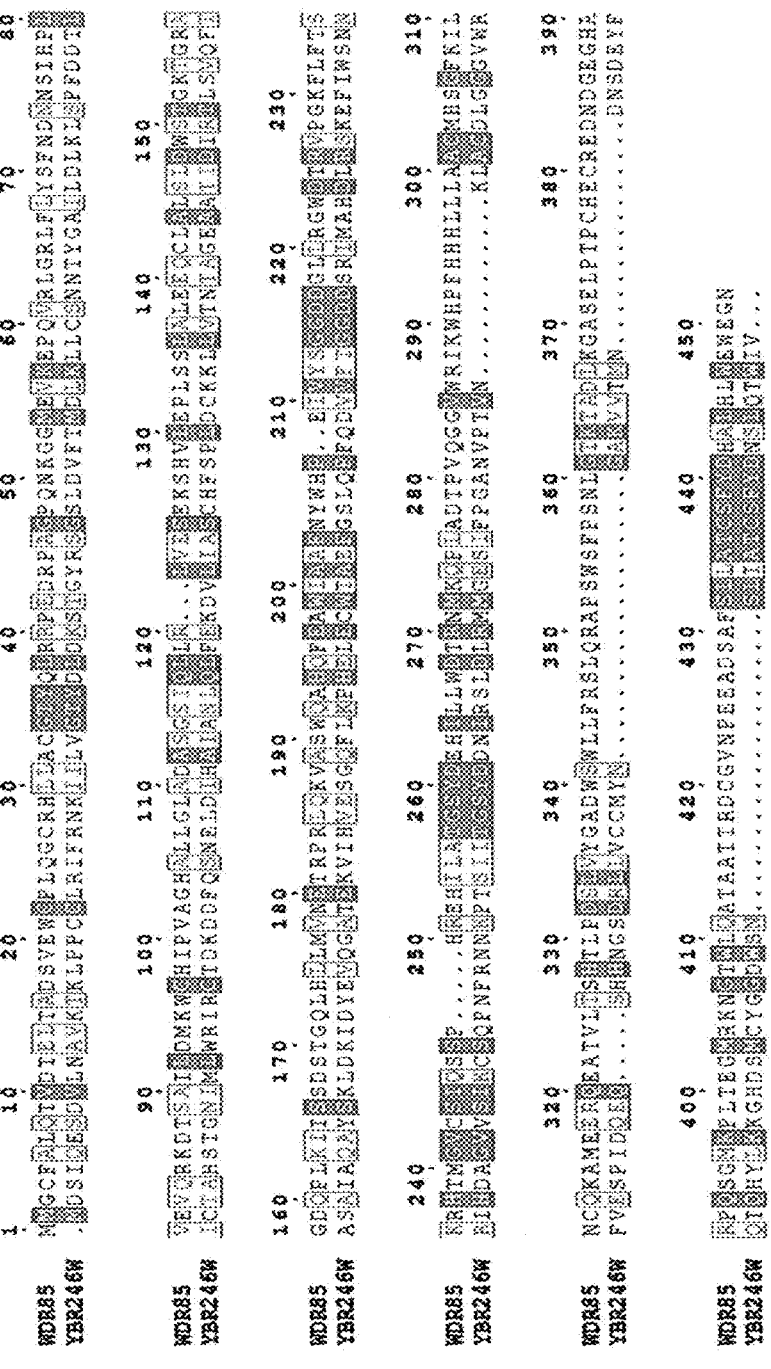
FIG. 19A depicts an alignment of the amino acid sequences of human WDR85 (SEQ ID NO: 122) and *Sac-*

Given the strong resistance of WDR85 mutant cells to different bacterial toxins, we further explored the mechanism by which WDR85 confers sensitivity to toxin-mediated cell death. Diphtheria toxin, LFN-DTA and exotoxin A potently inhibit host translation through ADP ribosylation of elongation factor 2 (EF2), leading to cell death. ADP-ribosylation occurs on diphthamide, a posttranslationally modified histidine uniquely present in EF2 and conserved among all eukaryotes. As WDR85 was not required for toxin entry, we investigated EF2 ribosylation in response to diphtheria toxin. In cell lysates derived from WDR85GT cells, EF2 ribosylation was impaired and could be restored by re-expression of a WDR85 cDNA (FIG. 17B). EF-2 fused to a streptavidin-binding peptide (SBP) purified from WDR85GT cells also was a poor substrate for ADP-ribosylation. Impaired ADP-ribosylation is therefore an inherent property of EF-2 derived from WDR85GT cells and is not due to the presence or absence of other factors present in cell lysates (FIG. 12A). Diphthamide biosynthesis is the result of stepwise posttranslational modification of His175 (FIG. 12G), the proteins responsible for which are known (16, 20, 21). The second step comprises the trimethylation of "intermediate" EF2 by the methyltransferase DPH5, with S-adenosylmethionine as the methyl donor (22). To investigate if this methylation step was affected by loss of WDR85, we purified intermediate EF2 from DPH5 null cells and performed in vitro methylation assays on cell lysates. Efficient methylation of 'intermediate' EF2 by wild type and WDR85GT cell lysates suggested that WDR85 is not required for the second step of diphthamide biosynthesis (FIG. 12B). Next, we purified EF2 from WDR85GT cells and used LC/MS/MS to monitor the relevant modifications of His175. Modifications of His175 predict an increase in mass by +143 (diphthamide), +142 (diphthine), and +101 (the intermediate) mass units for those peptides that carry the modified His residue. SBP-tagged EF2 isolated from WDR85GT showed a mass consistent with the presence of unmodified His175, whereas modifications of EF2 purified from wild type and DPH5 mutant cells showed a mass that was expected for the presence of diphthamide and "intermediate", respectively (FIG. 12C and FIG. 19). The absence of modified histidine in EF2 suggests that WDR85 plays a role in the first step in diphthamide biosynthesis.

In the course of purification of EF2 from WDR85GT cells, we detected a protein that strongly interacted with EF2 (FIG. 12D and FIG. 17C). Mass spectrometry identified this protein as DPH5, confirmed by immunoblot analysis (FIG. 12E) and by co-immunoprecipitation of the endogenous proteins (FIG. 17C). WDR85 lacks homology to previously identified proteins involved in diphthamide biosynthesis but does contain WD40 repeats, often involved in protein-protein interactions. We suggest that WDR85 may serve as a scaffold to coordinate the association (or dissociation) of enzymatic complexes required for the stepwise biosynthesis of diphthamide.

WDR85 is a conserved protein with homology to yeast YBR246W (FIG. 19). We used a database containing fitness profiles of deletion strains of all nonessential yeast genes under 1144 chemical conditions to cluster genes with similar profiles to YBR246W (23). The top 10 genes that phenocluster with YBR246W by homozygous co-sensitivity included DPH2 and DPH5. The only gene annotation terms we found enriched concerned diphthamide biosynthesis (p-value 9e-04, FIG. 19). To test directly if YBR246W is involved in diphthamide biosynthesis we undertook ribosylation assays in protein extracts derived from WT yeast or yeast strains deleted for YKL191W (DPH2) or YBR246W. Gratifyingly, deficiency of YKL191W and YBR246W both impair ADP-ribosyl acceptor activity of EF2 in yeast (FIG. 12F). These data suggest that the role of WDR85 in diphthamide biosynthesis is conserved in eukaryotes and that the proposed scaffolding role may be the main function of WDR85 in cells. In conclusion, our approach has identified WDR85 as a previously unrecognized host gene involved in the first step in diphthamide biosynthesis, despite previous suggestions that all proteins involved in this complex posttranslational modification were known (16).

REFERENCES

1. H. J. Muller, *Science* 66, 84 (1927).
2. A. L. Brass et al., *Science* 319, 921 (Feb. 15, 2008).
3. J. A. Philips, E. J. Rubin, N. Perrimon, *Science* 309, 1251 (Aug. 19, 2005).
4. L. H. Hao et al., *Nature* 454, 890 (Aug. 14, 2008).
5. R. Salomon, R. G. Webster, *Cell* 136, 402 (Feb. 6, 2009).
6. A. Moscona, *New England Journal of Medicine* 360, 953 (Mar. 5, 2009).
7. M. Kotecki, P. S. Reddy, B. H. Cochran, *Experimental Cell Research* 252, 273 (Nov. 1, 1999).
8. S. Nagata, *Cell* 88, 355 (1997).
9. B. Luo et al., *Proceedings of the National Academy of Sciences of the United States of America* 105, 20380 (Dec. 23, 2008).
10. F. Cong et al., *Molecular Cell* 6, 1413 (December, 2000).
11. M. Lara-Tejero, J. E. Galan, *Science* 290, 354 (Oct. 13, 2000).
12. D. Nesic, Y. Hsu, C. E. Stebbins, *Nature* 429, 429 (May 27, 2004).
13. M. Miyaji et al., *Journal of Experimental Medicine* 202, 249 (Jul. 18, 2005).
14. H. Sprong et al., *Molecular Biology of the Cell* 14, 3482 (August, 2003).
15. R. J. Collier, *Toxicon: official journal of the International Society on Toxinology* 39, 1793 (2001).
16. S. H. Liu, G. T. Milne, J. G. Kuremsky, G. R. Fink, S. H. Leppla, *Molecular and Cellular Biology* 24, 9487 (November, 2004).
17. J. C. Milne, S. R. Blanke, P. C. Hanna, R. J. Collier, *Molecular Microbiology* 15, 661 (February, 1995).
18. H. M. Scobie, G. J. A. Rainey, K. A. Bradley, J. A. T. Young, *Proceedings of the National Academy of Sciences of the United States of America* 100, 5170 (2003).
19. J. G. Naglich, J. E. Metherall, D. W. Russell, L. Eidels, *Cell* 69, 1051 (1992).
20. L. C. Mattheakis, W. H. Shen, R. J. Collier, *Molecular and Cellular Biology* 12, 4026 (SEP, 1992).
21. S. H. Liu, S. H. Leppla, *Molecular Cell* 12, 603 (SEP, 2003).
22. J. Y. Chen, J. W. Bodley, *The Journal of biological chemistry* 263, 11692 (1988).
23. M. E. Hillenmeyer et al., *Science* 320, 362 (Apr. 18, 2008).
24. S. L. Forsburg, *Nature Reviews Genetics* 2, 659 (SEP, 2001).

25. Y. Ma, A. Creanga, L. Lum, P. A. Beachy, *Nature* 443, 359 (SEP 21, 2006).

26. C. J. Echeverri et al., *Nature Methods* 3, 777 (October, 2006).

27. S. P. Goff, *Cell* 135, 417 (2008).

28. F. D. Bushman et al., *PLoS pathogens* 5, e1000437 (2009).

29. P. A. Ortiz, R. Ulloque, G. K. Kihara, H. Y. Zheng, T. G. Kinzy, *Journal of Biological Chemistry* 281, 32639 (Oct. 27, 2006).

We claim:

1. An adherent, near-haploid mammalian cell derived from a non-adherent near-haploid KBM7 cell, wherein the non-adherent near-haploid KBM7 cell comprises viral vectors encoding Oct4, Sox2, Klf4 and c-Myc.

2. The adherent, near-haploid mammalian cell of claim 1, wherein the viral vectors are retroviral vectors.

3. The adherent, near-haploid mammalian cell of claim 1, wherein said adherent, near-haploid mammalian cell comprises exogenous DNA encoding Oct4, Sox2, Klf4, and c-Myc integrated into its genome.

4. A method of deriving an adherent, near-haploid KBM7 cell comprising (a) introducing viral vectors encoding Oct4, Sox2, Klf4, and c-Myc into a non-adherent, near-haploid KBM7 cell in culture; and (b) maintaining said culture for a time sufficient for formation of an adherent near-haploid KBM7 derived cell , wherein the adherent, near-haploid KBM7 cell comprises exogenous DNA encoding Oct4, Sox2, Klf4 and c-Myc.

5. The method of claim 4, wherein the viral vectors are retroviral vectors.

6. An adherent, near-haploid KBM7 cell derived according to the method of claim 4.

* * * * *

```
                            SEQUENCE LISTING

Sequence total quantity: 186
SEQ ID NO: 1               moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 1
gggtctttca gaagaaggaa ccatttcaaa atgtt                               35

SEQ ID NO: 2               moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 2
gggtctttca atgtactgaa atcctagaat tgcag                               35

SEQ ID NO: 3               moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 3
gggtctttca gggtgtggtg gctcacacct ataat                               35

SEQ ID NO: 4               moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 4
gggtctttca acaccactct gactagtttc taaat                               35

SEQ ID NO: 5               moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 5
gggtctttca agcattatag aggccctcat taaaa                               35

SEQ ID NO: 6               moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 6
gggtctttca ttcttatgtg gacccagccc tcaaa                               35

SEQ ID NO: 7               moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 7
gggtctttca ggagcctctg gataaggaag agaga                               35
```

-continued

```
SEQ ID NO: 8         moltype = DNA   length = 35
FEATURE              Location/Qualifiers
misc_feature         1..35
                     note = Gene-trap integration site
source               1..35
                     mol_type = other DNA
                     organism = synthetic construct
SEQUENCE: 8
gggtctttca catttagagt aacactagta tcatc                                35

SEQ ID NO: 9         moltype = DNA   length = 35
FEATURE              Location/Qualifiers
misc_feature         1..35
                     note = Gene-trap integration site
source               1..35
                     mol_type = other DNA
                     organism = synthetic construct
SEQUENCE: 9
gggtctttca ttatattatt gcacgtggaa acggg                                35

SEQ ID NO: 10        moltype = DNA   length = 35
FEATURE              Location/Qualifiers
misc_feature         1..35
                     note = Gene-trap integration site
source               1..35
                     mol_type = other DNA
                     organism = synthetic construct
SEQUENCE: 10
gggtctttca gactaataag taaagattag aacta                                35

SEQ ID NO: 11        moltype = DNA   length = 35
FEATURE              Location/Qualifiers
misc_feature         1..35
                     note = Gene-trap integration site
source               1..35
                     mol_type = other DNA
                     organism = synthetic construct
SEQUENCE: 11
gggtctttca cccctgggct ccggctgaca gcgac                                35

SEQ ID NO: 12        moltype = DNA   length = 35
FEATURE              Location/Qualifiers
misc_feature         1..35
                     note = Gene-trap integration site
source               1..35
                     mol_type = other DNA
                     organism = synthetic construct
SEQUENCE: 12
gggtctttca aaaccatttt attcactgac cacat                                35

SEQ ID NO: 13        moltype = DNA   length = 35
FEATURE              Location/Qualifiers
misc_feature         1..35
                     note = Gene-trap integration site
source               1..35
                     mol_type = other DNA
                     organism = synthetic construct
SEQUENCE: 13
gggtctttca agaagaggca agtcacaagg agggg                                35

SEQ ID NO: 14        moltype = DNA   length = 35
FEATURE              Location/Qualifiers
misc_feature         1..35
                     note = Gene-trap integration site
source               1..35
                     mol_type = other DNA
                     organism = synthetic construct
SEQUENCE: 14
gggtctttca atgtaagtgt atactcatac atttt                                35

SEQ ID NO: 15        moltype = DNA   length = 35
FEATURE              Location/Qualifiers
misc_feature         1..35
                     note = Gene-trap integration site
source               1..35
                     mol_type = other DNA
                     organism = synthetic construct
SEQUENCE: 15
gggtctttca gagagaatcg taggtagttc tctgg                                35
```

-continued

```
SEQ ID NO: 16            moltype = DNA  length = 35
FEATURE                  Location/Qualifiers
misc_feature             1..35
                         note = Gene-trap integration site
source                   1..35
                         mol_type = other DNA
                         organism = synthetic construct
SEQUENCE: 16
gggtctttca gcctcaaccc cctgagtagc tggca                             35

SEQ ID NO: 17            moltype = DNA  length = 35
FEATURE                  Location/Qualifiers
misc_feature             1..35
                         note = Gene-trap integration site
source                   1..35
                         mol_type = other DNA
                         organism = synthetic construct
SEQUENCE: 17
gggtctttca cggccaactt taaaatcttg agagc                             35

SEQ ID NO: 18            moltype = DNA  length = 35
FEATURE                  Location/Qualifiers
misc_feature             1..35
                         note = Gene-trap integration site
source                   1..35
                         mol_type = other DNA
                         organism = synthetic construct
SEQUENCE: 18
gggtctttca gtctctacta aaaaaataca aaaca                             35

SEQ ID NO: 19            moltype = DNA  length = 35
FEATURE                  Location/Qualifiers
misc_feature             1..35
                         note = Gene-trap integration site
source                   1..35
                         mol_type = other DNA
                         organism = synthetic construct
SEQUENCE: 19
gggtctttca cctgttggcc ggtttagaag gagcc                             35

SEQ ID NO: 20            moltype = DNA  length = 35
FEATURE                  Location/Qualifiers
misc_feature             1..35
                         note = Gene-trap integration site
source                   1..35
                         mol_type = other DNA
                         organism = synthetic construct
SEQUENCE: 20
gggtctttca cccttagtac tatgagccca gggca                             35

SEQ ID NO: 21            moltype = DNA  length = 35
FEATURE                  Location/Qualifiers
misc_feature             1..35
                         note = Gene-trap integration site
source                   1..35
                         mol_type = other DNA
                         organism = synthetic construct
SEQUENCE: 21
gggtctttca gaagaagagg gacccatgtc ttcgg                             35

SEQ ID NO: 22            moltype = DNA  length = 35
FEATURE                  Location/Qualifiers
misc_feature             1..35
                         note = Gene-trap integration site
source                   1..35
                         mol_type = other DNA
                         organism = synthetic construct
SEQUENCE: 22
gggtctttca ggatgaccac ctaaacccag ggaac                             35

SEQ ID NO: 23            moltype = DNA  length = 35
FEATURE                  Location/Qualifiers
misc_feature             1..35
                         note = Gene-trap integration site
source                   1..35
                         mol_type = other DNA
                         organism = synthetic construct
SEQUENCE: 23
```

-continued

```
gggtctttca ggagaatcac ttgaacctgg gaggc                              35

SEQ ID NO: 24           moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 24
gggtctttca atgggtcagg ttccatttcc tgtga                              35

SEQ ID NO: 25           moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 25
gggtctttca catgtgttca ggtggtctct tctgg                              35

SEQ ID NO: 26           moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 26
gggtctttca ctccaagcca caagcactgg ccaca                              35

SEQ ID NO: 27           moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 27
gggtctttca actttatcct ccaagccaca agcac                              35

SEQ ID NO: 28           moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 28
gggtctttca caagccacaa gcactggcca cacca                              35

SEQ ID NO: 29           moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 29
gggtctttca tactcagtga accacttgca gaaag                              35

SEQ ID NO: 30           moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 30
gggtctttca agggtattca tggagaacct cgggg                              35

SEQ ID NO: 31           moltype = DNA   length = 35
FEATURE                 Location/Qualifiers
misc_feature            1..35
                        note = Gene-trap integration site
source                  1..35
                        mol_type = other DNA
                        organism = synthetic construct
```

-continued

```
SEQUENCE: 31
gggtctttca agactttaac agagtgcttt tctcc                               35

SEQ ID NO: 32              moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 32
gggtctttca gttgtcattg aaaatccaag gatat                               35

SEQ ID NO: 33              moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 33
gggtctttca ttctcaacat tccactcttc tctat                               35

SEQ ID NO: 34              moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 34
gggtctttca cctacagaga tagctcattt cttac                               35

SEQ ID NO: 35              moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 35
gggtctttca gtgcattggg aaattttgct accaa                               35

SEQ ID NO: 36              moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 36
gggtctttca ccaggcactg ggatagaaag gtgaa                               35

SEQ ID NO: 37              moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 37
gggtctttca caagtaaatg taatataaag atttt                               35

SEQ ID NO: 38              moltype = DNA   length = 35
FEATURE                    Location/Qualifiers
misc_feature               1..35
                           note = Gene-trap integration site
source                     1..35
                           mol_type = other DNA
                           organism = synthetic construct
SEQUENCE: 38
gggtctttca taagaaatga gctatctctg taggc                               35

SEQ ID NO: 39              moltype = DNA   length = 35
FEATURE                    Location/Qualifiers
misc_feature               1..35
                           note = Gene-trap integration site
source                     1..35
                           mol_type = other DNA
```

```
                       organism = synthetic construct
SEQUENCE: 39
gggtctttca gagaacatct cttctggagg aacaa                                35

SEQ ID NO: 40          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 40
gggtctttca aaagtattcc tatttccttg cagtc                                35

SEQ ID NO: 41          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 41
gggtctttca gttgtcattg aaaatccaag gatat                                35

SEQ ID NO: 42          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 42
gggtctttca gctgggagcc tggcttgata agcag                                35

SEQ ID NO: 43          moltype = DNA   length = 34
FEATURE                Location/Qualifiers
misc_feature           1..34
                       note = Gene-trap integration site
source                 1..34
                       mol_type = other DNA
                       organism = synthetic construct
SEQUENCE: 43
gggtctttca taaggaagca gaaggaaaaa cagt                                 34

SEQ ID NO: 44          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 44
gggtctttca atttaaataa ggctgttttt gtgtg                                35

SEQ ID NO: 45          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 45
gggtctttca ccccgcacct ggcagcccta attct                                35

SEQ ID NO: 46          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 46
gggtctttca ggctccagct ccttccttgt tccgt                                35

SEQ ID NO: 47          moltype = DNA   length = 35
FEATURE                Location/Qualifiers
misc_feature           1..35
                       note = Gene-trap integration site
source                 1..35
```

-continued

```
                        mol_type = other DNA
                        organism = synthetic construct
SEQUENCE: 47
gggtctttca agaatagtct actaaataca agaaa                                 35

SEQ ID NO: 48          moltype = DNA   length = 35
FEATURE                Location/Qualifiers
misc_feature           1..35
                        note = Gene-trap integration site
source                 1..35
                        mol_type = other DNA
                        organism = synthetic construct
SEQUENCE: 48
gggtctttca ggctaaggcc accgaaacca ttctg                                 35

SEQ ID NO: 49          moltype = DNA   length = 35
FEATURE                Location/Qualifiers
misc_feature           1..35
                        note = Gene-trap integration site
source                 1..35
                        mol_type = other DNA
                        organism = synthetic construct
SEQUENCE: 49
gggtctttca ttccggaaaa tcagcagatg gtgac                                 35

SEQ ID NO: 50          moltype = DNA   length = 35
FEATURE                Location/Qualifiers
misc_feature           1..35
                        note = Gene-trap integration site
source                 1..35
                        mol_type = other DNA
                        organism = synthetic construct
SEQUENCE: 50
gggtctttca gaccctcctc tgggcccctc ggaaa                                 35

SEQ ID NO: 51          moltype = DNA   length = 35
FEATURE                Location/Qualifiers
misc_feature           1..35
                        note = Gene-trap integration site
source                 1..35
                        mol_type = other DNA
                        organism = synthetic construct
SEQUENCE: 51
gggtctttca cattgaagcc ccactacagc tctgg                                 35

SEQ ID NO: 52          moltype = DNA   length = 35
FEATURE                Location/Qualifiers
misc_feature           1..35
                        note = Gene-trap integration site
source                 1..35
                        mol_type = other DNA
                        organism = synthetic construct
SEQUENCE: 52
gggtctttca ctgcccttaa aaagttttag tggga                                 35

SEQ ID NO: 53          moltype = DNA   length = 35
FEATURE                Location/Qualifiers
misc_feature           1..35
                        note = Gene-trap integration site
source                 1..35
                        mol_type = other DNA
                        organism = synthetic construct
SEQUENCE: 53
gggtctttca gtgggagaaa caacaggtaa ccagg                                 35

SEQ ID NO: 54          moltype = DNA   length = 35
FEATURE                Location/Qualifiers
misc_feature           1..35
                        note = Gene-trap integration site
source                 1..35
                        mol_type = other DNA
                        organism = synthetic construct
SEQUENCE: 54
gggtctttca atttcaggct catcagaata tatct                                 35

SEQ ID NO: 55          moltype = DNA   length = 35
FEATURE                Location/Qualifiers
misc_feature           1..35
                        note = Gene-trap integration site
```

-continued

```
source                   1..35
                         mol_type = other DNA
                         organism = synthetic construct
SEQUENCE: 55
gggtctttca ctctttacct taagtcatta caatg                            35

SEQ ID NO: 56            moltype = DNA   length = 35
FEATURE                  Location/Qualifiers
misc_feature             1..35
                         note = Gene-trap integration site
source                   1..35
                         mol_type = other DNA
                         organism = synthetic construct
SEQUENCE: 56
gggtctttca acactaactt catggtttcc ccatc                            35

SEQ ID NO: 57            moltype = DNA   length = 35
FEATURE                  Location/Qualifiers
misc_feature             1..35
                         note = Gene-trap integration site
source                   1..35
                         mol_type = other DNA
                         organism = synthetic construct
SEQUENCE: 57
gggtctttca ttgttggcaa gtgtgtatgt tggtg                            35

SEQ ID NO: 58            moltype = DNA   length = 35
FEATURE                  Location/Qualifiers
misc_feature             1..35
                         note = Gene-trap integration site
source                   1..35
                         mol_type = other DNA
                         organism = synthetic construct
SEQUENCE: 58
gggtctttca acttgccaac ataaacgcac acaca                            35

SEQ ID NO: 59            moltype = DNA   length = 35
FEATURE                  Location/Qualifiers
misc_feature             1..35
                         note = Gene-trap integration site
source                   1..35
                         mol_type = other DNA
                         organism = synthetic construct
SEQUENCE: 59
gggtctttca taacaaagcc acaaaaacag aagtt                            35

SEQ ID NO: 60            moltype = DNA   length = 35
FEATURE                  Location/Qualifiers
misc_feature             1..35
                         note = Gene-trap integration site
source                   1..35
                         mol_type = other DNA
                         organism = synthetic construct
SEQUENCE: 60
gggtctttca gtcacgttgt tgaaaaggta atgaa                            35

SEQ ID NO: 61            moltype = DNA   length = 35
FEATURE                  Location/Qualifiers
misc_feature             1..35
                         note = Gene-trap integration site
source                   1..35
                         mol_type = other DNA
                         organism = synthetic construct
SEQUENCE: 61
gggtctttca gctgcactcg gtgtcgtcca gcctg                            35

SEQ ID NO: 62            moltype = DNA   length = 35
FEATURE                  Location/Qualifiers
misc_feature             1..35
                         note = Gene-trap integration site
source                   1..35
                         mol_type = other DNA
                         organism = synthetic construct
SEQUENCE: 62
gggtctttca ggagaagagg tctaggccgc tctgc                            35

SEQ ID NO: 63            moltype = DNA   length = 35
FEATURE                  Location/Qualifiers
misc_feature             1..35
```

```
                        note = Gene-trap integration site
source                  1..35
                        mol_type = other DNA
                        organism = synthetic construct
SEQUENCE: 63
gggtctttca aaggtaaatg aatttgaaag gatgg                                    35

SEQ ID NO: 64           moltype = DNA  length = 35
FEATURE                 Location/Qualifiers
misc_feature            1..35
                        note = Gene-trap integration site
source                  1..35
                        mol_type = other DNA
                        organism = synthetic construct
SEQUENCE: 64
gggtctttca gataggcaaa aaatggaatt tggtt                                    35

SEQ ID NO: 65           moltype = DNA  length = 35
FEATURE                 Location/Qualifiers
misc_feature            1..35
                        note = Gene-trap integration site
source                  1..35
                        mol_type = other DNA
                        organism = synthetic construct
SEQUENCE: 65
gggtctttca actggaaatg ttttgttatt tttca                                    35

SEQ ID NO: 66           moltype = DNA  length = 35
FEATURE                 Location/Qualifiers
misc_feature            1..35
                        note = Gene-trap integration site
source                  1..35
                        mol_type = other DNA
                        organism = synthetic construct
SEQUENCE: 66
gggtctttca aagaagccca atacaggtta aatgt                                    35

SEQ ID NO: 67           moltype = DNA  length = 35
FEATURE                 Location/Qualifiers
misc_feature            1..35
                        note = Gene-trap integration site
source                  1..35
                        mol_type = other DNA
                        organism = synthetic construct
SEQUENCE: 67
gggtctttca ctacagaaac aatgttggta cttca                                    35

SEQ ID NO: 68           moltype = DNA  length = 35
FEATURE                 Location/Qualifiers
misc_feature            1..35
                        note = Gene-trap integration site
source                  1..35
                        mol_type = other DNA
                        organism = synthetic construct
SEQUENCE: 68
gggtctttca ggacgacaca gcaagacccc atctc                                    35

SEQ ID NO: 69           moltype = DNA  length = 35
FEATURE                 Location/Qualifiers
misc_feature            1..35
                        note = Gene-trap integration site
source                  1..35
                        mol_type = other DNA
                        organism = synthetic construct
SEQUENCE: 69
gggtctttca gtttaccggg ccgggagccg taggc                                    35

SEQ ID NO: 70           moltype = DNA  length = 35
FEATURE                 Location/Qualifiers
misc_feature            1..35
                        note = Gene-trap integration site
source                  1..35
                        mol_type = other DNA
                        organism = synthetic construct
SEQUENCE: 70
gggtctttca taaggaagca gaaggaaaaa cagat                                    35

SEQ ID NO: 71           moltype = DNA  length = 35
FEATURE                 Location/Qualifiers
```

```
misc_feature              1..35
                          note = Gene-trap integration site
source                    1..35
                          mol_type = other DNA
                          organism = synthetic construct
SEQUENCE: 71
gggtctttca atttaaataa ggctgttttt gtgtg                                    35

SEQ ID NO: 72             moltype = DNA  length = 35
FEATURE                   Location/Qualifiers
misc_feature              1..35
                          note = Gene-trap integration site
source                    1..35
                          mol_type = other DNA
                          organism = synthetic construct
SEQUENCE: 72
gggtctttca aaacaaacaa aacatcccgt ttctg                                    35

SEQ ID NO: 73             moltype = DNA  length = 35
FEATURE                   Location/Qualifiers
misc_feature              1..35
                          note = Gene-trap integration site
source                    1..35
                          mol_type = other DNA
                          organism = synthetic construct
SEQUENCE: 73
gggtctttca gttgtcattg aaaatccaag gatat                                    35

SEQ ID NO: 74             moltype = DNA  length = 35
FEATURE                   Location/Qualifiers
misc_feature              1..35
                          note = Gene-trap integration site
source                    1..35
                          mol_type = other DNA
                          organism = synthetic construct
SEQUENCE: 74
gggtctttca ttctcaacat tccactcttc tctat                                    35

SEQ ID NO: 75             moltype = DNA  length = 35
FEATURE                   Location/Qualifiers
misc_feature              1..35
                          note = Gene-trap integration site
source                    1..35
                          mol_type = other DNA
                          organism = synthetic construct
SEQUENCE: 75
gggtctttca cctacagaga tagctcattt cttac                                    35

SEQ ID NO: 76             moltype = DNA  length = 35
FEATURE                   Location/Qualifiers
misc_feature              1..35
                          note = Gene-trap integration site
source                    1..35
                          mol_type = other DNA
                          organism = synthetic construct
SEQUENCE: 76
gggtctttca gtgcattggg aaattttgct accaa                                    35

SEQ ID NO: 77             moltype = DNA  length = 35
FEATURE                   Location/Qualifiers
misc_feature              1..35
                          note = Gene-trap integration site
source                    1..35
                          mol_type = other DNA
                          organism = synthetic construct
SEQUENCE: 77
gggtctttca ccaggcactg ggatagaaag gtgaa                                    35

SEQ ID NO: 78             moltype = DNA  length = 35
FEATURE                   Location/Qualifiers
misc_feature              1..35
                          note = Gene-trap integration site
source                    1..35
                          mol_type = other DNA
                          organism = synthetic construct
SEQUENCE: 78
gggtctttca caagtaaatg taatataaag atttt                                    35

SEQ ID NO: 79             moltype = DNA  length = 35
```

-continued

```
FEATURE                Location/Qualifiers
misc_feature           1..35
                       note = Gene-trap integration site
source                 1..35
                       mol_type = other DNA
                       organism = synthetic construct
SEQUENCE: 79
gggtctttca taagaaatga gctatctctg taggc                          35

SEQ ID NO: 80          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 80
gggtctttca gagaacatct cttctggagg aacaa                          35

SEQ ID NO: 81          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 81
gggtctttca aaagtattcc tatttccttg cagtc                          35

SEQ ID NO: 82          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 82
gggtctttca gttgtcattg aaaatccaag gatat                          35

SEQ ID NO: 83          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 83
gggtctttca gctgggagcc tggcttgata agcag                          35

SEQ ID NO: 84          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 84
gggtctttcc ccccgcacct ggcagcccta attct                          35

SEQ ID NO: 85          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 85
gggtctttca ggctccagct ccttccttgt tccgt                          35

SEQ ID NO: 86          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 86
gggtctttca agaatagtct actaaataca agaaa                          35
```

-continued

```
SEQ ID NO: 87          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 87
gggtctttca ggctaaggcc accgaaacca ttctg                               35

SEQ ID NO: 88          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 88
gggtctttca atgtgttatt ctttacatga gacag                               35

SEQ ID NO: 89          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 89
gggtctttca gaagaaggaa ccatttcaaa atgtt                               35

SEQ ID NO: 90          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 90
gggtctttca atgtactgaa atcctagaat tgcag                               35

SEQ ID NO: 91          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 91
gggtctttca gggtgtggtg gctcacacct ataat                               35

SEQ ID NO: 92          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 92
gggtctttca acaccactct gactagtttc taaat                               35

SEQ ID NO: 93          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 93
gggtctttca agcattatag aggccctcat taaaa                               35

SEQ ID NO: 94          moltype = DNA   length = 35
FEATURE                Location/Qualifiers
misc_feature           1..35
                       note = Gene-trap integration site
source                 1..35
                       mol_type = other DNA
                       organism = synthetic construct
SEQUENCE: 94
gggtctttca ttcttatgtg gacccagccc tcaaa                               35
```

-continued

```
SEQ ID NO: 95          moltype = DNA  length = 35
FEATURE                Location/Qualifiers
misc_feature           1..35
                       note = Gene-trap integration site
source                 1..35
                       mol_type = other DNA
                       organism = synthetic construct
SEQUENCE: 95
gggtctttca ggagcctctg gataaggaag agaga                              35

SEQ ID NO: 96          moltype = DNA  length = 35
FEATURE                Location/Qualifiers
misc_feature           1..35
                       note = Gene-trap integration site
source                 1..35
                       mol_type = other DNA
                       organism = synthetic construct
SEQUENCE: 96
gggtctttca catttagagt aaacactagta tcatc                             35

SEQ ID NO: 97          moltype = DNA  length = 35
FEATURE                Location/Qualifiers
misc_feature           1..35
                       note = Gene-trap integration site
source                 1..35
                       mol_type = other DNA
                       organism = synthetic construct
SEQUENCE: 97
gggtctttca ttatattatt gcacgtggaa acggg                              35

SEQ ID NO: 98          moltype = DNA  length = 35
FEATURE                Location/Qualifiers
misc_feature           1..35
                       note = Gene-trap integration site
source                 1..35
                       mol_type = other DNA
                       organism = synthetic construct
SEQUENCE: 98
gggtctttca gactaataag taaagattag aacta                              35

SEQ ID NO: 99          moltype = DNA  length = 35
FEATURE                Location/Qualifiers
misc_feature           1..35
                       note = Gene-trap integration site
source                 1..35
                       mol_type = other DNA
                       organism = synthetic construct
SEQUENCE: 99
gggtctttca cccttagtac tatgagccca gggca                              35

SEQ ID NO: 100         moltype = DNA  length = 35
FEATURE                Location/Qualifiers
misc_feature           1..35
                       note = Gene-trap integration site
source                 1..35
                       mol_type = other DNA
                       organism = synthetic construct
SEQUENCE: 100
gggtctttca gaagaagagg gacccatgtc ttcgg                              35

SEQ ID NO: 101         moltype = DNA  length = 35
FEATURE                Location/Qualifiers
misc_feature           1..35
                       note = Gene-trap integration site
source                 1..35
                       mol_type = other DNA
                       organism = synthetic construct
SEQUENCE: 101
gggtctttca ggatgaccac ctaaacccag ggaac                              35

SEQ ID NO: 102         moltype = DNA  length = 35
FEATURE                Location/Qualifiers
misc_feature           1..35
                       note = Gene-trap integration site
source                 1..35
                       mol_type = other DNA
                       organism = synthetic construct
SEQUENCE: 102
```

-continued

```
gggtctttca ggagaatcac ttgaacctgg gaggc                                   35

SEQ ID NO: 103          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 103
gggtctttca atgggtcagg ttccatttcc tgtga                                   35

SEQ ID NO: 104          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 104
gggtctttca catgtgttca ggtggtctct tctgg                                   35

SEQ ID NO: 105          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 105
gggtctttca ctccaagcca caagcactgg ccaca                                   35

SEQ ID NO: 106          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 106
gggtctttca actttatcct ccaagccaca agcac                                   35

SEQ ID NO: 107          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 107
gggtctttca caagccacaa gcactggcca cacca                                   35

SEQ ID NO: 108          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 108
gggtctttca tactcagtga accacttgca gaaag                                   35

SEQ ID NO: 109          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 109
gggtctttca agggtattca tggagaacct cgggg                                   35

SEQ ID NO: 110          moltype = DNA   length = 35
FEATURE                 Location/Qualifiers
misc_feature            1..35
                        note = Gene-trap integration site
source                  1..35
                        mol_type = other DNA
                        organism = synthetic construct
```

```
SEQUENCE: 110
gggtctttca agactttaac agagtgcttt tctcc                                          35

SEQ ID NO: 111          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 111
gggtctttca cccctgggct ccggctgaca gcgac                                          35

SEQ ID NO: 112          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 112
gggtctttca aaaccatttt attcactgac cacat                                          35

SEQ ID NO: 113          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 113
gggtctttca agaagaggca agtcacaagg agggg                                          35

SEQ ID NO: 114          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 114
gggtctttca atgtaagtgt atactcatac atttt                                          35

SEQ ID NO: 115          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 115
gggtctttca gagagaatcg taggtagttc tctgg                                          35

SEQ ID NO: 116          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 116
gggtctttca gcctcaaccc cctgagtagc tggca                                          35

SEQ ID NO: 117          moltype = DNA   length = 35
FEATURE                 Location/Qualifiers
misc_feature            1..35
                        note = Gene-trap integration site
source                  1..35
                        mol_type = other DNA
                        organism = synthetic construct
SEQUENCE: 117
gggtctttca cggccaactt taaaatcttg agagc                                          35

SEQ ID NO: 118          moltype = DNA   length = 35
FEATURE                 Location/Qualifiers
misc_feature            1..35
                        note = Gene-trap integration site
source                  1..35
                        mol_type = other DNA
```

-continued

```
                          organism = synthetic construct
SEQUENCE: 118
gggtctttca gtctctacta aaaaaataca aaaca                                   35

SEQ ID NO: 119            moltype = DNA   length = 35
FEATURE                   Location/Qualifiers
misc_feature              1..35
                          note = Gene-trap integration site
source                    1..35
                          mol_type = other DNA
                          organism = synthetic construct
SEQUENCE: 119
gggtctttca cctgttggcc ggtttagaag gagcc                                   35

SEQ ID NO: 120            moltype = DNA   length = 35
FEATURE                   Location/Qualifiers
misc_feature              1..35
                          note = Gene-trap integration site
source                    1..35
                          mol_type = other DNA
                          organism = synthetic construct
SEQUENCE: 120
gggtctttca tctacctgaa gtctgaagtc tcagc                                   35

SEQ ID NO: 121            moltype = AA   length = 285
FEATURE                   Location/Qualifiers
source                    1..285
                          mol_type = protein
                          organism = synthetic construct
SEQUENCE: 121
MLYLIGLGLG DAKDITVKGL EVVRRCSRVY LEAYTSVLTV GKEALEEFYG RKLVVADREE   60
VEQEADNILK DADISDVAFL VVGDPFGATT HSDLVLRATK LGIPYRVIHN ASIMNAVGCC  120
GLQLYKFGET VSIVFWTDTW RPESFFDKVK KNRQNGMHTL CLLDIKVKEQ SLENLIKGRK  180
IYEPPRYMSV NQAAQQLLEI VQNQRIRGEE PAVTEETLCV GLARVGADDQ KIAAGTLRQM  240
CTVDLGEPLH SLIITGGSIH PMEMEMLSLF SIPENSSESQ SINGL                  285

SEQ ID NO: 122            moltype = AA   length = 452
FEATURE                   Location/Qualifiers
source                    1..452
                          mol_type = protein
                          organism = synthetic construct
SEQUENCE: 122
MMGCFALQTV DTELTADSVE WCPLQGCRHL LACGTYQLRR PEDRPAGPQN KGGMEVKEPQ   60
VRLGRLFLYS FNDNNSIHPL VEVQRKDTSA ILDMKWCHIP VAGHALLGLA DASGSIQLLR  120
LVESEKSHVL EPLSSLALEE QCLALSLDWS TGKTGRAGDQ PLKIISSDST GQLHLLMVNE  180
TRPRLQKVAS WQAHQFEAWI AAFNYWHPEI VYSGGDDGLL RGWDTRVPGK FLFTSKRHTM  240
GVCSIQSSPH REHILATGSY DEHILLWDTR NMKQPLADTP VQGGVWRIKW HPFHHHLLLA  300
ACMHSGFKIL NCQKAMEERQ EATVLTSHTL PDSLVYGADW SWLLFRSLQR APSWSFPSNL  360
GTKTADLKGA SELPTPCHEC REDNDGEGHA RPQSGMKPLT EGMRKNGTWL QATAATTRDC  420
GVNPEEADSA FSLLATCSFY DHALHLWEWE GN                                452

SEQ ID NO: 123            moltype = AA   length = 387
FEATURE                   Location/Qualifiers
source                    1..387
                          mol_type = protein
                          organism = synthetic construct
SEQUENCE: 123
MDSIQESDVL NAVKTKLPPC CLRIFRNKII LVGTYDLDKS TGYRSGSLDV FTMDLKLLCS   60
NNTYGAILDL KLSPFDDTLI CTAHSTGNIM LWRIRCTKDD DFQSNELDIH AIANLQLFEK  120
DVLIASCHFS PLDCKKLLVT NTAGEAATID IRTLSVQFTA SAIAQAYSKL DKIDYEVQGA  180
TEKVIHVESG QFLKPHELEC WTAEFGSLQP FQDVVFTGGD DSRIMAHDLR SKEFIWSNNR  240
IHDAGVVSIK CSQPNFRNNK PTSIITGSYD DNIRSLDLRM MGESIFPGAN VPTVNKLACD  300
LGGGVWRFVE SPIDQEQSHH NGSDRLLVCC MYNGAKVVTM NDNSDEYFQI QHYLKKGHDS  360
MCYGGDWSNS LIATCSFYDN SLQTWIV                                      387

SEQ ID NO: 124            moltype = DNA   length = 30
FEATURE                   Location/Qualifiers
misc_feature              1..30
                          note = primer
source                    1..30
                          mol_type = other DNA
                          organism = synthetic construct
SEQUENCE: 124
gatcggatcc caccgagtac aagcccacgg                                         30

SEQ ID NO: 125            moltype = DNA   length = 28
FEATURE                   Location/Qualifiers
misc_feature              1..28
                          note = primer
```

-continued

```
source                      1..28
                            mol_type = other DNA
                            organism = synthetic construct
SEQUENCE: 125
gatcccatgg tcaggcaccg ggcttgcg                                       28

SEQ ID NO: 126          moltype = DNA   length = 47
FEATURE                 Location/Qualifiers
misc_feature            1..47
                            note = primer
source                  1..47
                            mol_type = other DNA
                            organism = synthetic construct
SEQUENCE: 126
gatcgctagc cgcatttctt ttttccagat ggtgagcaag ggcgagg                  47

SEQ ID NO: 127          moltype = DNA   length = 33
FEATURE                 Location/Qualifiers
misc_feature            1..33
                            note = primer
source                  1..33
                            mol_type = other DNA
                            organism = synthetic construct
SEQUENCE: 127
gatcggatcc ttacttgtac agctcgtcca tgc                                 33

SEQ ID NO: 128          moltype = DNA   length = 48
FEATURE                 Location/Qualifiers
misc_feature            1..48
                            note = primer
source                  1..48
                            mol_type = other DNA
                            organism = synthetic construct
SEQUENCE: 128
gatcgctagc cgcatttctt ttttccagat gaccgagtac aagcccac                 48

SEQ ID NO: 129          moltype = DNA   length = 32
FEATURE                 Location/Qualifiers
misc_feature            1..32
                            note = primer
source                  1..32
                            mol_type = other DNA
                            organism = synthetic construct
SEQUENCE: 129
gatcggatcc tcaggcaccg ggcttgcggg tc                                  32

SEQ ID NO: 130          moltype = DNA   length = 47
FEATURE                 Location/Qualifiers
misc_feature            1..47
                            note = primer
source                  1..47
                            mol_type = other DNA
                            organism = synthetic construct
SEQUENCE: 130
gatcatcgat cgcaggcgca atcttcgcat ttcttttttc cagatgg                  47

SEQ ID NO: 131          moltype = DNA   length = 33
FEATURE                 Location/Qualifiers
misc_feature            1..33
                            note = primer
source                  1..33
                            mol_type = other DNA
                            organism = synthetic construct
SEQUENCE: 131
gatcggatcc ttacttgtac agctcgtcca tgc                                 33

SEQ ID NO: 132          moltype = DNA   length = 48
FEATURE                 Location/Qualifiers
misc_feature            1..48
                            note = primer
source                  1..48
                            mol_type = other DNA
                            organism = synthetic construct
SEQUENCE: 132
gatcatcgat cgcaggcgca atcttcgcat ttcttttttc cagatgac                 48

SEQ ID NO: 133          moltype = DNA   length = 33
FEATURE                 Location/Qualifiers
misc_feature            1..33
```

-continued

```
                        note = primer
source                  1..33
                        mol_type = other DNA
                        organism = synthetic construct
SEQUENCE: 133
gatcggatcc ttacttgtac agctcgtcca tgc                                    33

SEQ ID NO: 134          moltype = DNA   length = 20
FEATURE                 Location/Qualifiers
misc_feature            1..20
                        note = oligonucleotide
source                  1..20
                        mol_type = other DNA
                        organism = synthetic construct
SEQUENCE: 134
ctgcagcatc gttctgtgtt                                                   20

SEQ ID NO: 135          moltype = DNA   length = 20
FEATURE                 Location/Qualifiers
misc_feature            1..20
                        note = oligonucleotide
source                  1..20
                        mol_type = other DNA
                        organism = synthetic construct
SEQUENCE: 135
tctccaaatc tcggtggaac                                                   20

SEQ ID NO: 136          moltype = DNA   length = 18
FEATURE                 Location/Qualifiers
misc_feature            1..18
                        note = oligonucleotide
source                  1..18
                        mol_type = other DNA
                        organism = synthetic construct
SEQUENCE: 136
aacagctcct cgcccttg                                                     18

SEQ ID NO: 137          moltype = DNA   length = 20
FEATURE                 Location/Qualifiers
misc_feature            1..20
                        note = oligonucleotide
source                  1..20
                        mol_type = other DNA
                        organism = synthetic construct
SEQUENCE: 137
tcgtgaccac cctgacctac                                                   20

SEQ ID NO: 138          moltype = DNA   length = 20
FEATURE                 Location/Qualifiers
misc_feature            1..20
                        note = oligonucleotide
source                  1..20
                        mol_type = other DNA
                        organism = synthetic construct
SEQUENCE: 138
ctgcagcatc gttctgtgtt                                                   20

SEQ ID NO: 139          moltype = DNA   length = 20
FEATURE                 Location/Qualifiers
misc_feature            1..20
                        note = oligonucleotide
source                  1..20
                        mol_type = other DNA
                        organism = synthetic construct
SEQUENCE: 139
tctccaaatc tcggtggaac                                                   20

SEQ ID NO: 140          moltype = DNA   length = 19
FEATURE                 Location/Qualifiers
misc_feature            1..19
                        note = primer
source                  1..19
                        mol_type = other DNA
                        organism = synthetic construct
SEQUENCE: 140
ctcggtggaa cctccaaat                                                    19

SEQ ID NO: 141          moltype = DNA   length = 20
FEATURE                 Location/Qualifiers
```

-continued

```
misc_feature          1..20
                      note = primer
source                1..20
                      mol_type = other DNA
                      organism = synthetic construct
SEQUENCE: 141
aagcctcttg ctgtttgcat                                                    20

SEQ ID NO: 142        moltype = DNA   length = 44
FEATURE               Location/Qualifiers
misc_feature          1..44
                      note = oligonucleotide
source                1..44
                      mol_type = other DNA
                      organism = synthetic construct
SEQUENCE: 142
aatgatacgg cgaccaccga gatctgatgg ttctctagct tgcc                         44

SEQ ID NO: 143        moltype = DNA   length = 41
FEATURE               Location/Qualifiers
misc_feature          1..41
                      note = oligonucleotide
source                1..41
                      mol_type = other DNA
                      organism = synthetic construct
SEQUENCE: 143
caagcagaag acggcatacg acccaggtta agatcaaggt c                            41

SEQ ID NO: 144        moltype = DNA   length = 44
FEATURE               Location/Qualifiers
misc_feature          1..44
                      note = oligonucleotide
source                1..44
                      mol_type = other DNA
                      organism = synthetic construct
SEQUENCE: 144
aatgatacgg cgaccaccga gatctgatgg ttctctagct tgcc                         44

SEQ ID NO: 145        moltype = DNA   length = 43
FEATURE               Location/Qualifiers
misc_feature          1..43
                      note = oligonucleotide
source                1..43
                      mol_type = other DNA
                      organism = synthetic construct
SEQUENCE: 145
caagcagaag acggcatacg acgttctgtg ttgtctctgt ctg                          43

SEQ ID NO: 146        moltype = DNA   length = 47
FEATURE               Location/Qualifiers
misc_feature          1..47
                      note = primer
source                1..47
                      mol_type = other DNA
                      organism = synthetic construct
SEQUENCE: 146
gatcgctagc cgcatttctt ttttccagat ggtgagcaag ggcgagg                      47

SEQ ID NO: 147        moltype = DNA   length = 33
FEATURE               Location/Qualifiers
misc_feature          1..33
                      note = primer
source                1..33
                      mol_type = other DNA
                      organism = synthetic construct
SEQUENCE: 147
gatcggatcc ttacttgtac agctcgtcca tgc                                     33

SEQ ID NO: 148        moltype = DNA   length = 48
FEATURE               Location/Qualifiers
misc_feature          1..48
                      note = primer
source                1..48
                      mol_type = other DNA
                      organism = synthetic construct
SEQUENCE: 148
gatcgctagc cgcatttctt ttttccagat gaccgagtac aagcccac                     48

SEQ ID NO: 149        moltype = DNA   length = 32
```

-continued

```
FEATURE                 Location/Qualifiers
misc_feature            1..32
                        note = primer
source                  1..32
                        mol_type = other DNA
                        organism = synthetic construct
SEQUENCE: 149
gatcggatcc tcaggcaccg ggcttgcggg tc                              32

SEQ ID NO: 150          moltype = DNA   length = 47
FEATURE                 Location/Qualifiers
misc_feature            1..47
                        note = primer
source                  1..47
                        mol_type = other DNA
                        organism = synthetic construct
SEQUENCE: 150
gatcatcgat cgcaggcgca atcttcgcat ttctttttc cagatgg              47

SEQ ID NO: 151          moltype = DNA   length = 33
FEATURE                 Location/Qualifiers
misc_feature            1..33
                        note = primer
source                  1..33
                        mol_type = other DNA
                        organism = synthetic construct
SEQUENCE: 151
gatcggatcc ttacttgtac agctcgtcca tgc                            33

SEQ ID NO: 152          moltype = DNA   length = 48
FEATURE                 Location/Qualifiers
misc_feature            1..48
                        note = primer
source                  1..48
                        mol_type = other DNA
                        organism = synthetic construct
SEQUENCE: 152
gatcatcgat cgcaggcgca atcttcgcat ttctttttc cagatgac            48

SEQ ID NO: 153          moltype = DNA   length = 33
FEATURE                 Location/Qualifiers
misc_feature            1..33
                        note = primer
source                  1..33
                        mol_type = other DNA
                        organism = synthetic construct
SEQUENCE: 153
gatcggatcc ttacttgtac agctcgtcca tgc                            33

SEQ ID NO: 154          moltype = DNA   length = 56
FEATURE                 Location/Qualifiers
misc_feature            1..56
                        note = primer
source                  1..56
                        mol_type = other DNA
                        organism = synthetic construct
SEQUENCE: 154
gatcatcgat gcgcaggcgc aatcttcgca tttctttttt ccaggatgac cgagta  56

SEQ ID NO: 155          moltype = DNA   length = 57
FEATURE                 Location/Qualifiers
misc_feature            1..57
                        note = primer
source                  1..57
                        mol_type = other DNA
                        organism = synthetic construct
SEQUENCE: 155
gatcatcgat gcgcaggcgc aatcttcgca tttctttttt ccagggatga ccgagta 57

SEQ ID NO: 156          moltype = DNA   length = 57
FEATURE                 Location/Qualifiers
misc_feature            1..57
                        note = primer
source                  1..57
                        mol_type = other DNA
                        organism = synthetic construct
SEQUENCE: 156
gatcatcgat gcgcaggcgc aatcttcgca tttctttttt ccaggatggt gagcaag 57
```

-continued

```
SEQ ID NO: 157          moltype = DNA   length = 58
FEATURE                 Location/Qualifiers
misc_feature            1..58
                        note = primer
source                  1..58
                        mol_type = other DNA
                        organism = synthetic construct
SEQUENCE: 157
gatcatcgat gcgcaggcgc aatcttcgca tttctttttt ccagggatgg tgagcaag      58

SEQ ID NO: 158          moltype = DNA   length = 24
FEATURE                 Location/Qualifiers
misc_feature            1..24
                        note = primer
source                  1..24
                        mol_type = other DNA
                        organism = synthetic construct
SEQUENCE: 158
aattagatct ttacaattta cgcg                                            24

SEQ ID NO: 159          moltype = DNA   length = 20
FEATURE                 Location/Qualifiers
misc_feature            1..20
                        note = primer
source                  1..20
                        mol_type = other DNA
                        organism = synthetic construct
SEQUENCE: 159
ctgcagcatc gttctgtgtt                                                 20

SEQ ID NO: 160          moltype = DNA   length = 20
FEATURE                 Location/Qualifiers
misc_feature            1..20
                        note = primer
source                  1..20
                        mol_type = other DNA
                        organism = synthetic construct
SEQUENCE: 160
tctccaaatc tcggtggaac                                                 20

SEQ ID NO: 161          moltype = DNA   length = 19
FEATURE                 Location/Qualifiers
misc_feature            1..19
                        note = primer
source                  1..19
                        mol_type = other DNA
                        organism = synthetic construct
SEQUENCE: 161
ctcggtggaa cctccaaat                                                  19

SEQ ID NO: 162          moltype = DNA   length = 38
FEATURE                 Location/Qualifiers
misc_feature            1..38
                        note = primer
source                  1..38
                        mol_type = other DNA
                        organism = synthetic construct
SEQUENCE: 162
gatcggccat taaggcctta attaagccac catggacg                             38

SEQ ID NO: 163          moltype = DNA   length = 31
FEATURE                 Location/Qualifiers
misc_feature            1..31
                        note = primer
source                  1..31
                        mol_type = other DNA
                        organism = synthetic construct
SEQUENCE: 163
gatcatcgat agtcggtggg cctcgggggc g                                    31

SEQ ID NO: 164          moltype = DNA   length = 37
FEATURE                 Location/Qualifiers
misc_feature            1..37
                        note = primer
source                  1..37
                        mol_type = other DNA
                        organism = synthetic construct
SEQUENCE: 164
gatcgcggcc gcgatgggct gtttcgccct gcaaacg                              37
```

```
SEQ ID NO: 165          moltype = DNA   length = 36
FEATURE                 Location/Qualifiers
misc_feature            1..36
                        note = primer
source                  1..36
                        mol_type = other DNA
                        organism = synthetic construct
SEQUENCE: 165
gatcgcggcc gctcagttcc cctcccactc ccagag                              36

SEQ ID NO: 166          moltype = DNA   length = 37
FEATURE                 Location/Qualifiers
misc_feature            1..37
                        note = primer
source                  1..37
                        mol_type = other DNA
                        organism = synthetic construct
SEQUENCE: 166
gatcgcggcc gcggtgaact tcacggtaga ccagatc                             37

SEQ ID NO: 167          moltype = DNA   length = 37
FEATURE                 Location/Qualifiers
misc_feature            1..37
                        note = primer
source                  1..37
                        mol_type = other DNA
                        organism = synthetic construct
SEQUENCE: 167
gtacgcggcc gcctacaatt tgtccaggaa gttgtcc                             37

SEQ ID NO: 168          moltype = DNA   length = 38
FEATURE                 Location/Qualifiers
misc_feature            1..38
                        note = oligonucleotide
source                  1..38
                        mol_type = other DNA
                        organism = synthetic construct
SEQUENCE: 168
aattcaatac ccctacgacg tgcccgacta cgcctaag                            38

SEQ ID NO: 169          moltype = DNA   length = 38
FEATURE                 Location/Qualifiers
misc_feature            1..38
                        note = oligonucleotide
source                  1..38
                        mol_type = other DNA
                        organism = synthetic construct
SEQUENCE: 169
tcgacttagg cgtagtcggg cacgtcgtag gggtattg                            38

SEQ ID NO: 170          moltype = DNA   length = 38
FEATURE                 Location/Qualifiers
misc_feature            1..38
                        note = primer
source                  1..38
                        mol_type = other DNA
                        organism = synthetic construct
SEQUENCE: 170
gggatcccag tgtggtggcc gagatggagc cgctggcg                            38

SEQ ID NO: 171          moltype = DNA   length = 40
FEATURE                 Location/Qualifiers
misc_feature            1..40
                        note = primer
source                  1..40
                        mol_type = other DNA
                        organism = synthetic construct
SEQUENCE: 171
ccgatcccac cacactgggt cactatctga ctcctccttg                          40

SEQ ID NO: 172          moltype = DNA   length = 65
FEATURE                 Location/Qualifiers
misc_feature            1..65
                        note = oligonucleotide
source                  1..65
                        mol_type = other DNA
                        organism = synthetic construct
SEQUENCE: 172
```

-continued

```
gatcggatcc tccaccatgg attacaagga tgacgacgat aagccaccag actgggaatt    60
cgatc                                                                65

SEQ ID NO: 173          moltype = DNA  length = 65
FEATURE                 Location/Qualifiers
misc_feature            1..65
                        note = oligonucleotide
source                  1..65
                        mol_type = other DNA
                        organism = synthetic construct
SEQUENCE: 173
gatcgaattc ccagtctggt ggcttatcgt cgtcatcctt gtaatccatg gtggaggatc    60
cgatc                                                                65

SEQ ID NO: 174          moltype = DNA  length = 38
FEATURE                 Location/Qualifiers
misc_feature            1..38
                        note = primer
source                  1..38
                        mol_type = other DNA
                        organism = synthetic construct
SEQUENCE: 174
gatcccacca gactggaagg aagtggttta ttggtcac                            38

SEQ ID NO: 175          moltype = DNA  length = 37
FEATURE                 Location/Qualifiers
misc_feature            1..37
                        note = primer
source                  1..37
                        mol_type = other DNA
                        organism = synthetic construct
SEQUENCE: 175
gatcccagtc tggtggttat gtgtcattca ccagccg                             37

SEQ ID NO: 176          moltype = DNA  length = 34
FEATURE                 Location/Qualifiers
misc_feature            1..34
                        note = primer
source                  1..34
                        mol_type = other DNA
                        organism = synthetic construct
SEQUENCE: 176
gatcccacca gactgggact cggtggagaa gggg                                34

SEQ ID NO: 177          moltype = DNA  length = 41
FEATURE                 Location/Qualifiers
misc_feature            1..41
                        note = primer
source                  1..41
                        mol_type = other DNA
                        organism = synthetic construct
SEQUENCE: 177
gatcccagtc tggtggctat ttttggcatg aattattaac c                        41

SEQ ID NO: 178          moltype = DNA  length = 34
FEATURE                 Location/Qualifiers
misc_feature            1..34
                        note = primer
source                  1..34
                        mol_type = other DNA
                        organism = synthetic construct
SEQUENCE: 178
gatcccacca gactgggagc cgctggcgcc catg                                34

SEQ ID NO: 179          moltype = DNA  length = 41
FEATURE                 Location/Qualifiers
misc_feature            1..41
                        note = primer
source                  1..41
                        mol_type = other DNA
                        organism = synthetic construct
SEQUENCE: 179
gatcccagtc tggtggtcag tcactatctg actcctcctt g                        41

SEQ ID NO: 180          moltype = DNA  length = 41
FEATURE                 Location/Qualifiers
misc_feature            1..41
                        note = primer
source                  1..41
```

-continued

```
                         mol_type = other DNA
                         organism = synthetic construct
SEQUENCE: 180
gatctctaga gaattcacca tggcagcggt tggggctggt g                          41

SEQ ID NO: 181         moltype = DNA   length = 31
FEATURE                Location/Qualifiers
misc_feature           1..31
                         note = primer
source                 1..31
                         mol_type = other DNA
                         organism = synthetic construct
SEQUENCE: 181
actggctagc cttcaccagc actgactttg g                                     31

SEQ ID NO: 182         moltype = DNA   length = 21
FEATURE                Location/Qualifiers
misc_feature           1..21
                         note = primer
source                 1..21
                         mol_type = other DNA
                         organism = synthetic construct
SEQUENCE: 182
cagcccttga agatcatcag c                                                21

SEQ ID NO: 183         moltype = DNA   length = 23
FEATURE                Location/Qualifiers
misc_feature           1..23
                         note = primer
source                 1..23
                         mol_type = other DNA
                         organism = synthetic construct
SEQUENCE: 183
gccagtaatt gaaagcagca atc                                              23

SEQ ID NO: 184         moltype = DNA   length = 20
FEATURE                Location/Qualifiers
misc_feature           1..20
                         note = primer
source                 1..20
                         mol_type = other DNA
                         organism = synthetic construct
SEQUENCE: 184
ctcacaggcg cctgaagtac                                                  20

SEQ ID NO: 185         moltype = DNA   length = 19
FEATURE                Location/Qualifiers
misc_feature           1..19
                         note = primer
source                 1..19
                         mol_type = other DNA
                         organism = synthetic construct
SEQUENCE: 185
ggaaagtggc agctggtag                                                   19

SEQ ID NO: 186         moltype = AA   length = 15
FEATURE                Location/Qualifiers
REGION                 1..15
                         note = Tryptic fragment
source                 1..15
                         mol_type = protein
                         organism = synthetic construct
SEQUENCE: 186
FDVHDVTLHA DVIHR                                                       15
```